US012584153B2

(12) United States Patent
Eichhorn et al.

(10) Patent No.: US 12,584,153 B2
(45) Date of Patent: Mar. 24, 2026

(54) ENZYME-MEDIATED PROCESS FOR MAKING AMBERKETAL AND AMBERKETAL HOMOLOGUES

(71) Applicant: Givaudan SA, Vernier (CH)

(72) Inventors: Eric Eichhorn, Zürich (CH); Felix Flachsmann, Duebendorf (CH); Andreas Goeke, Duebendorf (CH)

(73) Assignee: GIVAUDAN SA, Vernier (CH)

( * ) Notice: Subject to any disclaimer, the term of this patent is extended or adjusted under 35 U.S.C. 154(b) by 532 days.

(21) Appl. No.: 17/995,512

(22) PCT Filed: Apr. 14, 2021

(86) PCT No.: PCT/EP2021/059618

§ 371 (c)(1),
(2) Date: Oct. 5, 2022

(87) PCT Pub. No.: WO2021/209482

PCT Pub. Date: Oct. 21, 2021

(65) Prior Publication Data

US 2023/0175027 A1 Jun. 8, 2023

(30) Foreign Application Priority Data

Apr. 15, 2020 (GB) ...................................... 2005468

(51) Int. Cl.
*C12N 9/90* (2006.01)
*C11B 9/00* (2006.01)
*C12P 17/18* (2006.01)

(52) U.S. Cl.
CPC ............ *C12P 17/181* (2013.01); *C11B 9/008* (2013.01); *C12N 9/90* (2013.01); *C12Y 504/99017* (2013.01)

(58) Field of Classification Search
CPC .................................. C12P 17/18; C12N 9/90
See application file for complete search history.

(56) References Cited

U.S. PATENT DOCUMENTS

| | | | | |
|---|---|---|---|---|
| 3,144,465 A * | 8/1964 | Ruzicka | C11B 9/0073 512/14 |
| 2012/0135477 A1 | 5/2012 | Breuer et al. | |

FOREIGN PATENT DOCUMENTS

| | | | |
|---|---|---|---|
| JP | 2009060799 A | 3/2009 |
| WO | 2010139719 A2 | 12/2010 |
| WO | 2012066059 A2 | 5/2012 |
| WO | 2016050690 A1 | 4/2016 |
| WO | 2016170099 A1 | 10/2016 |
| WO | 2017001641 A1 | 1/2017 |
| WO | 2017140909 A1 | 8/2017 |
| WO | 2018114839 A2 | 6/2018 |
| WO | 2018157021 A1 | 8/2018 |

OTHER PUBLICATIONS

International Search Report for App. No. PCT/EP2021/059618 dated Jun. 30, 2021.

Written Opinion for App. No. PCT/EP2021/059618 dated Jun. 30, 2021.

Great Britain Search Report for App. No. 2005468.0 dated Sep. 30, 2020.

Boonsong Kongkathip, et al., Stereospecific Total Synthesis of Amberketal and a Homologue, Chemistry Letters, 1999, pp. 51-52, vol. 28, Issue 1, The Chemical Society of Japan.

Richard C. Cambie, et al., Chemistry of the Podocarpaceae. LVII*, The Preparation of Some 1,3-Dioxans with Ambergris-Type Odours, Australian Journal of Chemistry, 1981, pp. 1265-1284, vol. 34, Issue 6.

Tooru Fujiwara, et al., Stereoselective Synthesis of Allyl and Homoallyl Alchols by the Ring Opening Reactions of 2-(2-Phenylthiocyclobutyl)oxiranes and Oxetanes, Tetrahedron Letters, pp. 8435-8438, 1995, vol. 26, Issue 46, Elsevier Science Ltd.

Ina G. Reipen, et al., Zymomonas mobilis squalene-hopene cyclase gene (shc): cloning, DNA sequence analysis, and expression in *Escherichia coli*, Microbiology, 1995, pp. 155-161, vol. 141, Great Britain.

S. Neumann, et al., Purification, Partial Characterization and Substrate Specificity of a Squalene Cyclase from Bacillus acidocaldarius, Biological Chemistry Hoppe-Seyler, Aug. 1986, pp. 729-29, vol. 367.

Brigitte Seckler, et al., Characterization and partial purification of squalene-hopene cyclase from Bacillus acidocaldarius, Biochimica et Biophysica Acta (BBA), May 2, 1986, pp. 356-363, vol. 881, Issue 3, Elsevier.

Dietmar Ochs, et al., Cloning, expression, and sequencing of squalene-hopene cyclase, a key enzyme in triterpenoid metabolism, Journal of Bacteriology, Jan. 1992, pp. 298-302, vol. 174, Issue 1, American Society for Microbiology.

Miriam Seitz, et al., Substrate specificity of a novel squalene-hopene cyclase from Zymomonas mobilis, Journal of Molecular Catalysis B: Enzymatic, Dec. 2012, pp. 72-77, vol. 84, Elsevier.

Miriam Seitz, Characterization of the substrate specificity of squalenehopene cyclases (SHCs), PhD Dissertation, 2012.

Barrero, A. F. et al., "Communic Acids: Occurrence, Properties and Use as Chirons for the Synthesis of Bioactive Compounds", Molecules, Feb. 6, 2012, vol. 17, No. 2, pp. 1448-1467.

J.S. Yadav, et al., "Synthesis of (+)-amberketal and its analog from L-abietic acid", Tetrahedron, Jun. 27, 2007, vol. 63, Issue 39, pp. 9896-9902.

* cited by examiner

*Primary Examiner* — Tekchand Saidha
(74) *Attorney, Agent, or Firm* — Curatolo Sidoti & Trillis Co., LPA; Floyd Trillis, III; Salvatore A. Sidoti

(57) ABSTRACT

An enzyme-mediated method for the production of Amberketal and Amberketal homologues, the products of said method, and uses of said products.

16 Claims, 1 Drawing Sheet

Specification includes a Sequence Listing.

ENZYME-MEDIATED PROCESS FOR MAKING AMBERKETAL AND AMBERKETAL HOMOLOGUES

CROSS REFERENCE TO RELATED APPLICATIONS

This application is a national stage application of International Application No. PCT/EP2021/059618, filed 14 Apr. 2021, which claims priority from Great Britain Patent Application No. 2005468.0, filed 15 Apr. 2020, both of which applications are incorporated herein by reference.

SEQUENCE LISTING

Attached to this Amendment is a Sequence Listing as-filed in the International application. The Sequence Listing includes sequences for SEQ ID NOs.: 1-22. Please add the Sequence Listing to the present application.

TECHNICAL FIELD

The present invention generally relates to a method of making Amberketal and Amberketal homologues using a squalene-hopene cyclase (SHC) enzyme or enzyme variant. The invention further relates to compositions made by said method, the various uses of said compositions, and consumer products comprising said compositions.

BACKGROUND

Amberketal provides a powerful and tenacious ambery and woody odour that is useful in fragrance compositions alone or in combination with other woody or ambery ingredients. Amberketal is traditionally prepared from Manool via a number of chemical transformations. However, the supply of natural Manool is limited. It is therefore desirable to provide a new efficient and cost effective synthetic route to obtain Amberketal and amberketal homologues.

SUMMARY

In accordance with a first aspect of the present invention there is provided a method for Formula (I)

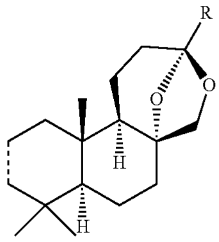

wherein the method comprises contacting a compound of formula (II) with a squalene-hopene cyclase (SHC) enzyme or enzyme variant, Formula (II)

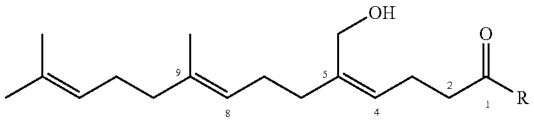

wherein R is H, methyl, or ethyl.

In certain embodiments, the method comprises contacting a compound of formula (I) wherein the double bond between C-8 and C-9 is in E-configuration and the double bond between C-4 and C-5 is in Z-configuration (E,Z-compound of formula (II)) with a squalene-hopene cyclase (SHC) enzyme (wild-type or variant enzyme).

In certain embodiments, the method comprises contacting a mixture comprising a compound of formula (II) wherein both double bonds are in E-configuration (E,E-compound) and a compound of formula (II) wherein the double bond between C-8 and C-9 is in E-configuration and the double bond between C-4 and C-5 is in Z-configuration (E,Z-compound) with a squalene-hopene cyclase (SHC) enzyme or enzyme variant.

In certain embodiments, the weight ratio of the E,Z-compound to the E,E-compound ranges from about 99:1 to about 10:90. For example, the weight ratio of the E,Z compound of formula (II) to the EE-compound of formula (II) may range from about 95:5 to about 50:50, or from about 80:20 to about 50:50 or from about 80:20 to about 60:40.

In accordance with a second aspect of the present invention there is provided a composition comprising, consisting essentially of, or consisting of a compound of formula (I) and a compound of formula (III), Formula (I)

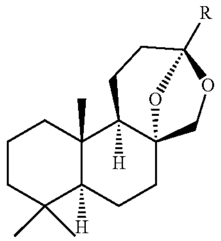

Formula (III)

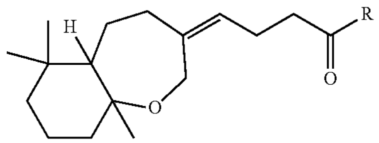

wherein R is H, methyl, or ethyl.

In accordance with a third aspect of the present invention there is provided a composition comprising, consisting essentially of, or consisting of a compound of formula (I), a compound of formula (IV), and a compound of formula (III), Formula (I)

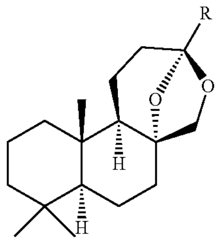

-continued

Formula (IV)

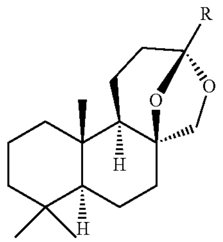

Formula (III)

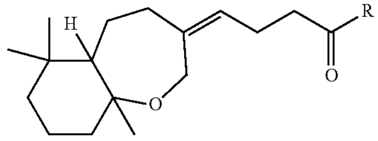

wherein R is H, methyl, or ethyl.

In accordance with a fourth aspect of the present invention there is provided a compound or composition obtained by or obtainable by the method of the first aspect of the present invention. The composition may, for example, be as defined in the second aspect of the present invention, including any embodiment thereof.

In accordance with a fifths aspect of the present invention there is provided a use of a composition of the second or third aspect of the present invention as or in a fragrance composition.

In accordance with a sixth aspect of the present invention there is provided a consumer product comprising a composition of the second or third aspect of the present invention.

In certain embodiments of any aspect of the present invention R is methyl. The compound of formula (I) may be referred to as (+)-Amberketal when R is methyl.

Certain embodiments of the present invention may provide one or more of the following advantages:

biocatalytic route to produce (+)-Amberketal and homologues of (+)-Amberketal;

milder reaction conditions (e.g. lower temperatures);

high selectivity;

use of alternative feed stock (e.g. alternative feed stock to that used for the chemical synthesis).

The details, examples and preferences provided in relation to any particular one or more of the stated aspects of the present invention will be further described herein and apply equally to all aspects of the present invention. Any combination of the embodiments, examples and preferences described herein in all possible variations thereof is encompassed by the present invention unless otherwise indicated herein, or otherwise clearly contradicted by context.

SUMMARY OF THE SEQUENCES

Figure 1:
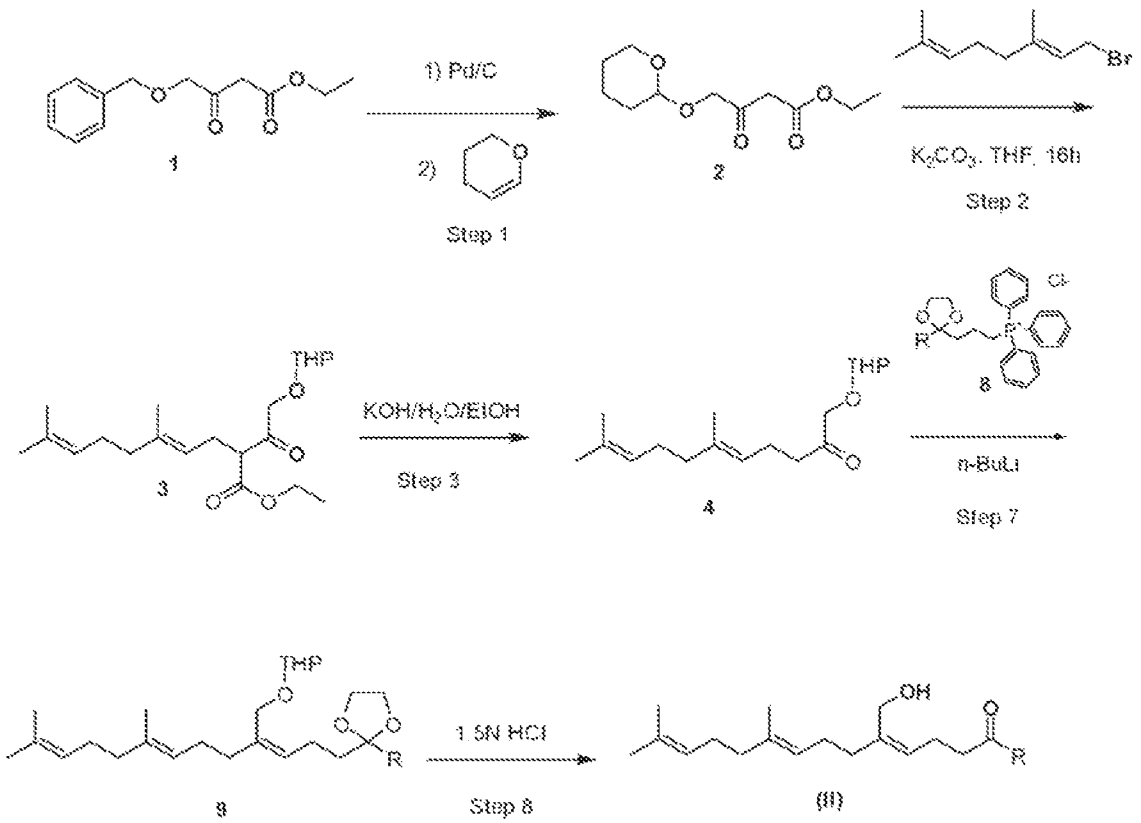
FIG. 1 shows the reaction scheme for the production of a compound of formula (II). For the compounds R is H, methyl or ethyl.

SEQ ID NO: 1 is the amino acid sequence of wild-type *Alicyclobacillus acidocaldarius* AacSHC SEQ ID NO: 2 is the nucleotide sequence of wild-type *Alicyclobacillus acidocaldarius* AacSHC.

SEQ ID NO: 3 is SEQ ID NO: 1 with the substitutions M132R, A224V, 1432T, A557T and R613S and may be referred to as SHC enzyme variant #65 herein.

SEQ ID NO: 4 is the nucleotide sequence of SHC variant #65.

SEQ ID NO: 5 corresponds to SEQ ID NO: 1 with the substitutions M132R, A224V, 1432T, Y81H, A557T and R613S and may be referred to as SHC enzyme variant #66 herein SEQ ID NO: 6 is the nucleotide sequence of SHC variant SHC #66.

SEQ ID NO: 7 corresponds to SEQ ID NO: 1 with the substitutions M132R, A224V, 1432T, T90A and R813S and may be referred to as SHC enzyme variant #90C7 herein. SEQ ID NO: 8 is the nucleotide sequence of SHC variant #90C7.

SEQ ID NO: 9 corresponds to SEQ ID NO: 1 with the substitutions M132R, A224V, 1432T, Y81H, H431L and A557T and may be referred to as SHC enzyme variant #11088 herein.

SEQ ID NO: 10 is the nucleotide sequence of SHC variant #11088.

SEQ ID NO: 11 corresponds to SEQ ID NO: 1 with the substitutions M132R, A224V, 1432T, A172T and M277K and may be referred to as SHC enzyme variant #115A7 herein.

SEQ ID NO: 12 is the nucleotide sequence of SHC variant #115A7.

SEQ ID NO: 13 corresponds to SEQ ID NO: 1 with the mutations M132R, A224V and 1432T and may be referred to as SHC enzyme variant 215G2 herein.

SEQ ID NO: 14 is the nucleotide sequence of SHC variant #215G2.

SEQ ID NO: 15 is the amino acid sequence of wild-type *Zymomonas mobilis* ZmoSHC1.

SEQ ID NO: 16 is the amino acid sequence of wild-type *Zymomonas mobilis* ZmoSHC2.

SEQ ID NO: 17 is the amino acid sequence of wild-type *Bradyrhizobium japonicum* BjaSHC.

SEQ ID NO: 18 is the amino acid sequence of wild-type *Thermosynechococcus elongatus* TeISHC.

SEQ ID NO: 19 is the amino acid sequence of wild-type *Acetobacter* pasteurianus ApaSHC1.

SEQ ID NO: 20 is the amino acid sequence of wild-type *Gluconobacter* morbiter GmoSHC.

SEQ ID NO: 21 is the amino acid sequence of wild-type *Bacillus megaterium* BmeSHC SEQ ID NO: 22 corresponds to SEQ ID NO: 1 with the substitutions M132R, A224V, 1432T, A557T and H431L and may be referred to as SHC enzyme variant #49 herein.

DETAILED DESCRIPTION

The present invention is based, at least in part, on the surprising finding that squalene-hopene cyclase (SHC) enzymes and enzyme variants can be used to make (+)-Amberketal and Amberketal homologues from polyunsaturated alcohols of formula (11). It is particular surprising that a substrate wherein the alkenyl chain is substituted with a hydroxymethyl group as defined by formula (II) herein undergoes an enzymatic polycyclisation reaction terminated by internal ketalisation.

Thus, there is provided herein in a first aspect a method of making a compound of formula (I), Formula (I)

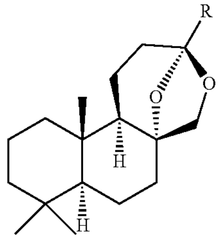

wherein the method comprises contacting a compound of formula (II) with a squalene-hopene cyclase (SHC) enzyme or enzyme variant, Formula (II)

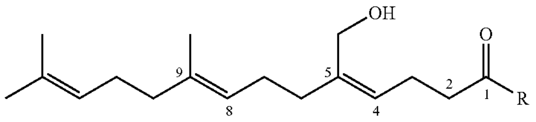

wherein R is H, methyl, or ethyl.

In certain embodiments both double bonds are in E-configuration (E,E-compound of formula (II)).

In certain embodiments the double between C-8 and C-9 is in E-configuration and the double bond between C-4 and C-5 is in Z-configuration (E,Z-compound of formula (II)).

In particular embodiments, R is methyl.

The methods provided herein enzymatically convert a compound of formula (II) to a compound of formula (I) using an SHC enzyme or enzyme variant (bioconversion reaction).

Compound of Formula (II)

The compound of formula (II) exists in the form of four different stereoisomers, for example, as a compound of formula (II) having an E,E- or E,Z-configuration.

In certain embodiments, the method comprises contacting an E,Z-compound of formula (II) with a squalene-hopene cyclase (SHC) enzyme or enzyme variant in the absence of any other stereoisomers of formula (II)

In other embodiments, the compound of formula (II) may, for example, be a mixture of stereoisomers. In certain embodiments, the mixture comprises the E,E-compound of formula (II) and one or more other stereoisomers of formula (II). In certain embodiments, the mixture comprises the E,Z-compound of formula (II) and one or more other stereoisomers of formula (II).

In certain embodiments, the method comprises contacting a mixture comprising, consisting essentially of, or consisting of E,E-compound of formula (II) and E,Z-compound of formula (II) with a SHC enzyme or enzyme variant. In certain embodiments, the composition does not comprise any other stereoisomers of formula (I).

The weight ratio of the E,Z-compound of formula (II) to total other stereoisomers of formula (II) may, for example, be equal to or greater than about 10:90. For example, the weight ratio of the E,Z-compound of formula (II) to total other stereoisomers of formula (II) may be equal to or greater than about 20:80 or equal to or greater than about 30:70 or equal to or greater than about 40:60 or equal to or greater than about 50:50 or equal to or greater than about 60:40 or equal to or greater than about 70:30 or equal to or greater than about 80:20 or equal to or greater than about 90:10 or equal to or greater than about 95:5, or equal to or greater than about 99:1.

The weight ratio of the E,Z-compound of formula (II) to total other stereoisomers of formula (II) may, for example, be equal to or less than about 99:1. For example, the weight ratio of the E,Z-compound of formula (II) to other stereoisomers of formula (II) may be equal to or less than about 95:5 or equal to or less than about 90:10 or equal to or less than about 85:15 or equal to or less than about 80:20 or equal to or less than about 60:40.

For example, the weight ratio of the E,Z-compound of formula (II) to total other stereoisomers of formula (II) may range from about 10:90 to about 99:1 or from about 10:90 to about 90:10 or from about 20.80 to about 80:20 or from about 50.50 to about 80:20 or from about 60:40 to about 80:20.

The weight ratio of the E,Z-compound of formula (II) to the E,E-compound of formula (II) may, for example, be equal to or greater than about 10:90. For example, the weight ratio of the E,Z-compound of formula (II) to the E,E-compound of formula (II) may be equal to or greater than about 20:80 or equal to or greater than about 30:70 or equal to or greater than about 40:60 or equal to or greater than about 50:50 or equal to or greater than about 60:40 or equal to or greater than about 70:30 or equal to or greater than about 80:20 or equal to or greater than about 90:10 or equal to or greater than about 95:5, or equal to or greater than about 99:1.

The weight ratio of the E,Z-compound of formula (II) to the E,E-compound of formula (II) may, for example, be equal to or less than about 99-1. For example, the weight ratio of the E,Z-compound of formula (II) to the E,E-compound of formula (II) may be equal to or less than about 95:5 or equal to or less than about 90:10 or equal to or less than about 85:15 or equal to or less than about 80:20 or equal to or less than about 70:30 or equal to or less than 60:40.

For example, the weight ratio of the E,Z-compound of formula (II) to the E,E-compound of formula (II) may range from about 10:90 to about 99:1 or from about 10:90 to about 90:10 or from about 20-80 to about 80:20 or from about 50-50 to about 80:20 or from about 60:40 to about 80:20.

The amount of each stereoisomer in a mixture of stereoisomers may, for example, be identified by gas chromatography or NMR spectroscopy analysis.

When R is methyl, the compound of formula (II) may be referred to as hydroxyfarnesylacetone, encompassing E,E-hydroxyfarnesylacetone, E,Z-hydroxyfarnesylacetone, Z,E-hydroxyfarnesylacetone and Z,Z-hydroxyfarnesylacetone, and mixtures thereof.

In certain embodiments, not all of the compound of formula (II) is converted to a compound of formula (I) or a by-product of the reaction. Thus, in certain embodiments, the compositions described herein, for example the compositions obtained by or obtainable by the methods described herein, may comprise a compound of formula (I) and a compound of formula (II).

In certain embodiments, any non-converted compound of formula (II) in the mixture made by the methods described herein may be separated from the other reaction products such that the compositions do not comprise any compounds of formula (II).

In alternative embodiments, all compound of formula (II) is converted to a compound of formula (I) or a by-product of the reaction by the methods described herein.

The number of stereoisomers of the compound of formula (II) present may influence the reaction rate. A SHC enzyme or enzyme variant may be capable of converting an E,Z-compound of formula (II) to a compound of formula (I) from a complex mixture of stereoisomers of the compound of formula (II) (said mixture may include only two of the stereoisomers, for example, E,Z-compound and E,E-compound of formula (II), or it may comprise three (i.e. E,Z-, and E,E- and Z,E- or Z,Z-compound of formula (II), or even all four stereoisomers) However, a lower conversion rate may be observed, which is consistent with the view that the other stereoisomers may compete with the E,Z-compound of formula (II) for access to the SHC enzyme or enzyme variant and thus may act as competitive inhibitors for the conversion of the E,Z-compound of formula (II) to the compound of formula (I) and/or also act as alternative substrates. Accordingly, the compound of formula (II) substrate may comprise an isomeric mixture of 2-4 isomers, preferably two isomers. Preferably the compound of formula (II) substrate comprises, consists essentially of or consists of an isomeric mixture of E,Z- and E,E-compound of formula (II).

The compound of formula (II) may be synthesized following the general procedure depicted by Fujiwara et al. (Tetrahedron Letters, 1995 Vol 36(46), 8435-8438). Alternatively the compounds of formula (II) may be obtained as briefly demonstrated in FIG. 1, wherein R is H, methyl or ethyl.

Compound of Formula (I)

The compound of formula (I) contains a number of chiral carbon atoms and thus one or more stereoisomers of the compound of formula (I) may also exist, including enantiomers and diastereomers. In addition to the compound of formula (I), the products made by the methods described herein may include one or more of the stereoisomers of the compound of formula (I). The stereoisomers obtained may depend on the stereoisomers of the compound of formula (II) that are used.

For example, a compound of formula (IV) may also be made in addition to the compound of formula (I), Formula (IV)

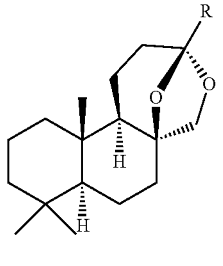

wherein R is H, methyl or ethyl.

The compound of formula (IV) wherein R is methyl is also known as (−)-epi-8-Amberketal.

In certain embodiments, no other stereoisomers of the compound of formula (I) are made by the method or are present in the product of the method, e.g. in certain embodiments a compound of formula (IV) is not made by the method or are present in the product of the method.

The methods described herein may, for example, make a compound of formula (I) and one or more other stereoisomers of the compound of formula (I) (e.g. a compound of formula (IV)). Thus, the compositions described herein, for example the compositions obtained by or obtainable by the methods described herein may comprise a compound of formula (I) and one or more stereoisomers of the compound of formula (I) (e.g. a compound of formula (IV)).

The weight ratio of the compound of formula (I) to total other stereoisomers of formula (I) may, for example be equal to or greater than about 50:50. For example, the weight ratio of the compound of formula (I) to total other stereoisomers of formula (I) may be equal to or greater than about 55:45 or equal to or greater than about 60:40 or equal to or greater than about 85:35 or equal to or greater than about 70:30 or equal to or greater than about 75:25 or equal to or greater than about 80:20 or equal to or greater than about 85-15 or equal to or greater than about 90:10 or equal to or greater than about 95:5, or equal to or greater than about 99:1.

For example, the compound of formula (I) may be the sole stereoisomeric form of formula (I) made or present in the composition. In other words, the composition may comprise 100 wt % of the compound of formula (I) based on the total weight of all stereoisomeric forms of the compound of formula (I) or have a weight ratio of compound of formula (I) to total other stereoisomers of formula (I) of 100:0. Alternatively, the weight ratio of the compound of formula (I) to total other stereoisomers of formula (I) may be less than about 100 wt %. For example, the weight ratio of the compound of formula (I) to total other stereoisomers of formula (I) may be equal to or less than about 99:1 or equal to or less than about 98:2 or equal to or less than about 97:3.

For example, the weight ratio of the compound of formula (I) to total other stereoisomers of formula (I) may be from about 50:50 to about 100:0 or from about 60:40 to about 99:1 or from about 70:30 to about 98:2 or from about 80:20 to about 97:3 or from about 90:10 to about 97.3.

The amount of each stereoisomer of the compound of formula (I) in a mixture of stereoisomers may, for example, be identified by gas chromatography on chiral columns or NMR spectroscopy in the presence of shift reagents.

The compound of formula (I) as obtained by the method described herein may, for example, be in amorphous form or in crystalline form.

The compound of formula (I) produced by the methods described herein may be isolated by steam extraction/distillation or organic solvent extraction using a non-water miscible solvent (to separate the reaction products and unreacted substrate from the biocatalyst which stays in the aqueous phase) followed by subsequent evaporation of the solvent to obtain a crude reaction product as determined by gas chromatography (GC) analysis. The steam extraction/distillation and organic solvent extraction methods are known to those skilled in the art.

By way of example, the resulting compound of formula (I) may be extracted from the whole reaction mixture using an organic solvent such as a non-water miscible solvent (for example toluene). Alternatively, the resulting compound of formula (I) may be extracted from the solid phase of the reaction mixture (obtained by, for example, centrifugation or filtration) using a water miscible solvent (for example ethanol) or a non-water miscible solvent (for example toluene). By way of further example, the compound of formula (I) may be present in the solid phase as crystals or in amorphous form and can be separated from the remaining solid phase (cell material or debris thereof) and the liquid phase also by means of filtration. By way of further example, at a temperature above the melting point of the compound of formula (I), the compound of formula (I) may form an oil layer on top of aqueous phase, which oil layer can be removed and collected. In order to ensure a complete recovery of compound of formula (I) after the oil layer is removed, an organic solvent may be added to the aqueous phase containing the biomass in order to extract any residual compound of formula (I) (e.g. (+)-Amberketal) contained in, or on or about the biomass. The organic layer can be combined with the oil layer, before the whole is further processed to isolate and purify the compound of formula (I). The compound of formula (I) may be further selectively crystallised to remove by-products and any unreacted compound of formula (II) from the final product. The term "selective crystallization" refers to a process step whereby the compound of formula (I) is caused to crystallise from a solvent whilst the by-products remain dissolved in the crystallising solvent to such an extent that isolated crystalline material contains only the compound of formula (I), or if it contains any by-products, then they are present only in olfactory acceptable amounts. The compound of formula (I), for example, is free or substantially free of by-products such as the compound of formula (III) or (IIIa). The selective crystallisation step may use a water miscible solvent such as ethanol or the like. The selective crystallisation of the compound of formula (I) may be influenced by the presence of unreacted compound of formula (II) and also the ratio of compound of formula (I) to the other detectable by-products. Even if only 10% conversion of the compound of formula (II) to compound of formula (I) is obtained, the selective crystallisation of the compound of formula (I) may be still possible.

The olfactive punty of the final compound of formula (I) product may be determined using a 10% ethanol extract in water or by testing the crystalline material. The final compound of formula (I) product is tested against a commercially available reference of compound of formula (I) for its olfactive purity, quality and its sensory profile. The compound of formula (I) material is also tested in application studies by experts in order to determine if the material meets the specifications with respect to its organoleptic profile.

Examples of suitable water miscible and non-water miscible organic solvents suitable for use in the extraction and/or selective crystallization of compound of formula (I) include but are not limited to aliphatic hydrocarbons, preferably those having 5 to 8 carbon atoms, such as pentane, cyclopentane, hexane, cyclohexane, heptane, octane or cyclooctane, halogenated aliphatic hydrocarbons, preferably those having one or two carbon atoms, such as dichloromethane, chloroform, carbon tetrachloride, dichloroethane or tetrachloroethane, aromatic hydrocarbons, such as benzene, toluene, the xylenes, chlorobenzene or dichlorobenzene, aliphatic acyclic and cyclic ethers or alcohols, preferably those having 4 to 8 carbon atoms, such as ethanol, isopropanol, diethyl ether, methyl tert.-butyl ether, ethyl tert.-butyl ether, dipropyl ether, diisopropyl ether, dibutyl ether, tetrahydrofuran or esters such as ethyl acetate or n-butyl acetate or ketones such as methyl isobutyl ketone or dioxane or mixtures of these. The solvents which are especially preferably used are the abovementioned heptane, Methyl tert-butyl ether (also known as MTBE, tert-butyl methyl ether, tertiary butyl methyl ether, and tBME), diisopropyl ether, tetrahydrofuran, ethyl acetate and/or mixtures thereof. Preferably, a water miscible solvent such as ethanol is used for the extraction of the compound of formula (I) from the solid phase of the reaction mixture. The use of ethanol is advantageous because it is easy to handle, it is non-toxic and it is environmentally friendly.

The term "isolated" as used herein refers to a bioconversion product such as the compound of formula (I) which has been separated or purified from components which accompany it. An entity that is produced in a cellular system different from the source from which it naturally originates is "isolated", because it will necessarily be free of components which naturally accompany it. The degree of isolation or purity can be measured by any appropriate method, e.g. gas chromatography (GC), HPLC or NMR analysis.

In some embodiments, the compound of formula (I) (e.g. (+)-Amberketal) is isolated and purified from the obtained crude product (e.g. to a purity of at least 80%, 81%, 82%, 83%, 84%, 85%, 86%, 87%, 88%, 89%, 90%, 91%, 92%, 93%, 94%, 95%, 96%, 97%, 98%, 99%, or 100%).

Desirably, the concentration of compound of formula (I) in the reaction broth obtained by the method described herein can be from about 1 mg/l to about 20.000 mg/l (20 g/l) or higher such as from about 20 g/l to about 200 g/l or from 100-500 g/l (including 150 g/l, 250 g/l, 300 g/l, 350 g/l, 400 g/l or 450 g/l).

Compound of Formula (III)

The methods described herein may, for example, make a compound of formula (III) as a by-product, wherein R is H, methyl, or ethyl:

Formula (III)

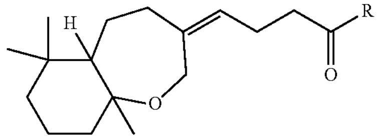

The compound of formula (III) may, for example, be a compound having the relative configuration of formula (IIIa), wherein R is H, methyl, or ethyl:

Formula (IIIa)

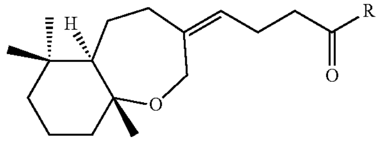

The methods described herein may, for example, make one or more stereoisomer(s) of compound of formula (III) The composition described herein may include one or more stereoisomer(s) of the compound of formula (III). The methods described herein may, for example, make a compound of formula (III) having the relative configuration shown in formula (IIIa). The composition described herein may therefore include a compound of formula (III) having the relative configuration shown in formula (IIIa). In certain embodiments, the only compound of formula (III) made by the methods described herein and therefore present in the compositions described herein are compounds having the relative configuration shown in formula (IIIa).

In certain embodiments, at least about 50 wt % of the total compounds of formula (III) have the relative configuration shown in formula (ilia). For example, at least about 60 wt % or at least about 70 wt % or at least about 80 wt % or at least about 90 wt % of the total compounds of formula (III) may have the relative configuration shown in formula (IIIa).

In certain embodiment, compounds having the configuration shown in formula (IIIa) are the only stereoisomers of formula (III). For example, 100 wt % of the total compounds of formula (III) have the relative configuration shown in formula (IIIa). In certain embodiments, equal to or less than about 99 wt % or equal to or less than about 95 wt % or equal to or less than about 90 wt % or equal to or less than about 85 wt % or equal to or less than about 80 wt % or equal to or less than about 75 wt % of the total compounds of formula (III) have the relative configuration shown in formula (IIIa).

For example, from about 50 wt % to about 100 wt % or from about 60 wt % to about 99 wt % or from about 70 wt % to about 95 wt % of the compounds of formula (III) have the relative configuration shown in formula (IIIa).

The amount of the different isomers of the compound of formula (III) in a mixture of stereoisomers may, for example, be identified by gas chromatography on chiral columns or NMR spectroscopy in the presence of shift reagents.

Products Obtained by the Methods Described Herein

There is also provided herein the products of the methods described herein. Thus, there is also provided herein a composition obtained by or obtainable by the method described herein, including all embodiments thereof.

There is provided herein a composition comprising, consisting essentially of or consisting of a compound of formula (I) and a compound of formula (III). The composition may, for example, further comprise one or more other stereoisomers of formula (I), for example a compound of formula (IV). The composition may, for example, comprise one or more stereoisomers of formula (III). For example, the composition may comprise a compound having the relative configuration of formula (IIIa). The composition may, for example, further comprise any unreacted compound of formula (II). In certain embodiments, R is methyl.

There is provided in a particular embodiment a composition comprising, consisting essentially of or consisting of a compound of formula (I), a compound of formula (IV), and a compound of formula (III).

There is also provided herein a composition comprising the compound of formula (I) and one or more stereoisomers of the compound of formula (I), for example a compound of formula (IV). The composition may, for example, further comprise a compound of formula (III). The composition may further comprise any unreacted compound of formula (II). In certain embodiments, R is methyl.

The weight ratio of the compound of formula (I) to the compound of formula (III) in the compositions described herein may, for example, range from about 60:40 to about 99:1. For example, the weight ratio of the compound of formula (I) to the compound of formula (III) may range from about 65:35 to about 99:1 or from about 70:30 to about 99:1 or from about 75:25 to about 99:1 or from about 80:20 to about 99:1 or from about 85:15 to about 99:1 or from about 90:10 to about 99:1 or from about 95:5 to about 99:1. For example, the weight ratio of the compound of formula (I) to the compound of formula (III) may range from about 65:35 to about 98:2 or from about 70:30 to about 97:3 or from about 75:25 to about 96:4 or from about 80:20 to about 95:5 or from about 85:15 to about 90:10.

The weight ratio of the compound of formula (I) to the compound of formula (II) in the crude reaction product described herein may, for example, range from about 90:10 to about 100:0. For example, the weight ratio of the compound of formula (I) to the compound of formula (II) in the compositions described herein may range from about 92:8 to about 100:0 or from about 94:6 to about 100:0 or from about 95:5 to about 100:0 or from about 96:4 to about 99.5:0.5 or from about 97:3 to about 99.0.1.0 or from about 98:2 to about 99.0:1.0.

Fragrance Compositions

There is further provided herein the use of the reaction products described herein in or as a fragrance composition.

Thus, there is also provided herein a fragrance composition comprising one or more compounds of formula (I). By "fragrance composition" is meant any composition comprising one or more compounds of formula (I) and a base material.

As used herein, the "base material" includes all known fragrance ingredients selected from the extensive range of natural products, and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, diluents, and other auxiliary agents commonly used in the art.

Fragrance ingredients known to the art are readily available commercially from the major fragrance manufacturers. Non-limiting examples of such ingredients include:

- essential oils and extracts, e.g. castoreum, costus root oil, oak moss absolute, geranium oil, tree moss absolute, basil oil, fruit oils, such as bergamot oil and mandarine oil, myrtle oil, palmarose oil, patchouli oil, petitgrain oil, jasmine oil, rose oil, sandalwood oil, wormwood oil, lavender oil and/or ylang-ylang oil;
- alcohols, e.g. cinnamic alcohol ((E)-3-phenylprop-2-en-1-ol); cis-3-hexenol ((2)-hex-3-en-1-ol); citronellol (3,7-dimethyloct-6-en-1-ol); dihydro myrcenol (2,6-dimethyloct-7-en-2-ol); Ebanol™ ((E)-3-methyl-5-(2,2,3-trimethylcyclopent-3-en-1-yl)pent-4-en-2-ol); eugenol (4-allyl-2-methoxyphenol): ethyl linalool ((E)-3,7-dimethylnona-1,6-dien-3-ol); farnesol ((2E,6Z)-3,7,11-trimethyldodeca-2,8,10-trien-1-ol); geraniol ((E)-3,7-dimethylocta-2,6-dien-1-ol); Super Muguet™ ((E)-6-ethyl-3-methyloct-6-en-1-ol); linalool (3,7-dimethylocta-1,6-dien-3-ol); menthol (2-isopropyl-5-methylcyclohexanol); Nerol (3,7-dimethyl-2,6-octadien-1-ol); phenyl ethyl alcohol (2-phenylethanol); Rhodinol™ (3,7-dimethyloct-6-en-1-ol); Sandalore™ (3-methyl-5-(2,2,3-trimethylcyclopent-3-en-1-yl)pentan-2-ol); terpineol (2-(4-methylcyclohex-3-en-1-yl) propan-2-ol); or Timberol™ (1-(2,2,6-timethylcyclohexyl)hexan-3-ol); 2,4,7-trimethylocta-2,6-dien-1-ol, and/or [1-methyl-2(5-methylhex-4-en-2-yl)cyclopropyl]-methanol;
- aldehydes and ketones, e.g. anisaldehyde (4-methoxybenzaldehyde); alpha amyl cinnamic aldehyde (2-benzylideneheptanal); Georgywood™ (1-(1,2,8,8-tetramethyl-1,2,3,4,5,6,7,8-octahydronaphthalen-2-yl) ethanone): Hydroxycitronellal (7-hydroxy-3,7-dimethyloctanal); Iso E Super® (1-(2,3,8,8-tetramethyl-1,2,3,4,5,6,7,8-octahydronaphthalen-2-yl) ethanone); Isoraldeine® ((E)-3-methyl-4-(2,6,6-trimethylcyclohex-2-en-1-yl)but-3-en-2-one): 3-(4-isobutyl-2-methylphenyl)propanal; maltol; methyl cedryl ketone; methylionone; verbenone; and/or vanillin;
- ether and acetals, e.g. Ambrox® (3a,6,6,9a-tetramethyl-2,4,5,5a,7,8,9,9b-octahydro-1H-benzo[e][1]benzofuran); geranyl methyl ether ((2E)-1-methoxy-3,7-dimethylocta-2,6-diene); rose oxide (4-methyl-2-(2-methylprop-1-en-1-yl)tetrahydro-2H-pyran); and/or Spirambrene® (2',2',3,7,7-pentamethylspiro[bicyclo[4.1.0]heptane-2,5'-[1.3]dioxane]);
- macrocycles, e.g. Ambrettolide ((2)-oxacycloheptadec-10-en-2-one); ethylene brassylate (1,4-dioxacycloheptadecane-5,17-dione); and/or Exaltolide® (16-oxacyclohexadecan-1-one); and
- heterocycles, e.g. isobutylquinoline (2-isobutylquinoline).

As used herein, "carrier material" means a material which is practically neutral from an odorant point of view, i.e. a material that does not significantly alter the organoleptic properties of odorants.

By "diluents" is meant any diluent conventionally used in conjunction with odorants, such as diethyl phthalate (DEP), dipropylene glycol (DPG), isopropyl myristate (IPM), triethyl citrate (TEC) and alcohol (e.g. ethanol).

The term "auxiliary agent" refers to ingredients that might be employed in a fragrance composition for reasons not specifically related to the olfactive performance of said composition. For example, an auxiliary agent may be an ingredient that acts as an aid to processing a fragrance ingredient or ingredients, or a composition containing said ingredient(s), or it may improve handling or storage of a fragrance ingredient or composition containing same, such as anti-oxidant adjuvant. Said anti-oxidant may be selected, for example, from Tinogard® TT (BASF). Tinogard® Q (BASF), Tocopherol (including its isomers, CAS 59-02-9; 364-49-8: 18920-62-2; 121854-78-2), 2,6-bis(1,1-dimethylethyl)-4-methylphenol (BHT, CAS 128-37-0) and related phenols, hydroquinones (CAS 121-31-9).

It might also be an ingredient that provides additional benefits such as imparting colour or texture. It might also be an ingredient that imparts light resistance or chemical stability to one or more ingredients contained in a fragrance composition.

A detailed description of the nature and type of auxiliary agent commonly used in fragrance compositions containing same cannot be exhaustive, but it has to be mentioned that said ingredients are well known to a person skilled in the art.

Various applications for the compound of formula (I) include but are not limited to a fine fragrance or a consumer product such as fabric care, toiletries, beauty care and cleaning products, detergent products, and soap products, including essentially all products where the currently available (+)-Amberketal ingredients are used commercially.

There is also provided herein a consumer product comprising a composition or fragrance composition as described herein, including any embodiment thereof. The consumer product may, for example, be a cosmetic product (e.g. a eau de parfum or eau de toilette), a cleaning product, a detergent product, or a soap product.

Intermediates and Starting Materials

There is also provided herein the intermediates and starting materials used in the methods described herein.

There is also provided herein a mixture comprising, consisting essentially of, or consisting of a compound of formula (II). For example, mixture may comprise, consist essentially of, or consist of a compound of formula (II) wherein both double bonds are in E-configuration (E,E-compound) and a compound of formula (II) wherein the double bond between C-8 and C-9 is in E-configuration and the double bond between C-4 and C-5 is in Z-configuration (E,Z-compound). In one embodiment, said mixture may comprise, consist essentially of, or consist of three of the stereoisomers of formula (II) (i.e. E,Z-, E,E- and Z,E- or Z,Z-compound of formula (II)), or even all four stereoisomers of formula (II).

The weight ratio of the E,Z-compound to the E,E-compound of formula (II) may, for example, be equal to or greater than about 10:90. For example, the weight ratio of the E,Z-compound to the EE-compound may be equal to or greater than about 20:80 or equal to or greater than about 30:70 or equal to or greater than about 40:60 or equal to or greater than about 50:50 or equal to or greater than about 60:40 or equal to or greater than about 70:30 or equal to or greater than about 80:20 or equal to or greater than about 90:10 or equal to or greater than about 95.5, or equal to or greater than 99:1.

The weight ratio of the E,Z-compound to the E,E-compound of formula (II) may, for example, be equal to or less than about 99:1. For example, the weight ratio of the E,Z-compound to the E,E-compound of formula (II) may be equal to or less than about 95:5 or equal to or less than about 90:10 or equal to or less than about 85:15 or equal to or less than about 80:20 or equal to or less than about 70:30 or equal to or less than 60:40.

For example, the weight ratio of the E,Z-compound of formula (II) to the E,E-compound of formula (II) may range from about 10:90 to about 99:1 or from about 10:90 to about 90:10 or from about 20:80 to about 80:20 or from about 50:50 to about 80:20 or from about 60.40 to about 80:20.

SHC Enzyme or Enzyme Variant

The methods described herein use an SHC enzyme or variant enzyme to enzymatically convert a compound of formula (II) to a compound of formula (I).

As used herein, the term "SHC enzyme" means a wild-type Squalene Hopene Cyclase enzyme that is naturally occurring in, for example thermophilic bacteria such as *Alicyclobacillus acidocaldarius*.

As used herein, the term "variant" is to be understood as a polypeptide which differs in comparison to the polypeptide from which it is derived by one or more changes in the amino acid sequence. The polypeptide from which a variant is derived is also known as the parent or reference polypeptide. Typically a variant is produced artificially, preferably by gene-technological means. Typically, the polypeptide from which the variant is derived is a wild-type enzyme or wild-type enzyme. However, the variants usable in the present disclosure may also be derived from homologs, orthologs, or paralogs of the parent polypeptide or from artificially constructed variants. The changes in the amino acid sequence may be amino acid exchanges (substitutions), insertions, deletions, N-terminal truncations, or C-terminal truncations, or any combination of these changes, which may occur at one or several sites.

As used herein, the term "SHC enzyme variant" means an enzyme that is derived from a wild-type SHC enzyme but has one or more amino acid alterations compared to the wild-type SHC enzyme and is therefore not naturally occurring. The one or more amino acid alterations may, for example, modify (e.g. increase) the enzymatic activity for a substrate (e.g. compound of formula (II)). Alternatively, a variant SHC enzyme can be derived from an already existing SHC enzyme variant.

Assays for determining and quantifying SHC enzyme and/or SHC enzyme variant activity are described herein and are known in the art. By way of example, SHC enzyme and/or SHC enzyme variant activity can be determined by incubating purified SHC enzyme or enzyme variant or extracts from host cells or a complete recombinant host organism that has produced the SHC enzyme or enzyme variant with an appropriate substrate under appropriate conditions and carrying out an analysis of the substrate and reaction products (e.g. by gas chromatography (GC) or HPLC analysis). Further details on SHC enzyme and/or SHC enzyme variant activity assays and analysis of the reaction products are provided in the Examples. These assays may include producing the SHC enzyme variant in recombinant host cells (e.g. *E. coli*).

As used herein, the term "activity" means the ability of an enzyme to react with a substrate to provide a target product. The activity can be determined in what is known as an activity test via the increase of the target product, the decrease of the substrate (or starting material) or via a combination of these parameters as a function of time. The SHC enzymes of the present disclosure may be characterized by their ability to convert a compound of formula (II) (e.g, hydroxyfarnesylacetone) to a compound of formula (I) (e.g. (+)-Amberketal).

A "biological activity" as used herein, refers to any activity a polypeptide may exhibit, including without limitation: enzymatic activity; binding activity to another compound (e.g. binding to another polypeptide, in particular binding to a receptor, or binding to a nucleic acid); inhibitory activity (e.g. enzyme inhibitory activity); activating activity (e.g. enzyme-activating activity): or toxic effects. It is not required that the variant exhibits such an activity to the same extent as the parent or wild-type polypeptide. In other embodiments, the SHC enzyme variants used herein show a better substrate conversion yield than the reference SHC enzyme (e.g, a wild-type SHC enzyme or a known SHC enzyme variant). In additional embodiments, the SHC enzyme variants used herein may show a modified (e.g. increased) productivity relative to the reference SHC enzyme (e.g. 215G2 AacSHC vs. wild-type AacSHC). The term "productivity" refers to the amount of recoverable product in grams per litre of reaction per hour of bioconversion time (i.e. time after the substrate was added).

As used herein, the term "amino acid alteration" means an insertion of one or more amino acids between two amino acids, a deletion of one or more amino acids or a substitution (which may be conservative or non-conservative) of one or more amino acids with one or more different amino acids relative to the amino acid sequence of a reference amino acid sequence. Substitutions replace the amino acids of the reference sequence with the same number of amino acids in the variant sequence. Reference amino acid sequences may, for example, be a wild-type (WT) amino acid sequence (for example SEQ ID NO: 1 or SEQ ID NO: 15, or SEQ ID NO: 16, or SEQ ID NO: 17, or SEQ ID NO: 18, or SEQ ID NO: 19, or SEQ ID NO: 20, or SEQ ID NO: 21) or may, for example, itself be an SHC enzyme variant sequence (for example the AacSHC variant 215G2—SEQ ID NO: 13).

The amino acid alterations can be easily identified by a comparison of the amino acid sequences of the SHC enzyme variant with the amino acid sequence of the reference amino acid sequence (e.g. a wild-type or variant SHC amino acid sequence).

Suitable sources of SHC enzymes include, for example, *Alicyclobacillus acidocaldarius* (Aac), *Zymomonas mobilis* (Zmo), *Bradyrhizobium japonicum* (Bja), *Gluconobacter morbifer* (Gmo), *Burkholderia ambifaria, Bacillus anthracis, Bacillus megaterium* (Bne), *Methylococcus capsulatus, Frankia alni, Acetobacter* pasteurianus (Apa), *Thermosynechococcus elongatus* (Tel). *Streptomyces coelicolor* (Sco), *Rhodopseudomonas palustris* (Rpa), *Teredinibacter* urnerae (Ttu), *Pelobacter carbinolicus* (Pca), and *Tetrahymena pyriformis* (see, for example WO 2010/139719, US 2012/01345477, WO 2012/066059, WO 2016/170099; WO 2018/157021, and JP2009060799, the contents of which are incorporated herein by reference). Suitable enzymes are also described in e.g. Neumann & Simon 1986, Biol Chem Hoppe-Seyler 367, 723-729; Seckler & Poralla 1986, Biochem Biophys Act 356-363; Ochs et al1990, J Bacteriol 174, 298-302; Seitz et al 2012, J Molecular Catalysis B: Enzymatic 84, 72-77; and Seitz 2012 PhD thesis (http://elib.uni-stuttgart.de/handle/1 1682/1400), the contents of which are incorporated herein by reference. These SHC enzymes and variants may be used in the methods described herein.

In particular, the SHC enzyme (e.g. from which the SHC enzyme variant may be derived) may be the *Alicyclobacillus acidocaldarius* (Aac) SHC enzyme, a *Zymomonas mobilis* (Zmo) SHC enzyme, a *Bradyrhizobium japonicum* (Bja) SHC enzyme, a *Bacillus megaterium* (Bme) SHC enzyme, or a *Gluconobacter* morbifer (Gmo) SHC enzyme. In a certain embodiment the SHC enzyme (e.g. from which the SHC enzyme variant may be derived) may be the *Alicyclobacillus acidocaldarius* (Aac) SHC enzyme. In a certain embodiment, the SHC enzyme (e.g. from which the SHC enzyme variant may be derived) may be the *Bacillus megaterium* (Bme) SHC enzyme.

For ease of reference, the designation "AacSHC" may be used to refer to the *Alicyclobacillus acidocaldarius* (Aac) SHC enzyme, "ZmoSHC" may be used to refer to a *Zymomonas mobilis* (Zmo) SHC enzyme, "BmeSHC" may be used to refer to the *Bacillus megaterium* (Bme) SHC enzyme, "BjaSHC" may be used to refer to the *Bradyrhizobium japonicum* (Bja) SHC enzyme and "GmoSHC" may be used to refer to the *Gluconobacter* morbifer (Gino) SHC enzyme.

AacSHCR ZmoSHC and BjaSHC enzyme sequences are disclosed in BASF 2010/139719, US 2012/01345477A1, Seitz et al (as cited above) and Seitz (2012 PhD thesis as cited above). Two different sequences are disclosed for ZmoSHC, referred to as ZmoSHC1 and ZmoSHC2 The GmoSHC enzyme sequence is disclosed in VA) 2018/157021. Table 1 discloses sources and accession numbers of wild-type SHC enzymes.

TABLE 1

Sources and accession numbers of wiki-type SHC enzymes.

| SHC Source Strain (SHC name) | Reference | Accession No. |
|---|---|---|
| *Alicyclobaciilus acidocaldarius* (WT AacSHC) | JP2009-060799 Neumann et al Biol Cham (1986) 367; 723-729 | NBRC15852 |
| *Zymomonas mobilis* (WT ZmoSHC) | WO2010139719 US20120135477 | ATCC31821 PF62207_2 Genpept Accession No AAV90172 |
| *Zymomonas mobilis* (WT ZmoSHC) | Reipen et al/(1995) Microbiology 141:155-181 | EMBL/Genbank Accession No. X80766 |
| *Bradryhizobium japonicum* (WT BjaSHC) | WO2010139719 US2012/0135477 | PF62207_5 |
| *Bacillus megaterium* (WT BmeSHC) | WO2017/150695 WO2019/045058 WO2015/033746 | WP_01 6763900.1 |
| *Burkholderia ambifaria* | WO2010139719 | |
| *Bacillus anthracis* | US2012/0135477 | |
| *Frankia alni* | | |
| *Bhodopseudomonas palustris* | | |
| *Gluconobacter morbifer* | WO 2018/157021 | |

The amino acid sequences of the wild-type AacSHC, wild-type ZmoSHC1, wild-type ZmoSHC2, wild-type BjaSHC, wild-type GmoSHC, wild-type TeISHC, wild-type ApaSHC1, and wild-type BmeSHC are also disclosed herein (SEQ ID NO: 1, SEQ ID NO: 15, SEQ ID NO: 16, SEQ ID NO: 17, SEQ ID NO: 18, SEQ ID NO. 19, SEQ ID NO: 20, and SEQ ID NO: 21 respectively).

The SHC enzymes or enzyme variants described herein and used in the methods described herein may, for example, be based on one of the wild-type amino acid sequences (SEQ ID NO 1, 13, 15, 16, 17, 18, 19, 20, 21), or a variant, homologue, mutant, derivative or fragment thereof. The SHC enzyme or enzyme variant may, for example, have an amino acid sequence with at least 30%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity to one of the wild-type amino acid sequences disclosed herein.

The SHC enzymes or enzyme variants described herein and used in the methods described herein may, for example, have a selectivity equal to or greater than about 75%. For example, the SHC enzyme or enzyme variant may have a selectivity equal to or greater than about 80% or equal to or greater than about 85% or equal to or greater than about 90% or equal to or greater than about 95%. For example, the SHC enzyme or enzyme variant may have a selectivity up to 100%, for example less than 100%, for example equal to or less than about 99.5% or equal to or less than about 99.0% or equal to or less than about 98.0% or equal to or less than about 97.0%.

"Percent (%) identity" with respect to the nucleotide sequence of a gene is defined as the percentage of nucleotides in a candidate DNA sequence that is identical with the nucleotides in the DNA sequence, after aligning the sequence and introducing gaps, if necessary, to achieve the maximum percent sequence identity, and not considering any conservative substitutions as part of the sequence identity. Alignment for purposes of determining percent nucleotide sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared. The terms "polypeptide" and "protein" are used interchangeably herein and mean any peptide-linked chain of amino acids, regardless of length or post-translational modification.

As used herein the term "derivative" includes but is not limited to a variant. The terms "derivative" and "variant" are used interchangeably herein.

Specific SHC enzymes and enzymes variants that may be used in the methods described herein are further described below.

Wild-Type SHC Enzymes

The methods described herein may, for example, use a SHC enzyme having 100% sequence identity to a wild-type SHC enzyme. The wild-type SHC enzyme does not have to have been obtained directly from its natural organism and may have been synthesized in a laboratory, for example using recombinant DNA techniques.

The wild-type SHC enzyme may, for example, be from *Alicyclobacillus acidocaldarius* (Aac), *Zymomonas mobilis* (Zmo), *Bradyrhizobium japonicum* (Bja), *Gluconobacter* morbifer (Gmo), *Burkholderia ambifaria, Bacillus anthracis, Bacillus megaterium* (Bme), *Methylococcus capsulatus, Frankia alni, Acetobacter* pasteurianus (Apa), *Thermosynechococcus elongatus* (Tel). *Streptomyces coelicolor* (Sco), *Rhodopseudomonas* palustrs (Rpa), *Teredinibacter* tunerae (Ttu), *Pelobacter carbinolicus* (Pca), or *Tetrahymena pyriformis* (see, for example WO 2010/139719, US 2012/01345477, WO 2012/066059, the contents of which are incorporated herein by reference).

In particular, the wild-type SHC enzyme may be an *Alicyclobacillus acidocaldarius* (Aac) SHC enzyme, a *Zymomonas mobilis* (Zmo) SHC enzyme, a *Bacillus megaterium* (Bme) SHC enzyme, a *Bradyrhizobium japonicum* (Bja) SHC enzyme or a *Gluconobacter* morbifer (Gmo) SHC enzyme. In particular, the wild-type SHC may be the *Alicyclobacillus acidocaldarius* (Aac) SHC enzyme, or the *Bacillus megaterium* (Bme) SHC enzyme, or a *Zymomonas mobilis* (Zmo) SHC enzyme (e.g. ZmoSHC1).

For ease of reference, the designation "AacSHC" may be used to refer to the *Alicyclobacillus acidocaldarius* SHC enzyme, "ZmoSHC" may be used to refer to the *Zymomonas mobilis* SHC enzymes ZmoSHC1 and ZmoSHC2, "BjaSHC" may be used to refer to the *Bradyrhizobium japonicum* SHC enzyme, "BmeSHC" may be used to refer to the *Bacillus megaterium* SHC enzyme, "GmoSHC" may be used to refer to the *Gluconobacter* morbifer SHC enzyme, "TelSHC" may be used to refer to the *Thermosynechococcus elongatus* SHC enzyme and "ApaSHC1" may be used to refer to the *Acetobacter* pasteurianus SHC enzyme.

The wild-type SHC enzyme amino acid sequence may, for example, be AacSHC (SEQ ID NO: 1), ZmoSHC1 (SEQ ID NO: 15), ZmoSHC2 (SEQ ID NO: 16), BjaSHC (SEQ ID NO: 17), GmoSHC (SEQ ID NO: 20), BmeSHC (SEQ ID NO: 21), TelSHC (SEQ ID NO: 18) or ApaSHC1 (SEQ ID NO: 19). For example, the wild-type SHC enzyme may be BmeSHC (SEQ ID NO: 21), ZmoSHC1 (SEQ ID NO: 15), or AacSHC (SEQ ID NO: 1).

SHC Variant Enzymes

The methods described herein may, for example, use an SHC enzyme variant (i.e. an SHC enzyme having less than 100% sequence identity to a wild-type SHC enzyme).

The methods described herein may, for example, use an SHC enzyme variant as described in WO 2016/170099 or WO 2018/157021, the contents of which are incorporated herein by reference. For example, the SHC enzyme variant used in the methods described herein may be the SHC enzyme variant 215G2, which is described in WO 2016/170099.

The SHC enzyme variant may, for example, have an amino acid sequence having at least about 70.0% identity to a wild-type SHC enzyme amino acid sequence. For example, the SHC enzyme variant may have an amino acid sequence having at least about 75.0% or at least about 80.0% or at least about 85.0% or at least about 90.0% or at least about 95.0% or at least about 95.5% or at least about 96.5% or at least about 97.0% or at least about 97.5% or at least about 98.0% or at least about 98.5% or at least about 99.0% identity to a wild-type SHC enzyme amino acid sequence.

The SHC enzyme variant has an amino acid sequence having less than 100% identity, for example equal to or less than about 99.5% or equal to or less than about 99.0% identity to a wild-type SHC enzyme amino acid sequence.

For example, the SHC enzyme variant may have from about 70.0% to about 99.5% or from about 80.0% to about 99.0% or from about 85.0% to about 98.5% or from about 90.0% to about 98.0% identity to a wild-type SHC enzyme amino acid sequence.

The wild-type SHC enzyme may, for example, be from *Alicyclobacillus acidocaldarius* (Aac), *Zymomonas mobilis* (Zmo), *Bradyrhizobium japonicum* (Bja), *Gluconobacter morbifer* (Gmo), *Burkholderia ambifaria, Bacillus anthracis, Bacillus megaterium* (Bme), *Methylococcus capsulatus, Frankia alni, Acetobacter* pasteurianus (Apa), *Thermosyn-*

*echococcus elongatus* (Tel). *Streptomyces coelicolor* (Sco), *Rhodopseudomonas palustris* (Rpa), *Teredinibacter turnerae* (Ttu), *Pelobacter carbinolicus* (Pca), or *Tetrahymena pyriformis* (see, for example WO 2010/139719, US 2012/01345477. WO 2012/066059, the contents of which are incorporated herein by reference).

The wild-type SHC enzyme amino acid sequence may, for example, be AacSHC (SEQ ID NO: 1), ZmoSHC1 (SEQ ID NO: 15). ZmoSHC2 (SEQ ID NO: 16), BjaSHC (SEQ ID NO: 17), GmoSHC (SEQ ID NO: 20), BmeSHC (SEQ ID NO: 21), TeISHC (SEQ ID NO: 18) or ApaSHC1 (SEQ ID NO: 19). For example, the wild-type SHC enzyme may be AacSHC (SEQ ID NO: 1).

Therefore, in certain embodiments, the SHC enzyme or SHC enzyme variant may have an amino acid sequence having at least about 70.0% identity to SEQ ID NO: 1, SEQ ID NO: 15, SEQ ID NO: 16. SEQ ID NO: 17, SEQ ID NO: 20, SEQ ID NO: 18. SEQ ID NO: 19, or SEQ ID NO: 21. For example, the SHC enzyme or SHC enzyme variant has an amino acid sequence having at least about 75.0% or at least about 80.0% or at least about 85.0% or at least about 90.0% or at least about 95.0% or at least about 95.5% or at least about 96.5% or at least about 97.0% or at least about 97.5% or at least about 98.0% or at least about 98.5% or at least about 99.0% identity to SEQ ID NO: 1, SEQ ID NO: 15. SEQ ID NO: 16, SEQ ID NO: 17, SEQ ID NO: 20, SEQ ID NO: 18, SEQ ID NO: 19, or SEQ ID NO: 21.

For example, the SHC enzyme variant may, for example, have an amino acid sequence having less than 100% identity, for example equal to or less than about 99.5% or equal to or less than about 99.0% identity to SEQ ID NO: 1, SEQ ID NO: 15, SEQ ID NO: 16, SEQ ID NO: 17, SEQ ID NO: 20, SEQ ID NO: 18. SEQ ID NO: 19, or SEQ ID NO: 21.

For example, the SHC enzyme variant may have from about 70.0% to about 99.5% or from about 80.0% to about 99.0% or from about 85.0% to about 98.5% or from about 90.0% to about 98.0% identity to SEQ ID NO: 1, SEQ ID NO: 15. SEQ ID NO: 16, SEQ ID NO: 17, SEQ ID NO: 20, SEQ ID NO: 18, SEQ ID NO: 19, or SEQ ID NO: 21.

"Percent (%) identity" with respect to a polypeptide or nucleotide sequence is defined respectively as the percentage of amino acids or nucleotides in a candidate sequence that are identical with the amino acids or nucleotides in the reference sequence, after aligning the sequence and introducing gaps, if necessary, to achieve the maximum percent sequence identity, and not considering any conservative substitutions as part of the sequence identity. Alignment for purposes of determining percent sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared. The terms "polypeptide" and "protein" are used interchangeably herein and mean any peptide-linked chain of amino acids, regardless of length or post-translational modification.

The similarity of nucleotide and amino acid sequences, i.e, the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90: 5873-5877), with hmmalign (HMMER package, http://hmmer.wustl.edu/) or with the CLUSTAL algorithm (Thompson, J D., Higgins, D. G. & Gibson, T. J. (1994) Nucleic Acids Res. 22, 4673-80) available eg, on https://www.ebi.ac.uk/Tools/msa/clustalo/ or the GAP program (mathematical algorithm of the University of Iowa) or the mathematical algorithm of Myers and Miller (1989—Cabios 4: 11-17). Preferred parameters used are the default parameters as they are set on https://www.ebi.ac.uk/Tools/msa/clustalo/.

Percentage sequence identity may be calculated using, for example, BLAST. BLAT or BlastZ (or BlastX). A similar algorithm is incorporated into the BLASTN and BLASTP programs of Altschul et al (1990) J. Mol. Biol. 215, 403-410. BLAST polynucleotide searches may be performed with the BLASTN program, score=100, word length=12, to obtain polynucleotide sequences that are homologous to those nucleic acids which encode the relevant protein. BLAST protein searches may be performed with the BLASTP program, score=50, word length=3, to obtain amino acid sequences homologous to the polypeptide.

To obtain gapped alignments for comparative purposes, Gapped BLAST may be utilized as described in Altschul et al (1997) Nucleic Acids Res. 25, 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1: 154-182) or Markov random fields. Men percentages of sequence identity are referred to in the present application, these percentages are calculated in relation to the full length of the longer sequence, if not specifically indicated otherwise.

In particular embodiments, % identity between two sequences is determined using CLUSTAL 0 (version 1.2.4).

The SHC enzyme variants may, for example, have increased enzymatic activity for the conversion of the compound of formula (II) to the compound of formula (I) compared to the parent SHC enzyme. Increased enzymatic activity may refer to any aspect of the enzymatic conversion of the compound of formula (II) to the compound of formula (I) including, for example, increased total conversion of the compound of formula (II) to the compound of formula (I), increased rate of conversion of the compound of formula (II) (e.g. in the first 4 hours, or first 6 hours, or in the first 12 hours of reaction), increased production of the compound of formula (I), and/or decreased production of by-products. Increased enzymatic activity may be defined by increased productivity in general, which may be defined in terms of compound of formula (I) produced per hour, per gram of biocatalyst and per litre of reaction.

The SHC enzyme variants may, for example, provide increased compound of formula (II) conversion compared to the parent SHC enzyme. Therefore, the process described herein may have an increased level of compound of formula (II) conversion compared to the process using the parent SHC enzyme. The SHC enzyme variants may, for example, provide increased rate of compound of formula (II) conversion compared to the parent SHC enzyme Therefore, the process described herein may have an increased rate of compound of formula (II) conversion compared to the parent SHC enzyme. The SHC enzyme variant may, for example, provide increased rate of compound of formula (II) conversion over the first 4 hours or over the first 2 hours, or first 4 hours, or first 6 hours, or over the first 8 hours or over the first 12 hours or over the first 24 hours of the reaction compared to the parent SHC enzyme. Therefore, the process described herein may have an increased rate of compound of formula (II) conversion over the first 2 hour, or first 4 hours or over the first 6 hours or over the first 8 hours or over the first 12 hours or over the first 24 hours of the reaction compared to the parent SHC enzyme. This may be when compared to using both enzymes (i.e, the SHC enzyme variant and the parent SHC enzyme) under the same reaction conditions (e.g. same pH and temperature) or when compared to using each enzyme under conditions that have been individually defined as optimal for its activity (e.g. optimized pH and temperature), and which may be different to each other.

The conversion of compound of formula (II) to compound of formula (I) may, for example, be determined using an activity assay as described above and may be calculated as gram of recoverable product per gram of feedstock (which can be calculated if desired as a percent molar conversion rate).

The processes for making the compound of formula (I) disclosed herein may be carried out at the optimum temperature range or optimum temperature and/or the optimum pH range or optimum pH and/or the SDS optimum concentration range or optimum SDS concentration for the specific enzyme used, as set out in the Examples below.

Nucleic Acids and Methods of Making Nucleic Acids

The SHC enzyme and enzyme variants described herein may be encoded by a nucleic acid sequence. The nucleic acid containing the coding sequence may, for example, be an isolated nucleic acid.

Thus, there is provided herein a construct comprising a nucleic acid sequence encoding an SHC enzyme or enzyme variant as described herein. As used herein, a "construct" is an artificially created segment of nucleic acid that is to be transfected into a target cell. The construct may comprise the nucleic acid sequence encoding the SHC enzyme or enzyme variant and a gene expression controller (e.g. promoter).

There is further provided herein a vector comprising a construct as described herein. As used herein, a "vector" is a DNA molecule that is used as a vehicle to artificially carry foreign genetic material into a cell where it can be replicated and/or expressed. The vector may, for example, be a plasmid, a viral vector, a cosmid, or an artificial chromosome.

The terms "construct" and "vector" may overlap, for example where the construct is a plasmid.

The term "nucleic acid" or "nucleic acid molecule" as used herein shall specifically refer to polynucleotides of the disclosure which can be DNA, cDNA, genomic DNA, synthetic DNA, or RNA, and can be double-stranded or single-stranded, the sense and/or an antisense strand. The term "nucleic acid" or "nucleic acid molecule" shall particularly apply to the polynucleotide(s) as used herein, e.g. as full-length nucleotide sequence or fragments or parts thereof, which encodes a polypeptide with enzymatic activity, e.g. an enzyme of a metabolic pathway, or fragments or parts thereof, respectively.

The term also includes a separate molecule such as a cDNA where the corresponding genomic DNA has introns and therefore a different sequence; a genomic fragment that lacks at least one of the flanking genes; a fragment of cDNA or genomic DNA produced by polymerase chain reaction (PCR) and that lacks at least one of the flanking genes; a restriction fragment that lacks at least one of the flanking genes; a DNA encoding a non-naturally occurring protein such as a fusion protein (e.g. a His tag), mutein, or fragment of a given protein; and a nucleic acid which is a degenerate variant of a cDNA or a naturally occurring nucleic acid. In addition, it includes a recombinant nucleotide sequence that is part of a hybrid gene, i.e. a gene encoding a non-naturally occurring fusion protein. Fusion proteins can add one or more amino acids (such as but not limited to Histidine (His)) to a protein, usually at the N-terminus of the protein but also at the C-terminus or fused within regions of the protein. Such fusion proteins or fusion vectors encoding such proteins typically serve three purposes: (i) to increase production of recombinant proteins; (ii) to increase the solubility of the recombinant protein; and (iii) to aid in the purification of the recombinant protein by providing a ligand for affinity purification.

The term "nucleic acid sequence" also includes codon-optimised sequences suitable for expression in a particular microbial host cell (e.g. *E. coli* host cell). As used herein, the term "codon optimized" means a nucleic acid protein coding sequence which has been adapted for expression in a particular prokaryotic or a eukaryotic host cell, particularly bacterial host cells such as *E. coli* host cells considering its particular codon-usage, by e.g. substitution of one or more or preferably a significant number of codons with codons that are more frequently used in bacterial host cell genes (e.g. *E. coli* genes).

In this regard, the nucleotide sequence or gene encoding the reference amino acid sequence (e.g. SEQ ID NO. 1 or SEQ ID NO: 13) and variants/derivatives thereof may be the original one as found in the source or the gene can be codon-optimized for the selected host organisms, such as e.g. *E. coli.*

In a further aspect the nucleic acid sequence(s) of the present disclosure is/are operatively linked to expression control sequences allowing expression in prokaryotic and/or eukaryotic host cells. As used herein, "operatively linked" means incorporated into a genetic construct so that expression control sequences effectively control expression of a coding sequence or of a gene of interest. The transcriptional/translational regulatory elements referred to above include but are not limited to inducible and non-inducible, constitutive, cell cycle regulated, metabolically regulated promoters, enhancers, operators, silencers, repressors and other elements that are known to those skilled in the art and that drive or otherwise regulate gene expression. Such regulatory elements include but are not limited to regulatory elements directing constitutive expression or which allow inducible expression like, for example, CUP-1 promoter, the tot-repressor as employed, for example, in the tet-on or tet-off systems, the lac system, the trp system regulatory elements. By way of example, Isopropyl A-D-1-thiogalactopyranoside (IPTG) is an effective inducer of gene expression in the concentration range of e.g. 100 μM to 1.0 mM. This compound is a molecular mimic of allolactose, a lactose metabolite that triggers transcription of the lac operon, and it is therefore used to induce gene expression when the gene is under the control of the lac operator Another example of a regulatory element which induces gene expression is lactose. Similarly, the nucleic acid molecule(s) of the present disclosure can form part of a hybrid gene encoding additional polypeptide sequences, for example, a sequence that functions as a marker or reporter. Examples of marker and reporter genes including beta-lactamase, chloramphenicol acetyltransferase (CAT), adenosine deaminase (ADA), aminoglycoside phosphotransferase dihydrofolate reductase (DHFR), hygromycin-B-phosphotransferase (HPH), thymidine kinase (TK), lacZ (encoding beta-galactosidase), and xanthine guanine phosphoribosyltransferase (XGPRT). As with many of the standard procedures associated with the practice of the disclosure, skilled artisans will be aware of additional useful reagents, for example, additional sequences that can serve the function of a marker or reporter.

There is also provided herein a recombinant polynucleotide encoding the SHC enzyme or variant thereof, which may be inserted into a vector for gene expression and optional enzyme purification. One type of vector is a plasmid representing a circular double stranded DNA loop into which additional DNA segments are ligated. Certain vectors can control the expression of genes to which they are functionally linked. These vectors are called "expression vectors". Usually expression vectors suitable for DNA recombination techniques are of the plasmid type. Typically, an expression vector comprises a gene for the production of the SHC wild-type or variant enzyme or as described herein. In the present description, the terms "plasmid" and "vector" may be used interchangeably since the plasmid is the vector type most often used.

Such vectors can include DNA sequences which include but are not limited to DNA sequences that are not naturally present in the host cell, DNA sequences that are not normally transcribed into RNA or translated into a protein ("expressed") and other genes or DNA sequences which one desires to introduce into the non-recombinant host. It will be appreciated that typically the genome of a recombinant host described herein is augmented through the stable introduction of one or more recombinant genes. However, autonomous or replicative plasmids or vectors can also be used within the scope of this disclosure. Moreover, the present disclosure can be practiced using a low copy number, e.g. a single copy, or high copy number (as exemplified herein) plasmid or vector.

The vector of the present disclosure includes plasmids, phagemids, phages, cosmids, artificial bacterial and artificial yeast chromosomes, knock-out or knock-in constructs, synthetic nucleic acid sequences or cassettes and subsets may be produced in the form of linear polynucleotides, plasmids, megaplasmids, synthetic or artificial chromosomes, such as plant, bacterial, mammalian or yeast artificial chromosomes.

It is preferred that the proteins encoded by the introduced polynucleotide are expressed within the cell upon introduction of the vector. The plasmids are often standard cloning vectors, e.g. bacterial multicopy plasmids. The substrates can be incorporated into the same or different plasmids. Often at least two different types of plasmid having different types of selectable markers are used to allow selection for cells containing at least two types of vectors.

Typically bacterial or yeast cells may be transformed with any one or more nucleotide sequences as is well known in the art. For in vivo recombination, the gene to be recombined with the chromosome or other genes is used to transform the host using standard transforming techniques. In a suitable embodiment DNA providing an origin of replication is included in the construct. The origin of replication may be suitably selected by the skilled person. Depending on the nature of the genes, a supplemental origin of replication may not be required if sequences are already present with the genes that are operable as origins of replication themselves.

Host Cells, Methods of Making Host Cells and Methods of Making The Compound of Formula (I) Using Host Cells Recombinant host cells may be used in the methods described herein.

There is further provided herein a recombinant host cell comprising a nucleic acid sequence or a construct or a vector as described herein. There is further provided herein a recombinant host cell that produces an SHC enzyme or enzyme variant as described herein.

The processes described herein for producing the compound of formula (I) may, for example, comprise culturing a recombinant host cell as described herein. As used herein, the term "culturing" refers to a process multiplying living cells such that they produce an SHC enzyme or enzyme variant as described herein that can be used in a process for producing the compound of formula (I) as described herein.

A bacterial or yeast cell may be transformed by exogenous or heterologous DNA when such DNA has been introduced inside the cell. The transforming DNA may or may not be integrated, i.e. covalently linked into the chromosome of the cell. In prokaryotes, and yeast, for example, the transforming DNA may be maintained on an episomal element such as a plasmid. With respect to eukaryotic cells, a stably transfected cell is one in which the transfected DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

Generally, the introduced DNA is not originally resident in the host that is the recipient of the DNA, but it is within the scope of the disclosure to isolate a DNA segment from a given host, and to subsequently introduce one or more additional copies of that DNA into the same host, e.g. to enhance production of the product of a gene or alter the expression pattern of a gene. In some instances, the introduced DNA will modify or even replace an endogenous gene or DNA sequence, e g. by homologous recombination or site-directed mutagenesis. Suitable recombinant hosts include microorganisms, plant cells, and plants.

The present disclosure also features recombinant hosts. The term "recombinant host", also referred to as a "genetically modified host cell" or a "transgenic cell" denotes a host cell that comprises a heterologous nucleic acid or the genome of which has been augmented by at least one incorporated DNA sequence. A host cell of the present disclosure may be genetically engineered with the polynucleotide or the vector as outlined above.

The host cells that may be used for purposes of the disclosure include but are not limited to prokaryotic cells such as bacteria (for example, *E. coli* and *B. subtilis*), which may, for example, be transformed with, for example, recombinant bacteriophage DNA, plasmid DNA, bacterial artificial chromosome, or cosmid DNA expression vectors containing the polynucleotide molecules of the disclosure; simple eukaryotic cells like yeast (for example, *Saccharomyces* and *Pichia*), which may, for example, be transformed with, for example, recombinant yeast expression vectors containing the polynucleotide molecule of the disclosure. Depending on the host cell and the respective vector used to introduce the polynucleotide of the disclosure the polynucleotide can integrate, for example, into the chromosome or the mitochondrial DNA or can be maintained extrachromosomally like, for example, episomally or can be only transiently comprised in the cells.

The term "cell" as used herein in particular with reference to genetic engineering and introducing one or more genes or an assembled cluster of genes into a cell, or a production cell is understood to refer to any prokaryotic or eukaryotic cell. Prokaryotic and eukaryotic host cells are both contemplated for use according to the disclosure, including bacterial host cells like *E. coli* or *Bacillus* sp., yeast host cells, such as *S. cerevisiae*, insect host cells, such as Spodoptora *frugiperda* or human host cells, such as HeLa and Jurkat.

Specifically, the cell is a eukaryotic cell, preferably a fungal, mammalian or plant cell, or a prokaryotic cell. Suitable eukaryotic cells include, for example, without limitation, mammalian cells, yeast cells, or insect cells (including Sf9), amphibian cells (including melanophore cells), or worm cells including cells of *Caenorhabditis* (including *Caenorhabditis elegans*). Suitable mammalian cells include, for example, without limitation. COS cells (including Cos-1 and Cos-7). CHO cells, HEK293 cells, HEK293T cells, HEK293 T-Rex™ cells, or other transfectable eukaryotic cell lines. Suitable bacterial cells include without limitation *E. coli.*

Preferably prokaryotes, such as *E. coli, Bacillus, Streptomyces*, or mammalian cells, like HeLa cells or Jurkat cells, or plant cells, like *Arabidopsis*, may be used.

The cell may, for example, be selected from prokaryotic, yeast, plant, and/or insect host cells.

Preferably the cell is an *Aspergillus* sp. or a fungal cell, preferably, it can be selected from the group consisting of the genera *Saccharomyces, Candida, Kluyveromyces, Hansenula, Schizosaccharomyces, Yarrowia, Pichia* and *Aspergillus.*

Preferably, the cell is a bacteria cell, for example, of genus selected from *Escherichia, Streptomyces, Bacillus, Pseudomonas. Lactobacillus* and *Lactococcus*. For example, the bacteria may be *E. coli.*

Preferably the *E. coli* host cell is an *E. coli* host cell which is recognized by the industry and regulatory authorities (including but not limited to an *E. coli* K12 host cell or an *E. coli* BL21 host cell).

One preferred host cell to use with the present disclosure is *E. coli*, which may be recombinantly prepared as described herein. Thus, the recombinant host may be a recombinant *E. coli* host cell. There are libraries of mutants, plasmids, detailed computer models of metabolism and other information available for *E. coli*, allowing for rational design of various modules to enhance product yield.

In one embodiment, the recombinant *E. coli* microorganism comprises nucleotide sequences encoding an SHC enzyme or enzyme variant (e.g. the microorganism comprises a nucleotide sequence selected from SEQ ID NO: 2, 4, 6, 8, 10, 12, and 14).

Preferably, the recombinant *E. coli* microorganism comprises a vector construct as described herein. In another preferred embodiment, the recombinant *E. coli* microorganism comprises nucleotide sequences encoding the SHC enzymes and or enzyme variant disclosed herein.

Another preferred host cell to use with the present disclosure is *S. cerevisiae*. There are libraries of mutants, plasmids, detailed computer models of metabolism and other information available for *S. cerevisiae*, allowing for rational design of various modules to enhance product yield. Methods are known for making recombinant *S. cerevisiae* microorganisms.

Culturing of cells may be performed in a conventional manner. The culture medium may contain a carbon source, at least one nitrogen source and inorganic salts, and vitamins are added to it. The constituents of this medium can be the ones which are conventionally used for culturing the species of microorganism in question. Carbon sources of use in the instant method include any molecule that can be metabolized by the recombinant host cell to facilitate growth and/or production of the SHC enzyme of interest for the conversion of a compound of formula (II) to the compound of formula (I). Examples of suitable carbon sources include, but are not limited to, sucrose (e.g. as found in molasses), fructose, xylose, glycerol, glucose, cellulose, starch, cellobiose or other glucose containing polymer.

In embodiments employing yeast as a host, for example, carbon sources such as sucrose, fructose, xylose, ethanol, glycerol, and glucose are suitable. The carbon source can be provided to the host organism throughout the cultivation period in batch or fed-batch, or alternatively, another energy source can be used, like e.g. protein or protein hydrolysate.

The recombinant host cell microorganism for use in the methods of the present disclosure may be propagated in a rich medium (e.g. LB-medium, Bacto-tryptone yeast extract medium, nutrient medium and the like) at a pH, temperature and under reaction conditions commonly used for propagation of the microorganism. In one embodiment of the present disclosure, a defined minimal medium such as M9A is used for cultivation.

The components of M9A medium comprise: 14 g/l $KH_2PO_4$, 16 g/l $K_2HPO_4$, 1 g/l $Na_3Citrate{\cdot}2H_2O$, 7.5 g/l $(NH_4)_2SO_4$, 0.25 g/l $MgSO_4{\cdot}7H_2O$, 0.015 g/l $CaCl_2{\cdot}2H_2O$, 5 g/l glucose and 1.25 g/l yeast extract).

In another embodiment of the present disclosure, nutrient rich medium such as LB was used. The components of LB medium comprise: 10 g/l tryptone, 5 g/l yeast extract, 5 g/l NaCl. Other examples of Mineral Medium and M9 Mineral Medium are disclosed, for example, in U.S. Pat. No. 6,524,831B2 and US 2003/0092143A1.

Another example of a minimal medium may be prepared as follows: for 350 ml culture: to 35 ml citric acid/phosphate stock (133 g/l $KH_2PO_4$, 40 g/l $(NH_4)_2HPO_4$, 17 g/l citric acid$\cdot H_2O$ with pH adjusted to 6.3) was added 307 ml $H_2O$, the pH adjusted to 6.8 with 32% NaOH as required. After autoclaving 0.850 ml 50% $MgSO_4$, 0.035 ml trace elements solution (see below) solution, 0.035 ml Thiamin solution and 7 ml 20% glucose were added.

Trace elements solution: 50 g/l $Na_2EDTA{\cdot}2H_2$, 20 g/l $FeSO_4{\cdot}7H_2O$, 3 g/l $H_3BO_3$, 0.9 g/l $MnSO_4{\cdot}2H_2O$, 1.1 g/l $CoCl_2$, 80 g/L $CuCl_2$, 240 g/l $NiSO_4{\cdot}7H_2O$, 100 g/l KI, 1.4 g/l $(NH_4)_6Mo_7O_{24}{\cdot}4H_2O$, 1 g/l $ZnSO_4{\cdot}7H_2O$, in deionized water Thiamin solution: 2.25 g/l Thiamin·HCl in deionized water $MgSO_4$ solution: 50% (w/v) $MgSO_4{\cdot}7H_2O$ in deionized water The recombinant microorganism may be grown in a batch, fed batch or continuous process or combinations thereof. Typically, the recombinant microorganism is grown in a fermentor at a defined temperature in the presence of a suitable nutrient source. e.g. a carbon source, for a desired period of time to produce sufficient SHC enzyme to be able to convert the compound of formula (II) to the compound of formula (I) and to produce a desired amount of the compound of formula (I). The recombinant host cells may be cultivated in any suitable manner, for example by batch cultivation or fed-batch cultivation.

As used herein, the term "batch cultivation" is a cultivation method in which culture medium is neither added nor withdrawn during the cultivation.

As used herein, the term "fed-batch" means a cultivation method in which culture medium is added during the cultivation but no culture medium is withdrawn.

One embodiment of the present disclosure provides a method of producing the compound of formula (I) in a cellular system comprising producing the SHC enzyme or enzyme variant under suitable conditions in a cellular system, feeding the compound of formula (II) to the cellular system, converting the compound of formula (II) to the compound of formula (I) using the SHC enzymes or enzyme variants produced using the cellular system, collecting the compound of formula (I) from cellular system and optionally isolating the compound of formula (I) from the system. Expression of other nucleotide sequences may serve to enhance the method. The expression of other nucleotide sequences may enhance the activity of the cellular system used in the bioconversion for making the compound of formula (I).

A further embodiment of the present disclosure is a bioconversion method of making the compound of formula (I) comprising growing host cells comprising a gene coding for an SHC enzyme or enzyme variant, producing SHC enzymes or enzyme variants in the host cells, feeding the compound of formula (II) to the host cells, incubating the host cells under conditions of pH, temperature and solubilizing agent suitable to promote the conversion of the compound of formula (II) to the compound of formula (I) and collecting the compound of formula (I). The production of the SHC enzymes or enzyme variants in the host cells provides a method of making the compound of formula (I) when the compound of formula (II) is added to the host cells under suitable reaction conditions. Achieved conversion may be enhanced by adding more biocatalyst and SOS to the reaction mixture.

The recombinant host cell microorganism may be cultured in a number of ways in order to provide cells in suitable amounts that have produced the SHC enzyme or enzyme variant for the subsequent bioconversion step. Since the microorganisms applicable for the bioconversion step vary broadly (e.g. yeasts, bacteria and fungi), culturing conditions are, of course, adjusted to the specific requirements of each species and these conditions are well known and documented. Any of the art known methods for growing cells of recombinant host cell microorganisms may be used to produce the cells utilizable in the subsequent bioconversion step of the present disclosure. Typically the cells are grown to a particular density (measurable as optical density (OD)) to produce a sufficient biomass for the bioconversion reaction.

The cultivation conditions chosen influence not only the amount of cells obtained (the biomass) but the quality of the cultivation conditions also influences how the biomass becomes a biocatalyst. The recombinant host cell microorganism expressing the SHC enzyme or enzyme variant gene and producing the SHC enzyme or enzyme variant is termed a biocatalyst which is suitable for use in a bioconversion reaction. In some embodiments the biocatalyst is a recombinant whole cell producing SHC enzymes or enzyme variants or it may be in suspension or an immobilized format. In other embodiments, the biocatalyst is a membrane fraction or a liquid fraction prepared from the recombinant whole cell producing the SHC enzyme or enzyme variant (as disclosed for example in Seitz et al 2012—as cited above). The recombinant whole cell producing SHC enzymes or enzyme variants include whole cells collected from the fermenter (for the bioconversion reaction) or the cells in the fermenter (which are then used in a one-pot reaction). The recombinant whole cell producing SHC enzymes or enzyme variants can include intact recombinant whole cell and/or cell debris. Either way, the SHC enzyme or enzyme variant is associated with a membrane (such as a cell membrane) in some way in order to receive and/or interact with a substrate (e.g. compound of formula (II)), which membrane (such as a cell membrane) can be part of a whole cell (e.g. a recombinant whole cell). The SHC enzymes or enzyme variants may also be in an immobilized form (e.g. associated with an enzyme carrier) which allows the SHC enzymes or enzyme variants to interact with a substrate (e.g. compound of formula (II)). The SHC enzymes or enzyme variants may also be used in a soluble form.

In one embodiment, the biocatalyst is produced in sufficient amounts (to create a sufficient biomass), harvested and washed (and optionally stored (e.g. frozen or lyophilized)) before the bioconversion step.

In a further embodiment, the cells are produced in sufficient amounts (to create a sufficient biocatalyst) and the reaction conditions are then adjusted without the need to harvest and wash the biocatalyst for the bioconversion reaction. This one step (or "one pot") method is advantageous as it simplifies the process. The culture medium used to grow the cells is also suitable for use in the bioconversion reaction provided that the reaction conditions are adjusted to facilitate the bioconversion reaction.

The optimum pH for growing the cells is in the range of 6.0-8.0. The optimum pH for the bioconversion reaction is dependent on the type of SHC enzyme or enzyme variant used in the bioconversion reaction. The pH is regulated using techniques which are well known to the skilled person.

The bioconversion methods of the present disclosure are carried out under conditions of time, temperature, pH and solubilizing agent to provide for conversion of the compound of formula (II) to the compound of formula (I).

The pH of the reaction mixture may be in the range of 4-8, preferably, 4.5 to 6.5, more preferably 4.5-6.5 for the SHC wild-type enzyme or SHC enzyme variant considered and can be maintained by the addition of buffers to the reaction mixture. An exemplary buffer for this purpose is a citric acid buffer, or a succinic acid buffer.

The temperature is between from about 15° C. to about 60° C., for example from about 15° C. to about 50° C. or from about 15° C. to about 45° C. or from about 30° C. to about 60'C or from about 35° C. to about 55° C. for the SHC wild-type enzyme or SHC enzyme variant considered. The temperature can be kept constant or can be altered during the bioconversion process.

The [SDS]/[cells] ratio may be in the range of about, 10:1-20:1, preferably about 15:1-18:1, preferably about 16:1 when the ratio of biocatalyst to compound of formula (II) is about 2:1.

The processes for making the compound of formula (I) disclosed herein may be carried out at the optimum temperature, pH and surfactant concentration enabling optimal activity of each of the individual SHC enzyme (wild-type or variant) considered.

It may be useful to include a solubilizing agent (e.g. a surfactant, detergent, solubility enhancer, water miscible organic solvent and the like) in the bioconversion reaction.

As used herein, the term "surfactant" means a component that lowers the surface tension (or interfacial tension) between two liquids or between a liquid and a solid.

Surfactants may act as detergents, wetting agents, emulsifiers, foaming agents, and dispersants. Examples of surfactants include but are not limited to Triton X-100. Tween 80, taurodeoxycholate, Sodium taurodeoxycholate, Sodium dodecyl sulfate (SDS), and/or sodium lauryl sulfate (SLS).

Whilst Triton X-100 may be used to partially purify the SHC enzyme or enzyme variant (in soluble or membrane fraction/suspension form), it may also be used in the bioconversion reaction (see for example the disclosure in Seitz (2012 PhD thesis as cited above) as well as the disclosure in Neumann and Simon (1986—as cited above) and JP2009060799. SDS may be used as a solubilizing agent.

Without wishing to be bound by theory, the use of SDS with recombinant microbial host cells may be advantageous as the SDS may interact advantageously with the host cell membrane in order to make the SHC enzyme or enzyme variant (which is a membrane bound enzyme) more accessible to the compound of formula (II) substrate. In addition, the inclusion of SDS at a suitable level in the reaction mixture may improve the properties of the emulsion (e.g. compound of formula (II) in water) and/or improve the access of the compound of formula (II) substrate to the SHC enzyme within the host. The concentration of the solubilising agent (e.g. SDS) used in the bioconversion reaction is influenced by the biomass amount and the substrate concentration. That is, there is a degree of interdependency between the solubilising agent (e.g. SDS) concentration, the biomass amount and the substrate concentration. By way of example, as the concentration of compound of formula (II) substrate increases, sufficient amounts of biocatalyst and solubilising agent (e.g. SDS) are required for an efficient bioconversion reaction to take place. If, for example, the solubilising agent (e.g. SDS) concentration is too low, a suboptimal conversion of compound of formula (II) may be observed. On the other hand, if, for example, the solubilising agent (e.g. SDS) concentration is too high, then there may be a risk that the biocatalyst is affected through either the disruption of the intact microbial cell and/or denaturation/inactivation of the SHC enzyme or enzyme variant. The selection of a suitable concentration of SDS in the context of the biomass amount and, substrate must be carefully investigated.

In some embodiments, the compound of formula (I) is produced using a biocatalyst to which the compound of formula (II) substrate is added.

It is possible to add the substrate by feeding using known means (e.g. peristaltic pump, infusion syringe and the like). The compound of formula (II) may be oil soluble and provided in an oil format. Given that the biocatalyst (microbial cells such as intact recombinant whole cell and/or cell debris and/or immobilised enzyme) is present in an aqueous phase, the bioconversion reaction may be regarded as a three phase system (comprising an aqueous phase, a solid phase and an oil phase) when compound of formula (II) is added to the bioconversion reaction mixture. This is the case even when SDS is present.

A fermenter may be used to grow recombinant host cells producing the SHC enzyme or enzyme variant gene and producing active SHC enzymes or enzyme variants to a sufficient biomass concentration suitable for use as a biocatalyst in the same fermenter vessel which is used to convert the compound of formula (II) to the compound of formula (I), for example in admixture with one or more of the by-product of formula (III).

The skilled person will understand that higher cumulative production titers can be achieved by implementing a continuous process, such as product removal, substrate feed, and biomass addition or (partial) replacement. Preferably the bioconversion of compound of formula (II) into compound of formula (I) in the presence of a recombinant host cell comprising an SHC enzyme or enzyme variant generates a compound of formula (I) yield of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 58, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, given in mol percent and based on the mols of compound of formula (II) employed, especially preferably, the yield is between 5 and 100, 10 and 100, and 100, 25 and 100, 30 and 100, 35 and 100, in particular between 40 and 100, and 100, 50 and 100, 60 and 100, 70 and 100 mol percent.

The activity of the SHC enzyme or enzyme variant is defined via the reaction rate ((amount of product/(amount of product+amount of remaining starting material))×100) in percent, Preferably, the bioconversion of compound of formula (II) into compound of formula (I) in the presence of an SHC enzyme or enzyme variant produces compound of formula (I) yield of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 48, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 given in mol percent and based on the mols of compound of formula (I) employed; especially preferably, the yield is between 5 and 100, 10 and 100, 20 and 100, 25 and 100, 30 and 100, 35 and 100, in particular between 40 and 100, 45 and 100, 50 and 100, 60 and 100, 70 and 100.

In a preferred embodiment of the invention, the yield and/or the reaction rate are determined over a defined time period of, for example, 4, 6, 8, 10, 12, 16, 20, 24, 36 48, or 72 hours, during which compound of formula (II) is converted into compound of formula (I) by a recombinant host cell comprising a nucleotide sequence encoding an SHC enzyme or enzyme variant, and which has produced the SHC enzyme or enzyme variant.

In a further embodiment, the reaction is carried out under precisely defined conditions of, for example, 25'C, 30° C., 40° C., 50° C. or 60° C. In particular, the yield and/or the reaction rate are determined by carrying out the reaction of converting compound of formula (II) into compound of formula (I) by the SHC enzyme or enzyme variant according to the invention at a temperature range from about 35° C. to about 55° C. over a period of 24-72 hours.

In a further embodiment of the present invention, a recombinant host cell comprising a nucleotide sequence encoding an SHC enzyme variant is characterized in that it shows a 2-, 3-, 4-, 5-, 6-, 7-, 8-, 9-, 10-, 11-, 12-, 13-, 14-, 15-, 16-, 17-, 18-, 19-, 20-, 21-, 22-, 23-, 24-, 25-, 26-, 27-, 28-, 29-, 30-, 31-, 32-, 33-, 34-, 35-, 36-, 37-, 38-, 39-, 40-, 41-, 42-, 43-, 44-, 45-, 46-, 47-, 48-, 49-, 50-, 51-, 52-, 53-, 54-, 55-, 56-, 57-, 58-, 59-, 60-, 61-, 62-, 63-, 64-, 65-, 66-, 67-, 68-, 69-, 70-, 71-, 72-, 73-, 74-, 75-, 76-, 77-, 78-, 79-, 80-, 81-, 82-, 83-, 84-, 85-, 86-, 87-, 88-, 89-, 90-, 91-, 92-, 93-, 94-, 95-, 96-, 97-, 98-, 99-, 100-, 200-, 500-, 1000-fold or higher yield and/or reaction rates in the reaction of compound of formula (II) to give compound of formula (I) in comparison with the parent wild-type or variant SHC enzyme under the same conditions, preferably under conditions that have been individually defined as being optimal for the activity of the SHC enzyme considered Here, the term condition relates but are not limited to reaction conditions such as e.g., pH, temperature and concentration of solubilizing agent (e.g. SDS).

The successful development of a bioconversion process for making compound of formula (I) from compound of formula (II) in a recombinant strain of *E. coli* comprising a nucleotide sequence encoding a wild-type/reference SHC or a SHC variant can offer a low cost and industrially economical process for compound of formula (I) production.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. The term "comprising" also means "including" as well as "consisting" e.g. a composition "comprising" X may consist exclusively of X or may include something additional e.g. X+Y. It must be noted also that, as used in this specification and the appended claims, the singular forms "a". "an" and "the" include plural referents unless the content clearly dictates otherwise. By way of example, a reference to "a gene" or "an enzyme" is a reference to "one or more genes" or "one or more enzymes".

It is to be understood that this disclosure is not limited to the particular methodology, protocols and reagents described herein as these may vary. It is also to be understood that the terminology used herein is for the purpose of describing particular embodiments only, and is not intended to limit the scope of the present disclosure which will be limited only by the appended claims. Unless defined otherwise, all technical and scientific terms used herein have the same meanings as commonly understood by the person skilled in the art. In accordance with the present disclosure there may be conventional molecular biology, microbiology, and recombinant DNA techniques employed which are within the skill of the art.

This disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting. Preferably, the terms used herein are defined as described in "A multilingual glossary of biotechnological terms: (IUPAC Recommendations)", Leuenberger, H. G. W, Nagel, B. and Kolbi, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions. GenBank Accession Number sequence submissions etc.), whether supra or infra, is hereby incorporated by reference in its entirety.

The examples described herein are illustrative of the present disclosure and are not intended to be limitations thereon. Different embodiments of the present disclosure have been described according to the present disclosure. Many modifications and variations may be made to the techniques described and illustrated herein without departing from the spirit and scope of the disclosure. Accordingly, it should be understood that the examples are illustrative only and are not limiting upon the scope of the disclosure.

EXAMPLES

Example 1—Production of SHC Enzyme

SHC Plasmid Preparation:

The gene encoding a wild-type or variant squalene hopene cyclase (SHC) enzyme was inserted into plasmid pET-28a (+), where it is under the control of an IPTG inducible T7-promotor for protein production in *Escherichia coli*. The plasmid was transformed into *E. coli* strain BL21(DE3) using a standard heat-shock transformation protocol, Media Preparation:

The minimal medium chosen as default was prepared as follows for 350 ml culture: to 35 ml citric acid/phosphate stock (133 g/l $KH_2PO_4$, 40 g/l $(NH_4)_2HPO_4$, 17 g/l citric acid-$H_2O$ with pH adjusted to 6.3) was added 307 ml $H_2O$, the pH adjusted to 6.8 with 32% NaOH as required. After autoclaving 0.850 ml 50% $MgSO_4$, 0.035 ml trace elements solution (see below), 0.035 ml Thiamin solution and 7 ml 20% glucose were added.

Trace elements solution: 50 g/l $Na_2EDTA \cdot 2H_2O$, 20 g/l $FeSO_4 \cdot 7H_2O$, 3 g/l $H_3BO_3$, 0.9 g/l $MnSO_4 \cdot 2H_2O$, 1.1 g/l $CoCl_2$, 80 g/L $CuCl_2$, 240 g/l $NiSO_4 \cdot 7H_2O$, 100 g/l KI, 1.4 g/l $(NH_4)_6Mo_7O_{24} \cdot 4H_2O$, 1 g/l $ZnSO_4 \cdot 7H_2O$, in deionized water.

Thiamin solution: 2.25 g/l Thiamin·HCl in deionized water.

$MgSO_4$ solution: 50% (w/v) $MgSO_4 \cdot 7H_2O$ in deionized water.

SHC Enzyme or Enzyme Variant Production (Biocatalyst Production).

Small Scale Biocatalyst Production (Wild-Type SHC or SHC Variants)

350 ml culture (medium supplemented with 50 μg/ml kanamycin) were inoculated from a preculture of the *E. coli* strain BL21(DE3) containing the SHC production plasmid. Cells were grown to an optical density of approximately 0.5 ($OD_{650nm}$) at 37° C. with constant agitation (250 rpm).

Protein production was then induced by the addition of IPTG to a concentration of 300 μM followed by incubation for a further 5-6 hours with constant shaking. The resulting biomass was finally collected by centrifugation and washed with e.g. 50 mM Tris-HCl buffer pH 7.5. The cells were stored as pellets at 4° C. or −20° C. until further use. In general 2.5 to 4 grams of cells (wet weight) were obtained from 1 liter of culture, independently of the medium used.

Biocatalyst Production in Fermenters

Fermentations were prepared and run in 750 ml InforsHT reactors. To the fermentation vessel was added 168 ml deionized water. The reaction vessel was equipped with all required probes ($pO_2$. pH, sampling, antifoam), C+N feed and sodium hydroxide bottles and autoclaved. After autoclaving is added to the reactor 20 ml 10× phosphate/citric acid buffer
14 ml 50% glucose
0.53 ml $MgSO_4$ solution
2 ml $(NH_4)_2SO_4$ solution
0.020 ml trace elements solution
0.400 ml thiamine solution
0.200 ml kanamycin stock The running parameters were set are as follows: pH=6.95, $pO_2$=40%, T=30° C., Stirring at 300 rpm. Cascade: rpm setpoint at 300, min 300, max 1000, flow (l/min) set point 0.1, min 0, max 0.6. Antifoam control: 1:9.

The fermenter was inoculated from a seed culture to an $OD_{650nm}$ of 0.4-0.5. This seed culture was grown in LB medium (+Kanamycin) at 37° C., 220 rpm for 8 h. The fermentation was run first in batch mode for 11.5 h, where after was started the C+ N feed with a feed solution (sterilized glucose solution (143 ml $H_2O$+ 35 g glucose) to which had been added after sterilization: 17.5 ml $(NH_4)_2SO_4$ solution, 1.8 ml $MgSO_4$ solution, 0.018 ml trace elements solution, 0.360 ml Thiamine solution, 0.180 ml kanamycin stock. The feed was run at a constant flow rate of approx. 4.2 ml/h. Glucose and $NH_4^+$ measurements were done externally to evaluate availability of the C- and N-sources in the culture. Usually glucose levels stay very low.

Cultures were grown for a total of approximately 25 hours, where they reached typically an $OD_{850nm}$, of 40-45. SHC production was then started by adding IPTG to a concentration of approx. 1 mM in the fermenter (as IPTG pulse or over a period of 3-4 hours using an infusion syringe), setting the temperature to 40° C. and $pO_2$ to 20%. Induction of SHC production lasted for 16 h at 40° C. At the end of induction the cells were collected by centrifugation, washed with 0.1 M citric acid/sodium citrate buffer pH 5.4 and stored as pellets at 4° C. or −20° C. until further use.

Example 2—GC Analytics

Samples were extracted with an appropriate volume of tert-butylmethyl ether (MBTE/tBME) for quantification of their content in substrate and reaction products. The solvent fraction was separated from the water phase by centrifugation prior to analysis with gas chromatography. 1 μl of the solvent phase was injected (split ratio 10) onto a m×0.32 mm×0.25 μm Zebron ZB-Wax column. The column was developed at constant flow (4 ml/min $H_2$) with the temperature gradient: 100° C. 15° C./min to 200° C., 120° C./min to 240° C. 4 mm at 240° C. Inlet temperature: 250° C., detector temperature. 250° C. This resulted in separation of substrate and product peaks.

Hydroxyfarnesylacetone conversion was calculated from the areas of the peaks corresponding to substrate and reaction products with the following formula:

$$\text{Conversion (\%)}=100\times(\text{Area}_{Product\ Peaks}/(\text{Area}_{Product\ Peaks}+\text{Area}_{Substrate\ Peak(s)}))$$

Figure 2:
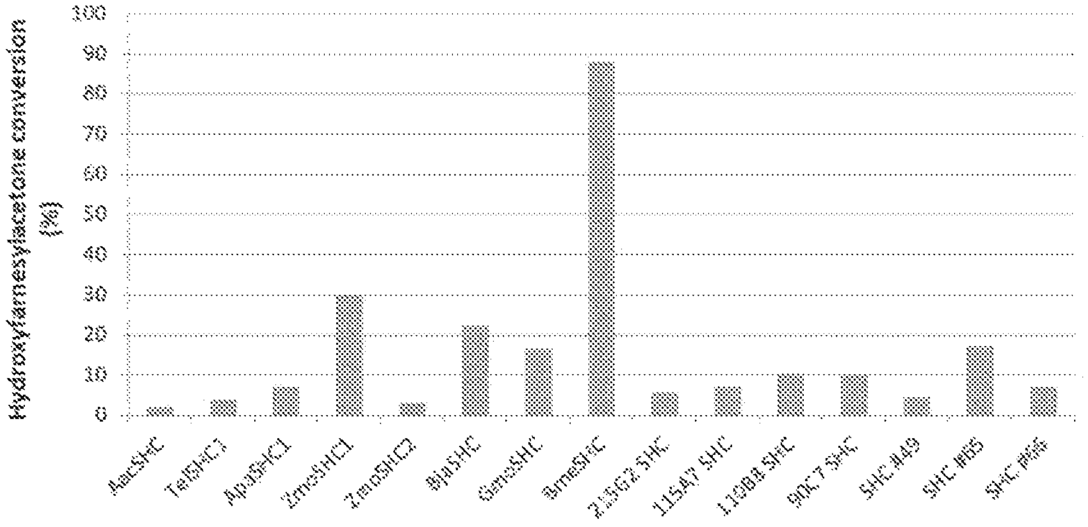
FIG. 2 shows the conversion [%] of Hydroxyfarnesylacetone to (+)-Amberketal with wild type and variant SHC enzymes and gives an overview of the performance of the tested SHC enzymes under their optimal reaction conditions as set out in Table 2.

Example 3—Screening for Hydroxyfarnesylacetone Cyclization with SHC Enzymes and Enzyme Variants A collection of SHC enzymes was produced in *E. coli* as outlined in Example for use in Hydroxyfarnesylacetone cyclization reactions. The reactions contained 1 g/l Hydroxyfarnesylacetone and cells to an $OD_{650nm}$ of 10. Reaction conditions were applied as listed in Table 2. An overview of the performance of the SHC enzymes tested under their optimal reaction conditions as set out in Table 2 is shown in FIG. 2.

TABLE 2

SHC enzymes and reaction conditions.

| SHC enzyme | SEQ ID NO | Temperature (° C.) | pH* | [SDS] (ww %) |
|---|---|---|---|---|
| AacSHC | 1 | 55 | 6.0 | 0.05 |
| TelSHC | 18 | 45 | 6.4 | 0.075 |
| ApaSHC1 | 19 | 45 | 5.2 | 0.075 |
| ZmoSHC1 | 15 | 40 | 5.2 | 0.005 |
| ZmoSHC2 | 16 | 35 | 6.4 | 0.005 |
| BjaSHC | 17 | 50 | 5.8 | 0.005 |
| BmeSHC | 21 | 45 | 5.6 | 00025 |
| GmoSHC | 20 | 40 | 5.6 | 0.0075 |
| 215G2 SHC | 13 | 35 | 5.4 | 0.07 |
| 115A7 SHC | 11 | 35 | 5.4 | 0.05 |
| 110B8SHC | 9 | 35 | 5.8 | 0.05 |
| 90C7 SHC | 7 | 45 | 5.6 | 0.04 |
| SHC #49 | 22 | 45 | 5.6 | 0.05 |
| SHC #65 | 3 | 45 | 5.6 | 0.07 |
| SHC #66 | 5 | 45 | 5.6 | 0.06 |

*in citric acid/soduum phosphate buffer

All enzymes tested were able to cyclize Hydroxyfarnesylacetone to (+)-Amberketal. Conversion with wild-type enzymes was between 2 and approx, 90%, and highest with BmeSHC as outlined in FIG. 2. Hydroxyfarnesylacetone cyclization was increased when mutations were introduced into wild-type AacSHC as observed with SHC variants 215G2 SHC, 115A7 SHC, 11088 SHC, 90C7 SHC, SHC #49, SHC #66, SHC #66 as outlined in FIG. 2.

Example 4—Hydroxyfarnesylacetone Cyclization with SHC Enzymes

With cells that had produced the ZmoSHC1 or the BmeSHC enzyme was tested hydroxyfarnesylacetone cyclization in reactions containing 2 and 8 g/l hydroxyfarnesylacetone, respectively. Reactions contained cells to an $OD_{800nm}$ of 80. Reactions were run in 50 mM succinic acid/NaOH buffer pH 5.2 and incubated for 24 hours at 35° C. GC-FID analysis of the solvent-extracted reactions indicated 52% and 90% hydroxyfarnesylacetone conversion, respectively with ZmoSHC1 and BmeSHC in reactions run at 2 g/l substrate. At 8 g/l hydroxyfarnesylacetone was conversion 17% and 79%, respectively with ZmoSHC1 and BmeSHC.

Example 5—Cyclization of Hydroxyfarnesylacetone with a Squalene Hopene Cyclase Variant Enzyme SHC variant 215G2 was produced as outlined in Example 1 and used in a cyclization reaction of Hydroxyfarnesylacetone.

A typical reaction (150 g total volume) was set up as follows in 0.75 liter Infors fermenters. The reaction vessel was loaded with Hydroxyfarnesylacetone (0.75 g, 2.7 mmol), 1.95 g SOS was added from a 31% (w/w) solution prepared in deionized water. A cell suspension was prepared from *E. coli* cells that had produced the SHC variant of interest by suspending the cells in 0.1 M succinic acid/NaOH buffer pH 5.1. After determination of the cell wet weight concentration of this cell suspension by centrifugation for 10 min at 10° C. and 17210 g, the appropriate volume of cells was added to the reaction vessel in order to introduce 37.5 g of cells into the reaction. The volume of the reaction was completed to 150 g with the required amount of reaction buffer pH 5.1. The reaction was run at 35° C. and pH 5.4 under constant stirring (700 rpm). pH was set to 5.4 using 85% $H_3PO_4$. pH regulation was done manually using 85% phosphoric acid as required. The reaction was sampled over time (1 ml), extracted with 5 volumes of MTBE/tBME (5 ml). The substrate and product content of the reaction was determined by GC analysis after clarification of the solvent phase by centrifugation (table top centrifuge, 13000 rpm, 2 min).

After approx. 72 hours of reaction was the reaction extracted 5 times with 100 ml MTBE by vigorous shaking followed by phase separation by centrifugation (6000 g, 10 min, room temperature). The crude extract was filtered over silica gel and the filtrate was concentrated. The residue (2.4 g) was purified by column chromatography on silica gel, eluting with a gradient of 7-70% ethyl acetate in n-heptane. From this was isolated (+)-Amberketal (compound of formula (I), 173 mg, 23%, slightly yellow solid) and (Z)-5-((5aR,9aR)-6,6,9a-trimethyloctahydrobenzo[b]oxepin-3(2H)-ylidene)pentan-2-one (compound of formula (III). 65 mg, 9%, off-white solid).

Characterization of (+)-Amberketal. $[\alpha]_D^{23}$=+16.4° (c=0.42·$CHCl_3$, TLC (silica gel, heptane/EtOAc 3:2): $R_f$=0.54.

1H-NMR (400 MHz, $CDCl_3$) 4.32 (d, J=6.8 Hz, 1H), 3.37 (dd, J==7.1, 1.2 Hz, 1H), 1.90 (dt, J=127, 3.4 Hz, 1H), 1.82 (dd, J=13.7, 4.6 Hz, 1H), 1.49-1.78 (m, 8H), 1.43-1.47 (m, 1H), 1.42 (s, 3H), 1.10-1.24 (m, 3H), 0.99 (dd, J=12.2, 2.0 Hz, 1H), 0.90 (s, 6H), 0.83-0.95 (m, 1H), 0.82 (s, 3H). $^{13}$C-NMR (101 MHz, $CDCl_3$): 106.0 (s), 82.6 (s), 73.5 (t), 55.7 (d), 53.3 (d), 41.8 (t), 38.7 (t), 37.3 (s), 36.2 (t), 35.9 (t), 33.6 (q), 33.1 (s), 24.3 (q), 21.7 (q), 20.0 (t), 18.3 (t), 17.4 (t), 14.6 (q).

EI-MS (70 eV): 278 (M+, <1), 263 (<1), 248 (2), 236 (4), 218 (36), 203 (19), 190 (55), 175 (43), 162 (11), 147 (24), 137 (34), 121 (42), 109 (47), 95 (34), 79 (38), 69 (36), 55 (42), 43 (100).

Characterization of (Z)-5-((5aR,9aR)-6,6,9a-trimethyloctahydrobenzo[b]oxepin-3(2H)-ylidene)pentan-2-one.

TLC (silica gel, heptane/EtOAc 3:2): $R_f$=0.29.

$^1$H-NMR (600 MHz, BENZENE-$d_6$) δ ppm 5.01 (br t, J=7.3 Hz, 1H), 4.44 (d, J=16.6 Hz, 1H), 4.29 (br d, J=16.2 Hz, 1H), 2.47 (ddd, J=12.4, 7.9, 3.8 Hz, 1H), 2.22 (ddd, J=12.7, 8.6, 4.3 Hz, 1H), 2.08 (q, J=7.2 Hz, 2H), 1.94 (t, J=1.0 Hz, 2H), 1.73-1.62 (m, 3H), 1.61 (s, 3H), 1.49-1.22 (m, 4H), 1.21-1.14 (m, 2H), 1.19 (s, 3H), 0.87 (s, 3H), 0.72 (s, 3H), $^{13}$C-NMR (151 MHz, BENZENE-$d_6$) δ ppm 205.59, 143.75, 120.82, 78.59, 62.81, 55.39, 42.97, 42.28, 41.65, 35.76, 35.38, 33.45, 29.42, 26.21, 21.56, 21.56, 20.89, 19.64.

EI-MS (70 eV): 278 (M+, <1), 260 (<1), 245 (<1), 220 (1), 141 (16), 135 (15), 123 (24), 109 (32), 95 (25), 81 (19), 69 (12), 55 (13), 43 (100).

Example 5A—Cyclization of Hydroxyfarnesylacetone with Wild Type BmeSHC

Wild type BmeSHC was produced as outlined in Example 1 and used in cyclization reactions of Hydroxyfarnesylacetone.

The reactions (4 ml volume) contained 135 g/l Hydroxyfarnesylacetone, 221 g/l cells (wet cell weight), 0.09% SDS, in 0.2 M acetic acid/sodium acetate buffer pH 5.2. The reactions were incubated at 45° C. with constant agitation (650 rpm, Radleys Carousel). One reaction served as a control, was sampled over time, samples extracted with MTBE, the solvent phase clarified by centrifugation (table top centrifuge, 13000 rpm, 2 min). and analyzed by GC analysis for its substrate and product content. Hydroxyfarnesylacetone conversion was complete or almost complete (100%) approx. 50 h after start, expecting approx. 920 mg of (+)-Amberketal.

The pooled reactions were centrifuged (4500 g, 4° C., 15 min). The pellet was recovered and washed 3 times with 20 ml deionized water (vigorous shaking+centrifugation), the aqueous phases discarded. The pellet was finally resuspended in 15 ml deionized water, and extracted 3 times with 15-20 ml MTBE (vigorous shaking+centrifugation). The organic phases were collected and analyzed for their (+)-amberketal content. The pooled organic phases were filtered (silica gel), the solvent evaporated under nitrogen flow yielding approx. 720 mg dry crystalline powder. The residue (720 mg) was purified by column chromatography on silica gel, eluting with a gradient of 6-50% MTBE in n-heptane. Fractions containing pure (+)-Amberketal were pooled and solvent evaporated. 560 mg (+)-Amberketal (compound of formula (I)) was isolated (approx. 61% yield).

Characterization of (+)-Amberketal. $[\alpha]_D^{25}$=+22.6° (c=0.94, $CHCl_3$). TLC (silica gel, n-heptane/MTBE 3:1). $R_f$=0.55. NMR: the spectroscopic data was in agreement with the data shown in Example 5.

Example 6—Hydroxyfarnesylacetone (See Also FIG. 1)

1a) Preparation of (E)-6,10-dimethyl-1-((tetrahydro-2H-pyran-2-yl)oxy)undeca-5,9-dien-2-one (4): To the solution of ethyl 4-(benzyloxy)-3-oxobutanoate (1, 60 g, 0.25 mol, 1 equiv) in ethanol (600 mL) in a 1 L autoclave was added 10% palladium on carbon (6.0 g, 10% w/w) in portions under nitrogen and the mixture was stirred under 3 atm hydrogen for 12 h. The reaction mixture was filtered through a celite bed and washed with a mixture of dichloromethane/ethanol 11. The filtrate was evaporated under vacuum to give a pale yellow residue which was dissolved in dichloromethane (600 mL). To the solution was added 3,4-dihydro-2H-pyran (42.7 g, 0.51 mol, 2 equiv) and PPTS (6.3 g, 0.025 mol: 0.1 equiv), and the mixture was stirred at room temperature for 16 h, then water (500 mL) was added, followed by extraction with dichloromethane (2×200 mL). The combined organic layer was washed with brine, dried over $Na_2SO_4$ and concentrated under vacuum to yield a crude product which was purified by column chromatography over silica gel eluting with ethyl acetate (5-8%) in petrol ether to afford ethyl (E)-5,9-dimethyl-2-(2-((tetrahydro-2H-pyran-2-yl)oxy)acetyl)deca-4,8-dienoate (2) as pale-yellow liquid (45 g, 77%). This product (44 g, 0.19 mol, 1.0 equiv) was dissolved in THF (440 mL) and potassium carbonate (31.6 g, 0.23 mol, 1.2 equiv) was added. The suspension was stirred at room temperature for 1 h, then (E)-1-bromo-3,7-dimethylocta-2,6-diene (geranyl bromide, 37.3 g, 0.172 mol, 0.9 equiv) was added at 0'C and the mixture was allowed to stir at room temperature for 16 h. The mixture was filtered and the filter cake was washed with dichloromethane. The filtrate was concentrated under vacuum to yield ethyl (E)-5,9-dimethyl-2-(2-((tetrahydro-2H-pyran-2-yl)oxy)acetyl) deca-4,8-dienoate (3, 70 g), which was dissolved in ethanol (500 mL). The solution of KOH (35 g) in water (100 mL) was added and the mixture was heated to 80° C. during 2 h. The solution was concentrated under vacuum to yield a residue which was dissolved in dichloromethane (1 L) and washed with water (2×200 mL) and brine. The organic layer was dried over $Na_2SO_4$ and concentrated under vacuum to yield a crude oil which was purified by column chromatography over silica gel using 5-8% ethyl acetate in petrol ether to afford (E)-6,10-dimethyl-1-((tetrahydro-2H-pyran-2-yl)oxy)undeca-5,9-dien-2-one (4.20 g, 36%) as a pale yellow liquid.

1b) Preparation of (3-(2-methyl-1,3-dioxolan-2-yl)propyl)triphenylphosphonium iodide (8). To a solution of 5-Iodopentan-2-one (45 g, 0.21 mol, 1 equiv) in toluene (200 mL) was added triphenyl phosphine (66.8 g, 0.25 mol, 1.2 equiv). The mixture was stirred for 16 h at 120° C., then cooled to room temperature upon which a solid precipitated which was filtered, washed with diethyl ether (100 mL) and dried under vacuum to obtain (4-oxopentyl)triphenylphosphonium iodide (90 g, 90%) as a pale brown solid. This product (40 g, 0.10 mol, 1 equiv.) was suspended in toluene (400 mL) and ethylene glycol (80 mL) and p-toluene sulphonic acid (1 g, 0.0167 mol, 0.16 equiv) were added and the apparatus equipped with a Dean-Stark condenser. The mixture was heated to 130° C. for 12 h, then cooled to room temperature and the toluene layer was decanted. The remaining rubbery residue was dissolved in dichloromethane (500 mL) and washed with water (500 mL) and brine (200 mL).

The organic layer was dried over $Na_2SO_4$ and concentrated under vacuum to yield (3-(2-methyl-1,3-dioxolan-2-yl)propyl)triphenylphosphonium iodide (8, 43 g, 80%) as a pale brown solid.

1c) Preparation of Hydroxyfarnesylacetone: A suspension of (3-(2-methyl-1,3-dioxolan-2-yl)propyl)triphenylphosphonium iodide (52.8 g, 0.10 mol, 2 equiv) in THF (150 mL) was cooled at −78° C. before adding 1.6 M n-BuLi in Hexane (63.8 mL, 0.10 mol, 2 equiv). The mixture was stirred at room temperature for 30 min, upon which an orange yellow suspension was formed, which was cooled again to −78° C. A solution of (E)-6,10-dimethyl-1-((tetrahydro-2H-pyran-2-yl)oxy)undeca-5,9-dien-2-one (4, 15 g, 0.05 mol, 1 equiv) in THF (20 mL) was added dropwise and stirring was continued at room temperature for 2 h. During this period, the reaction mixture turned into a yellow suspension. The reaction mixture was quenched with ice water (100 mL) and extracted with ethyl acetate (2×100 mL). The organic layer was dried over $Na_2SO_4$ and concentrated under vacuum to yield a crude which was triturated with hexane (4×50 mL) and the precipitated triphenyl phosphine oxide was removed by filtration. After removal of the solvent in vacuuo 2-(((2Z,5E)-6,10-dimethyl-2-(3-(2-methyl-1,3-dioxolan-2-yl)propylidene)undeca-5,9-dien-1-yl)oxy)tetrahydro-2H-pyran (9, 22 g) was obtained as a pale yellow liquid, which, according to 1H-NMR, contained still traces of triphenyl phosphine oxide. The product (22 g, 0.05 mol, 1 equiv.) was dissolved in acetone (200 mL) and 1.5 N aqueous HCl-solution (220 mL) was added at 0° C. The solution was stirred at room temperature for 16 h, then water (50 mL) was added and the mixture was extracted with diethyl ether (2×100 mL). The combined organic layer was washed with brine, dried over $Na_2SO_4$ and concentrated under vacuum to afford a crude oil which was purified by column chromatography over silica gel eluting with 10-15% ethyl acetate in petrolether to yield (5Z,9E)-6-(hydroxymethyl)-10,14-dimethylpentadeca-5,9,13-trien-2-one (Hydroxyfarnesylacetone, 7.5 g, 81% purity by GC/MS), from which a volatile impurity was removed by distillation at 85'C/1 mm/Hg. The residue (5.8 g) was submitted to a second column chromatography over silica gel eluting with 10-15% ethyl acetate in petrolether to yield Hydroxyfarnesylacetone (2.8 g, 19%) as a pale yellow liquid.

$^{13}C$-NMR ($d_6$-DMSO, 100 MHz): 208.4 (s), 140.2 (s), 134.7 (s), 131.1 (s), 125.0 (d), 124.6 (d), 124.6 (d), 58.5 (t), 43.6 (t), 39.7 (2t), 35.0 (t), 30.1 (q), 26.7 (t), 25.9 (q), 21.9 (t), 18.0 (q), 16.2 (q).

SEQUENCE LISTING

SEQ ID NO: 1 (amino acid sequence of wild-type *Alicyclobacillus acidocaldarius* SHC (AacSHC))

```
MAEQLVEAPAYARTLDRAVEYLLSCQKDEGYWWGPLLSNVTMEAEYVLLCHILDRVDRDRMEKIRRYLLH
EQREDGTWALYPGGPPDLDTTIEAYVALKYIGMSRDEEPMQKALRFIQSQGGIESSRVFTRMWLALVGEY
PWEKVPMVPPEIMFLGKRMPLNIYEFGSWARATVVALSIVMSRQPVFPLPERARVPELYETDVPPRRRGA
KGGGGWIFDALDRALHGYQKLSVHPFRRAAEIRALDWLLERQAGDGSWGGIQPPWFYALIALKILDMTQH
PAFIKGWEGLELYGVELDYGGWMFQASISPVWDTGLAVLALRAAGLPADHDRLVKAGEWLLDRQITVPGD
WAVKRPNLKPGGFAFQFDNVYYPDVDDTAVVVWALNTLRLPDERRRRDAMTKGFRWIVGMQSSNGGWGAY
DVDNTSDLPNHIPFCDFGEVTDPPSEDVTAHVLECFGSFGYDDAWKVIRRAVEYLKREQKPDGSWFGRWG
VNYLYGTGAVVSALKAVGIDTREPYIQKALDWVEQHQNPDGGWGEDCRSYEDPAYAGKGASTPSQTAWAL
MALIAGGRAESEAARRGVQYLVETQRPDGGWDEPYYTGTGFPGDFYLGYTMYRHVFPTLALGRYKQAIER
R
```

SEQ ID NO: 2 (nucleotide sequence encoding wild-type AacSHC)

```
ATGGCTGAGCAGTTGGTGGAAGCGCCGGCCTACGCGCGGACGCTGGATCGCGCGGTGGAGTATCTCCTCT
CCTGCCAAAAGGACGAAGGCTACTGGTGGGGGCCGCTTCTGAGCAACGTCACGATGGAAGCGGAGTACGT
CCTCTTGTGCCACATTCTCGATCGCGTCGATCGGGATCGCATGGAGAAGATCCGGCGGTACCTGTTGCAC
GAGCAGCGCGAGGACGGCACGTGGGCCCTGTACCCGGGTGGGCCGCCGGACCTCGACACGACCATCGAGG
CGTACGTCGCGCTCAAGTATATCGGCATGTCGCGCGACGAGGAGCCGATGCAGAAGGCGCTCCGGTTCAT
TCAGAGCCAGGGCGGGATCGAGTCGTCGCGCGTGTTCACGCGGATGTGGCTGGCGCTGGTGGGAGAATAT
CCGTGGGAGAAGGTGCCCATGGTCCCGCCGGAGATCATGTTCCTCGGCAAGCGCATGCCGCTCAACATCT
ACGAGTTTGGCTCGTGGGCTCGGGCGACCGTCGTGGCGCTCTCGATTGTGATGAGCCGCCAGCCGGTGTT
CCCGCTGCCCGAGCGGGCGCGCGTGCCCGAGCTGTACGAGACCGACGTGCCTCCGCGCCGGCGCGGTGCC
AAGGGAGGGGGTGGGTGGATCTTCGACGCGCTCGACCGGGCGCTGCACGGGTATCAGAAGCTGTCGGTGC
ACCCGTTCCGCCGCGCGGCCGAGATCCGCGCCTTGGACTGGTTGCTCGAGCGCCAGGCCGGAGACGGCAG
CTGGGGCGGGATTCAGCCGCCTTGGTTTTACGCGCTCATCGCGCTCAAGATTCTCGACATGACGCAGCAT
CCGGCGTTCATCAAGGGCTGGGAAGGTCTAGAGCTGTACGGCGTGGAGCTGGATTACGGAGGATGGATGT
TTCAGGCTTCCATCTCGCCGGTGTGGGACACGGGCCTCGCCGTGCTCGCGCTGCGCGCTGCGGGGCTTCC
GGCCGATCACGACCGCTTGGTCAAGGCGGGCGAGTGGCTGTTGGACCGGCAGATCACGGTTCCGGGCGAC
TGGGCGGTGAAGCGCCCGAACCTCAAGCCGGGCGGGTTCGCGTTCCAGTTCGACAACGTGTACTACCCGG
ACGTGGACGACACGGCCGTCGTGGTGTGGGCGCTCAACACCCTGCGCTTGCCGGACGAGCGCCGCAGGCG
GGACGCCATGACGAAGGGATTCCGCTGGATTGTCGGCATGCAGAGCTCGAACGGCGGTTGGGGCGCCTAC
GACGTCGACAACACGAGCGATCTCCCGAACCACATCCCGTTCTGCGACTTCGGCGAAGTGACCGATCCGC
CGTCAGAGGACGTCACCGCCCACGTGCTCGAGTGTTTCGGCAGCTTCGGGTACGATGACGCCTGGAAGGT
CATCCGGCGCGCGGTGGAATATCTCAAGCGGGAGCAGAAGCCGGACGGCAGCTGGTTCGGTCGTTGGGGC
GTCAATTACCTCTACGGCACGGGCGCGGTGGTGTCGGCGCTGAAGGCGGTCGGGATCGACACGCGCGAGC
CGTACATTCAAAAGGCGCTCGACTGGGTCGAGCAGCATCAGAACCCGGACGGCGGCTGGGGCGAGGACTG
CCGCTCGTACGAGGATCCGGCGTACGCGGGTAAGGGCGCGAGCACCCCGTCGCAGACGGCCTGGGCGCTG
ATGGCGCTCATCGCGGGCGGCAGGGCGGAGTCCGAGGCCGCGCGCCGCGGCGTGCAATACCTCGTGGAGA
CGCAGCGCCCGGACGGCGGCTGGGATGAGCCGTACTACACCGGCACGGGCTTCCCAGGGGATTTCTACCT
CGGCTACACCATGTACCGCCACGTGTTTCCGACGCTCGCGCTCGGCCGCTACAAGCAAGCCATCGAGCGC
AGGTGA
```

SEQ ID NO: 3 (amino acid sequence of AacSHC enzyme variant #65)

```
MAEQLVEAPAYARTLDRAVEYLLSCQKDEGYWWGPLLSNVTMEAEYVLLCHILDRVDRDRMEKIRRYLLH
EQREDGTWALYPGGPPDLDTTIEAYVALKYIGMSRDEEPMQKALRFIQSQGGIESSRVFTRRWLALVGEY
PWEKVPMVPPEIMFLGKRMPLNIYEFGSWARATVVALSIVMSRQPVFPLPERARVPELYETDVPPRRRGA
KGGGGWIFDALDRVLHGYQKLSVHPFRRAAEIRALDWLLERQAGDGSWGGIQPPWFYALIALKILDMTQH
PAFIKGWEGLELYGVELDYGGWMFQASISPVWDTGLAVLALRAAGLPADHDRLVKAGEWLLDRQITVPGD
WAVKRPNLKPGGFAFQFDNVYYPDVDDTAVVVWALNTLRLPDERRRRDAMTKGFRWIVGMQSSNGGWGAY
DVDNTSDLPNHTPFCDFGEVTDPPSEDVTAHVLECFGSFGYDDAWKVIRRAVEYLKREQKPDGSWFGRWG
VNYLYGTGAVVSALKAVGIDTREPYIQKALDWVEQHQNPDGGWGEDCRSYEDPAYAGKGASTPSQTTWAL
MALIAGGRAESEAARRGVQYLVETQRPDGGWDEPYYTGTGFPGDFYLGYTMYSHVFPTLALGRYKQAIER
R
```

SEQ ID NO: 4 (nucleotide sequence encoding SHC enzyme variant #65)

```
ATGGCTGAGCAGTTGGTGGAAGCTCCGGCCTACGCGCGGACGCTGGATCGCGCGGTGGAGTATCTCCTCT
CCTGCCAAAAGGACGAAGGCTACTGGTGGGGGCCGCTTCTGAGCAACGTCACGATGGAAGCGGAGTACGT
```

-continued

SEQUENCE LISTING

CCTCTTGTGCCACATTCTCGATCGCGTCGATCGGGATCGCATGGAGAAGATCCGGCGGTACCTGTTGCAC
GAGCAGCGCGAGGACGGCACGTGGGCCCTGTACCCGGGTGGGCCGCCGGACCTCGACACGACCATCGAGG
CGTACGTCGCGCTCAAGTATATCGGCATGTCGCGCGACGAGGAGCCGATGCAGAAGGCGCTCCGGTTCAT
TCAGAGCCAGGGCGGGATCGAGTCGTCGCGCGTGTTCACGCGGAGGTGGCTGGCGCTGGTGGGAGAATAT
CCGTGGGAGAAGGTGCCCATGGTCCCGCCGGAGATCATGTTCCTCGGCAAGCGCATGCCGCTCAACATCT
ACGAGTTTGGCTCGTGGGCTCGGGCGACCGTCGTGGCGCTCTCGATTGTGATGAGCCGCCAGCCGGTGTT
CCCGCTGCCCGAGCGGGCGCGCGTGCCCGAGCTGTACGAGACCGACGTGCCTCCGCGCCGGCGCGGTGCC
AAGGGAGGGGGTGGGTGGATCTTCGACGCGCTCGACCGGGTGCTGCACGGGTATCAGAAGCTGTCGGTGC
ACCCGTTCCGCCGCGCGGCCGAGATCCGCGCCTTGGACTGGTTGCTCGAGCGCCAGGCCGGAGACGGCAG
CTGGGGCGGGATTCAGCCGCCTTGGTTTTACGCGCTCATCGCGCTCAAGATTCTCGACATGACGCAGCAT
CCGGCGTTCATCAAGGGCTGGGAAGGTCTAGAGCTGTACGGCGTGGAGCTGGATTACGGAGGATGGATGT
TTCAGGCTTCCATCTCGCCGGTGTGGGACACGGGCCTCGCCGTGCTCGCGCTGCGCGCTGCGGGGCTTCC
GGCCGATCACGACCGCTTGGTCAAGGCGGGCGAGTGGCTGTTGGACCGGCAGATCACGGTTCCGGGCGAC
TGGGCGGTGAAGCGCCCGAACCTCAAGCCGGGCGGGTTCGCGTTCCAGTTCGACAACGTGTACTACCCGG
ACGTGGACGACACGGCCGTCGTGGTGTGGGCGCTCAACACCCTGCGCTTGCCGGACGAGCGCCGCAGGCG
GGACGCCATGACGAAGGGATTCCGCTGGATTGTCGGCATGCAGAGCTCGAACGGCGGTTGGGGCGCCTAC
GACGTCGACAACACGAGCGATCTCCCGAACCACACCCCGTTCTGCGACTTCGGCGAAGTGACCGATCCGC
CGTCAGAGGACGTCACCGCCCACGTGCTCGAGTGTTTCGGCAGCTTCGGGTACGATGACGCCTGGAAGGT
CATCCGGCGCGCGGTGGAATATCTCAAGCGGGAGCAGAAGCCGGACGGCAGCTGGTTCGGTCGTTGGGGC
GTCAATTACCTCTACGGCACGGGCGCGGTGGTGTCGGCGCTGAAGGCGGTCGGGATCGACACGCGCGAGC
CGTACATTCAAAAGGCGCTCGACTGGGTCGAGCAGCATCAGAACCCGGACGGCGGCTGGGGCGAGGACTG
CCGCTCGTACGAGGATCCGGCGTACGCGGGTAAGGGCGCGAGCACCCCGTCGCAGACGACCTGGGCGCTG
ATGGCGCTCATCGCGGGCGGCAGGGCGGAGTCCGAGGCCGCGCGCCGCGGCGTGCAATACCTCGTGGAGA
CGCAGCGCCCGGACGGCGGCTGGGATGAGCCGTACTACACCGGCACGGGCTTCCCAGGGGATTTCTACCT
CGGCTACACCATGTACAGCCACGTGTTTCCGACGCTCGCGCTCGGCCGCTACAAGCAAGCCATCGAGCGC
AGGTGA

SEQ ID NO: 5 (amino acid sequence of AacSHC enzyme variant #66)
MAEQLVEAPAYARTLDRAVEYLLSCQKDEGYWWGPLLSNVTMEAEYVLLCHILDRVDRDRMEKIRRYLLH
EQREDGTWALHPGGPPDLDTTIEAYVALKYIGMSRDEEPMQKALRFIQSQGGIESSRVFTRRWLALVGEY
PWEKVPMVPPEIMFLGKRMPLNIYEFGSWARATVVALSIVMSRQPVFPLPERARVPELYETDVPPRRRGA
KGGGGWIFDALDRVLHGYQKLSVHPFRRAAEIRALDWLLERQAGDGSWGGIQPPWFYALIALKILDMTQH
PAFIKGWEGLELYGVELDYGGWMFQASISPVWDTGLAVLALRAAGLPADHDRLVKAGEWLLDRQITVPGD
WAVKRPNLKPGGFAFQFDNVYYPDVDDTAVVVWALNTLRLPDERRRRDAMTKGFRWIVGMQSSNGGWGAY
DVDNTSDLPNHTPFCDFGEVTDPPSEDVTAHVLECFGSFGYDDAWKVIRRAVEYLKREQKPDGSWFGRWG
VNYLYGTGAVVSALKAVGIDTREPYIQKALDWVEQHQNPDGGWGEDCRSYEDPAYAGKGASTPSQTTWAL
MALIAGGRAESEAARRGVQYLVETQRPDGGWDEPYYTGTGFPGDFYLGYTMYSHVFPTLALGRYKQAIER
R SEQ ID NO: 6 (nucleotide sequence encoding SHC enzyme variant #66)
ATGGCTGAGCAGTTGGTGGAAGCTCCGGCCTACGCGCGGACGCTGGATCGCGCGGTGGAGTATCTCCTCT
CCTGCCAAAAGGACGAAGGCTACTGGTGGGGGCCGCTTCTGAGCAACGTCACGATGGAAGCGGAGTACGT
CCTCTTGTGCCACATTCTCGATCGCGTCGATCGGGATCGCATGGAGAAGATCCGGCGGTACCTGTTGCAC
GAGCAGCGCGAGGACGGCACGTGGGCCCTGCACCCGGGTGGGCCGCCGGACCTCGACACGACCATCGAGG
CGTACGTCGCGCTCAAGTATATCGGCATGTCGCGCGACGAGGAGCCGATGCAGAAGGCGCTCCGGTTCAT
TCAGAGCCAGGGCGGGATCGAGTCGTCGCGCGTGTTCACGCGGAGGTGGCTGGCGCTGGTGGGAGAATAT
CCGTGGGAGAAGGTGCCCATGGTCCCGCCGGAGATCATGTTCCTCGGCAAGCGCATGCCGCTCAACATCT
ACGAGTTTGGCTCGTGGGCTCGGGCGACCGTCGTGGCGCTCTCGATTGTGATGAGCCGCCAGCCGGTGTT
CCCGCTGCCCGAGCGGGCGCGCGTGCCCGAGCTGTACGAGACCGACGTGCCTCCGCGCCGGCGCGGTGCC
AAGGGAGGGGGTGGGTGGATCTTCGACGCGCTCGACCGGGTGCTGCACGGGTATCAGAAGCTGTCGGTGC
ACCCGTTCCGCCGCGCGGCCGAGATCCGCGCCTTGGACTGGTTGCTCGAGCGCCAGGCCGGAGACGGCAG
CTGGGGCGGGATTCAGCCGCCTTGGTTTTACGCGCTCATCGCGCTCAAGATTCTCGACATGACGCAGCAT
CCGGCGTTCATCAAGGGCTGGGAAGGTCTAGAGCTGTACGGCGTGGAGCTGGATTACGGAGGATGGATGT
TTCAGGCTTCCATCTCGCCGGTGTGGGACACGGGCCTCGCCGTGCTCGCGCTGCGCGCTGCGGGGCTTCC
GGCCGATCACGACCGCTTGGTCAAGGCGGGCGAGTGGCTGTTGGACCGGCAGATCACGGTTCCGGGCGAC
TGGGCGGTGAAGCGCCCGAACCTCAAGCCGGGCGGGTTCGCGTTCCAGTTCGACAACGTGTACTACCCGG
ACGTGGACGACACGGCCGTCGTGGTGTGGGCGCTCAACACCCTGCGCTTGCCGGACGAGCGCCGCAGGCG
GGACGCCATGACGAAGGGATTCCGCTGGATTGTCGGCATGCAGAGCTCGAACGGCGGTTGGGGCGCCTAC
GACGTCGACAACACGAGCGATCTCCCGAACCACACCCCGTTCTGCGACTTCGGCGAAGTGACCGATCCGC
CGTCAGAGGACGTCACCGCCCACGTGCTCGAGTGTTTCGGCAGCTTCGGGTACGATGACGCCTGGAAGGT
CATCCGGCGCGCGGTGGAATATCTCAAGCGGGAGCAGAAGCCGGACGGCAGCTGGTTCGGTCGTTGGGGC
GTCAATTACCTCTACGGCACGGGCGCGGTGGTGTCGGCGCTGAAGGCGGTCGGGATCGACACGCGCGAGC
CGTACATTCAAAAGGCGCTCGACTGGGTCGAGCAGCATCAGAACCCGGACGGCGGCTGGGGCGAGGACTG
CCGCTCGTACGAGGATCCGGCGTACGCGGGTAAGGGCGCGAGCACCCCGTCGCAGACGACCTGGGCGCTG
ATGGCGCTCATCGCGGGCGGCAGGGCGGAGTCCGAGGCCGCGCGCCGCGGCGTGCAATACCTCGTGGAGA
CGCAGCGCCCGGACGGCGGCTGGGATGAGCCGTACTACACCGGCACGGGCTTCCCAGGGGATTTCTACCT
CGGCTACACCATGTACAGCCACGTGTTTCCGACGCTCGCGCTCGGCCGCTACAAGCAAGCCATCGAGCGC
AGGTGA SEQ ID NO: 7 (amino acid sequence of AacSHC enzyme variant #90C7)
MAEQLVEAPAYARTLDRAVEYLLSCQKDEGYWWGPLLSNVTMEAEYVLLCHILDRVDRDRMEKIRRYLLH
EQREDGTWALYPGGPPDLDATIEAYVALKYIGMSRDEEPMQKALRFIQSQGGIESSRVFTRRWLALVGEY
PWEKVPMVPPEIMFLGKRMPLNIYEFGSWARATVVALSIVMSRQPVFPLPERARVPELYETDVPPRRRGA
KGGGGWIFDALDRVLHGYQKLSVHPFRRAAEIRALDWLLERQAGDGSWGGIQPPWFYALIALKILDMTQH
PAFIKGWEGLELYGVELDYGGWMFQASISPVWDTGLAVLALRAAGLPADHDRLVKAGEWLLDRQITVPGD
WAVKRPNLKPGGFAFQFDNVYYPDVDDTAVVVWALNTLRLPDERRRRDAMTKGFRWIVGMQSSNGGWGAY
DVDNTSDLPNHTPFCDFGEVTDPPSEDVTAHVLECFGSFGYDDAWKVIRRAVEYLKREQKPDGSWFGRWG -continued

SEQUENCE LISTING

VNYLYGTGAVVSALKAVGIDTREPYIQKALDWVEQHQNPDGGWGEDCRSYEDPAYAGKGASTPSQTAWAL
MALIAGGRAESEAARRGVQYLVETQRPDGGWDEPYYTGTGFPGDFYLGYTMYSHVFPTLALGRYKQAIER
R

SEQ ID NO: 8 (nucleotide sequence encoding SHC variant #90C7)
ATGGCTGAGCAGTTGGTGGAAGCTCCGGCCTACGCGCGGACGCTGGATCGCGCGGTGGAGTATCTCCTCT
CCTGCCAAAAGGACGAAGGCTACTGGTGGGGCCCGCTTCTGAGCAACGTCACGATGGAAGCGGAGTACGT
CCTCTTGTGCCACATTCTCGATCGCGTCGATCGGGATCGCATGGAGAAGATCCGGCGGTACCTGTTGCAC
GAGCAGCGCGAGGACGGCACGTGGGCCCTGTACCCGGGTGGGCCGCCGGACCTCGACGCGACCATCGAGG
CGTACGTCGCGCTCAAGTATATCGGCATGTCGCGCGACGAGGAGCCGATGCAGAAGGCGCTCCGGTTCAT
TCAGAGCCAGGGCGGGATCGAGTCGTCGCGCGTGTTCACGCGGAGGTGGCTGGCGCTGGTGGGAGAATAT
CCGTGGGAGAAGGTGCCCATGGTCCCGCCGGAGATCATGTTCCTCGGCAAGCGCATGCCGCTCAACATCT
ACGAGTTTGGCTCGTGGGCTCGGGCGACCGTCGTGGCGCTCTCGATTGTGATGAGCCGCCAGCCGGTGTT
CCCGCTGCCCGAGCGGGCGCGCGTGCCCGAGCTGTACGAGACCGACGTGCCTCCGCGCCGGCGCGGTGCC
AAGGGAGGGGGTGGGTGGATCTTCGACGCGCTCGACCGGGTGCTGCACGGGTATCAGAAGCTGTCGGTGC
ACCCGTTCCGCCGCGCGGCCGAGATCCGCGCCTTGGACTGGTTGCTCGAGCGCCAGGCCGGAGACGGCAG
CTGGGGCGGGATTCAGCCGCCTTGGTTTTACGCGCTCATCGCGCTCAAGATTCTCGACATGACGCAGCAT
CCGGCGTTCATCAAGGGCTGGGAAGGTCTAGAGCTGTACGGCGTGGAGCTGGATTACGGAGGATGGATGT
TTCAGGCTTCCATCTCGCCGGTGTGGGACACGGGCCTCGCCGTGCTCGCGCTGCGCGCTGCGGGGCTTCC
GGCCGATCACGACCGCTTGGTCAAGGCGGGCGAGTGGCTGTTGGACCGGCAGATCACGGTTCCGGGCGAC
TGGGCGGTGAAGCGCCCGAACCTCAAGCCGGGCGGGTTCGCGTTCCAGTTCGACAACGTGTACTACCCGG
ACGTGGACGACACGGCCGTCGTGGTGTGGGCGCTCAACACCCTGCGCTTGCCGGACGAGCGCCGCAGGCG
GGACGCCATGACGAAGGGATTCCGCTGGATTGTCGGCATGCAGAGCTCGAACGGCGGTTGGGGCGCCTAC
GACGTCGACAACACGAGCGATCTCCCGAACCACACACCCCGTTCTGCGACTTCGGCGAAGTGACCGATCCGC
CGTCAGAGGACGTCACCGCCCACGTGCTCGAGTGTTTCGGCAGCTTCGGGTACGATGACGCCTGGAAGGT
CATCCGGCGCGCGGTGGAATATCTCAAGCGGGAGCAGAAGCCGGACGGCAGCTGGTTCGGTCGTTGGGGC
GTCAATTACCTCTACGGCACGGGCGCGGTGGTGTCGGCGCTGAAGGCGGTCGGGATCGACACGCGCGAGC
CGTACATTCAAAAGGCGCTCGACTGGGTCGAGCAGCATCAGAACCCGGACGGCGGCTGGGGCGAGGACTG
CCGCTCGTACGAGGATCCGGCGTACGCGGGTAAGGGCGCGAGCACCCCGTCGCAGACGGCCTGGGCGCTG
ATGGCGCTCATCGCGGGCGGCAGGGCGGAGTCCGAGGCCGCGCGCCCGCGGCGTGCAATACCTCGTGGAGA
CGCAGCGCCCGGACGGCGGCTGGGATGAGCCGTACTACACCGGCACGGGCTTCCCAGGGGATTTCTACCT
CGGCTACACCATGTACAGCCACGTGTTTCCGACGCTCGCGCTCGGCCGCTACAAGCAAGCCATCGAGCGC
AGGTGA SEQ ID NO: 9 (amino acid sequence of AacSHC enzyme variant #110B8)
MAEQLVEAPAYARTLDRAVEYLLSCQKDEGYWWGPLLSNVTMEAEYVLLCHILDRVDRDRMEKIRRYLLH
EQREDGTWALHPGGPPDLDTTIEAYVALKYIGMSRDEEPMQKALRFIQSQGGIESSRVFTRRWLALVGEY
PWEKVPMVPPEIMFLGKRMPLNIYEFGSWARATVVALSIVMSRQPVFPLPERARVPELYETDVPPRRRGA
KGGGGWIFDALDRVLHGYQKLSVHPFRRAAEIRALDWLLERQAGDGSWGGIQPPWFYALIALKILDMTQH
PAFIKGWEGLELYGVELDYGGWMFQASISPVWDTGLAVLALRAAGLPADHDRLVKAGEWLLDRQITVPGD
WAVKRPNLKPGGFAFQFDNVYYPDVDDTAVVVWALNTLRLPDERRRRDAMTKGFRWIVGMQSSNGGWGAY
DVDNTSDLPNLTPFCDFGEVTDPPSEDVTAHVLECFGSFGYDDAWKVIRRAVEYLKREQKPDGSWFGRWG
VNYLYGTGAVVSALKAVGIDTREPYIQKALDWVEQHQNPDGGWGEDCRSYEDPAYAGKGASTPSQTTWAL
MALIAGGRAESEAARRGVQYLVETQRPDGGWDEPYYTGTGFPGDFYLGYTMYRHVFPTLALGRYKQAIER
R SEQ ID NO: 10 (nucleotide sequence encoding SHC enzyme variant #110B8)
ATGGCTGAGCAGTTGGTGGAAGCTCCGGCCTACGCGCGGACGCTGGATCGCGCGGTGGAGTATCTCCTCT
CCTGCCAAAAGGACGAAGGCTACTGGTGGGGCCCGCTTCTGAGCAACGTCACGATGGAAGCGGAGTACGT
CCTCTTGTGCCACATTCTCGATCGCGTCGATCGGGATCGCATGGAGAAGATCCGGCGGTACCTGTTGCAC
GAGCAGCGCGAGGACGGCACGTGGGCCCTGCACCCGGGTGGGCCGCCGGACCTCGACACGACCATCGAGG
CGTACGTCGCGCTCAAGTATATCGGCATGTCGCGCGACGAGGAGCCGATGCAGAAGGCGCTCCGGTTCAT
TCAGAGCCAGGGCGGGATCGAGTCGTCGCGCGTGTTCACGCGGAGGTGGCTGGCGCTGGTGGGAGAATAT
CCGTGGGAGAAGGTGCCCATGGTCCCGCCGGAGATCATGTTCCTCGGCAAGCGCATGCCGCTCAACATCT
ACGAGTTTGGCTCGTGGGCTCGGGCGACCGTCGTGGCGCTCTCGATTGTGATGAGCCGCCAGCCGGTGTT
CCCGCTGCCCGAGCGGGCGCGCGTGCCCGAGCTGTACGAGACCGACGTGCCTCCGCGCCGGCGCGGTGCC
AAGGGAGGGGGTGGGTGGATCTTCGACGCGCTCGACCGGGTGCTGCACGGGTATCAGAAGCTGTCGGTGC
ACCCGTTCCGCCGCGCGGCCGAGATCCGCGCCTTGGACTGGTTGCTCGAGCGCCAGGCCGGAGACGGCAG
CTGGGGCGGGATTCAGCCGCCTTGGTTTTACGCGCTCATCGCGCTCAAGATTCTCGACATGACGCAGCAT
CCGGCGTTCATCAAGGGCTGGGAAGGTCTAGAGCTGTACGGCGTGGAGCTGGATTACGGAGGATGGATGT
TTCAGGCTTCCATCTCGCCGGTGTGGGACACGGGCCTCGCCGTGCTCGCGCTGCGCGCTGCGGGGCTTCC
GGCCGATCACGACCGCTTGGTCAAGGCGGGCGAGTGGCTGTTGGACCGGCAGATCACGGTTCCGGGCGAC
TGGGCGGTGAAGCGCCCGAACCTCAAGCCGGGCGGGTTCGCGTTCCAGTTCGACAACGTGTACTACCCGG
ACGTGGACGACACGGCCGTCGTGGTGTGGGCGCTCAACACCCTGCGCTTGCCGGACGAGCGCCGCAGGCG
GGACGCCATGACGAAGGGATTCCGCTGGATTGTCGGCATGCAGAGCTCGAACGGCGGTTGGGGCGCCTAC
GACGTCGACAACACGAGCGATCTCCCGAACCTCACCCCGTTCTGCGACTTCGGCGAAGTGACCGATCCGC
CGTCAGAGGACGTCACCGCCCACGTGCTCGAGTGTTTCGGCAGCTTCGGGTACGATGACGCCTGGAAGGT
CATCCGGCGCGCGGTGGAATATCTCAAGCGGGAGCAGAAGCCGGACGGCAGCTGGTTCGGTCGTTGGGGC
GTCAATTACCTCTACGGCACGGGCGCGGTGGTGTCGGCGCTGAAGGCGGTCGGGATCGACACGCGCGAGC
CGTACATTCAAAAGGCGCTCGACTGGGTCGAGCAGCATCAGAACCCGGACGGCGGCTGGGGCGAGGACTG
CCGCTCGTACGAGGATCCGGCGTACGCGGGTAAGGGCGCGAGCACCCCGTCGCAGACGACCTGGGCGCTG
ATGGCGCTCATCGCGGGCGGCAGGGCGGAGTCCGAGGCCGCGCGCCCGCGGCGTGCAATACCTCGTGGAGA
CGCAGCGCCCGGACGGCGGCTGGGATGAGCCGTACTACACCGGCACGGGCTTCCCAGGGGATTTCTACCT
CGGCTACACCATGTACCGCCACGTGTTTCCGACGCTCGCGCTCGGCCGCTACAAGCAAGCCATCGAGCGC
AGGTGA -continued

SEQUENCE LISTING

SEQ ID NO: 11 (amino acid sequence of AacSHC enzyme variant #115A7)
MAEQLVEAPAYARTLDRAVEYLLSCQKDEGYWWGPLLSNVTMEAEYVLLCHILDRVDRDRMEKIRRYLLH
EQREDGTWALYPGGPPDLDTTIEAYVALKYIGMSRDEEPMQKALRFIQSQGGIESSRVFTRRWLALVGEY
PWEKVPMVPPEIMFLGKRMPLNIYEFGSWARTTVVALSIVMSRQPVFPLPERARVPELYETDVPPRRRGA
KGGGGWIFDALDRVLHGYQKLSVHPFRRAAEIRALDWLLERQAGDGSWGGIQPPWFYALIALKILDKTQH
PAFIKGWEGLELYGVELDYGGWMFQASISPVWDTGLAVLALRAAGLPADHDRLVKAGEWLLDRQITVPGD
WAVKRPNLKPGGFAFQFDNVYYPDVDDTAVVVWALNTLRLPDERRRRDAMTKGFRWIVGMQSSNGGWGAY
DVDNTSDLPNHTPFCDFGEVTDPPSEDVTAHVIECFGSFGYDDAWKVIRRAVEYLKREQKPDGSWFGRWG
VNYLYGTGAVVSALKAVGIDTREPYIQKALDWVEQHQNPDGGWGEDCRSYEDPAYAGKGASTPSQTAWAL
MALIAGGRAESEAARRGVQYLVETQRPDGGWDEPYYTGTGFPGDFYLGYTMYRHVFPTLALGRYKQAIER
R SEQ ID NO: 12 (nucleotide sequence encoding SHC variant #115A7)
ATGGCTGAGCAGTTGGTGGAAGCTCCGGCCTACGCGCGGACGCTGGATCGCGCGGTGGAGTATCTCCTCT
CCTGCCAAAAGGACGAAGGCTACTGGTGGGGCCCGCTTCTGAGCAACGTCACGATGGAAGCGGAGTACGT
CCTCTTGTGCCACATTCTCGATCGCGTCGATCGGGATCGCATGGAGAAGATCCGGCGGTACCTGTTGCAC
GAGCAGCGCGAGGACGGCACGTGGGCCCTGTACCCGGGTGGCCCGCCGGACCTCGACACGACCATCGAGG
CGTACGTCGCGCTCAAGTATATCGGCATGTCGCGCGACGAGGAGCCGATGCAGAAGGCGCTCCGGTTCAT
TCAGAGCCAGGGCGGGATCGAGTCGTCGCGCGTGTTCACGCGGAGGTGGCTGGCGCTGGTGGGAGAATAT
CCGTGGGAGAAGGTGCCCATGGTCCCGCCGGAGATCATGTTCCTCGGCAAGCGCATGCCGCTCAACATCT
ACGAGTTTGGCTCGTGGGCTCGGACGACCGTCGTGGCGCTCTCGATTGTGATGAGCCGCCAGCCGGTGTT
CCCGCTGCCCGAGCGGGCGCGCGTGCCCGAGCTGTACGAGACCGACGTGCCTCCGCGCCGGCGCGGTGCC
AAGGGAGGGGGTGGGTGGATCTTCGACGCGCTCGACCGGGTGCTGCACGGGTATCAGAAGCTGTCGGTGC
ACCCGTTCCGCCGCGCGGCCGAGATCCGCGCCTTGGACTGGTTGCTCGAGCGCCAGGCCGGAGACGGCAG
CTGGGGCGGGATTCAGCCGCCTTGGTTTTACGCGCTCATCGCGCTCAAGATTCTCGACAAGACGCAGCAT
CCGGCGTTCATCAAGGGCTGGGAAGGTCTAGAGCTGTACGGCGTGGAGCTGGATTACGGAGGATGGATGT
TTCAGGCTTCCATCTCGCCGGTGTGGGACACGGGCCTCGCCGTGCTCGCGCTGCGCGCTGCGGGGCTTCC
GGCCGATCACGACCGCTTGGTCAAGGCGGGCGAGTGGCTGTTGGACCGGCAGATCACGGTTCCGGGCGAC
TGGGCGGTGAAGCGCCCGAACCTCAAGCCGGGCGGGTTCGCGTTCCAGTTCGACAACGTGTACTACCCGG
ACGTGGACGACACGGCCGTCGTGGTGTGGGCGCTCAACACCCTGCGCTTGCCGGACGAGCGCCGCAGGCG
GGACGCCATGACGAAGGGATTCCGCTGGATTGTCGGCATGCAGAGCTCGAACGGCGGTTGGGGCGCCTAC
GACGTCGACAACACGAGCGATCTCCCGAACCACACCCCGTTCTGCGACTTCGGCGAAGTGACCGATCCGC
CGTCAGAGGACGTCACCGCCCACGTGCTCGAGTGTTTCGGCAGCTTCGGGTACGATGACGCCTGGAAGGT
CATCCGGCGCGCGGTGGAATATCTCAAGCGGGAGCAGAAGCCGGACGGCAGCTGGTTCGGTCGTTGGGGC
GTCAATTACCTCTACGGCACGGGCGCGGTGGTGTCGGCGCTGAAGGCGGTCGGGATCGACACGCGCGAGC
CGTACATTCAAAAGGCGCTCGACTGGGTCGAGCAGCATCAGAACCCGGACGGCGGCTGGGGCGAGGACTG
CCGCTCGTACGAGGATCCGGCGTACGCGGGTAAGGGCGCGAGCACCCCGTCGCAGACGGCCTGGGCGCTG
ATGGCGCTCATCGCGGGCGGCAGGGCGGAGTCCGAGGCCGCGCGCCGCGGCGTGCAATACCTCGTGGAGA
CGCAGCGCCCGGACGGCGGCTGGGATGAGCCGTACTACACCGGCACGGGCTTCCCAGGGGATTTCTACCT
CGGCTACACCATGTACCGCCACGTGTTTCCGACGCTCGCGCTCGGCCGCTACAAGCAAGCCATCGAGCGC
AGGTGA SEQ ID NO: 13 (amino acid sequence of AacSHC enzyme variant 215G2)
MAEQLVEAPAYARTLDRAVEYLLSCQKDEGYWWGPLLSNVTMEAEYVLLCHILDRVDRDRMEKIRRYLLH
EQREDGTWALYPGGPPDLDTTIEAYVALKYIGMSRDEEPMQKALRFIQSQGGIESSRVFTRRWLALVGEY
PWEKVPMVPPEIMFLGKRMPLNIYEFGSWARATVVALSIVMSRQPVFPLPERARVPELYETDVPPRRRGA
KGGGGWIFDALDRVLHGYQKLSVHPFRRAAEIRALDWLLERQAGDGSWGGIQPPWFYALIALKILDMTQH
PAFIKGWEGLELYGVELDYGGWMFQASISPVWDTGLAVLALRAAGLPADHDRLVKAGEWLLDRQITVPGD
WAVKRPNLKPGGFAFQFDNVYYPDVDDTAVVVWALNTLRLPDERRRRDAMTKGFRWIVGMQSSNGGWGAY
DVDNTSDLPNHTPFCDFGEVTDPPSEDVTAHVLECFGSFGYDDAWKVIRRAVEYLKREQKPDGSWFGRWG
VNYLYGTGAVVSALKAVGIDTREPYIQKALDWVEQHQNPDGGWGEDCRSYEDPAYAGKGASTPSQTAWAL
MALIAGGRAESEAARRGVQYLVETQRPDGGWDEPYYTGTGFPGDFYLGYTMYRHVFPTLALGRYKQAIER
R SEQ ID NO: 14 (nucleotide sequence encoding Aac 215G2 SHC enzyme variant)
ATGGCTGAGCAGTTGGTGGAAGCTCCGGCCTACGCGCGGACGCTGGATCGCGCGGTGGAGTATCTCCTCT
CCTGCCAAAAGGACGAAGGCTACTGGTGGGGCCCGCTTCTGAGCAACGTCACGATGGAAGCGGAGTACGT
CCTCTTGTGCCACATTCTCGATCGCGTCGATCGGGATCGCATGGAGAAGATCCGGCGGTACCTGTTGCAC
GAGCAGCGCGAGGACGGCACGTGGGCCCTGTACCCGGGTGGCCCGCCGGACCTCGACACGACCATCGAGG
CGTACGTCGCGCTCAAGTATATCGGCATGTCGCGCGACGAGGAGCCGATGCAGAAGGCGCTCCGGTTCAT
TCAGAGCCAGGGCGGGATCGAGTCGTCGCGCGTGTTCACGCGGAGGTGGCTGGCGCTGGTGGGAGAATAT
CCGTGGGAGAAGGTGCCCATGGTCCCGCCGGAGATCATGTTCCTCGGCAAGCGCATGCCGCTCAACATCT
ACGAGTTTGGCTCGTGGGCTCGGGCGACCGTCGTGGCGCTCTCGATTGTGATGAGCCGCCAGCCGGTGTT
CCCGCTGCCCGAGCGGGCGCGCGTGCCCGAGCTGTACGAGACCGACGTGCCTCCGCGCCGGCGCGGTGCC
AAGGGAGGGGGTGGGTGGATCTTCGACGCGCTCGACCGGGTGCTGCACGGGTATCAGAAGCTGTCGGTGC
ACCCGTTCCGCCGCGCGGCCGAGATCCGCGCCTTGGACTGGTTGCTCGAGCGCCAGGCCGGAGACGGCAG
CTGGGGCGGGATTCAGCCGCCTTGGTTTTACGCGCTCATCGCGCTCAAGATTCTCGACATGACGCAGCAT
CCGGCGTTCATCAAGGGCTGGGAAGGTCTAGAGCTGTACGGCGTGGAGCTGGATTACGGAGGATGGATGT
TTCAGGCTTCCATCTCGCCGGTGTGGGACACGGGCCTCGCCGTGCTCGCGCTGCGCGCTGCGGGGCTTCC
GGCCGATCACGACCGCTTGGTCAAGGCGGGCGAGTGGCTGTTGGACCGGCAGATCACGGTTCCGGGCGAC
TGGGCGGTGAAGCGCCCGAACCTCAAGCCGGGCGGGTTCGCGTTCCAGTTCGACAACGTGTACTACCCGG
ACGTGGACGACACGGCCGTCGTGGTGTGGGCGCTCAACACCCTGCGCTTGCCGGACGAGCGCCGCAGGCG
GGACGCCATGACGAAGGGATTCCGCTGGATTGTCGGCATGCAGAGCTCGAACGGCGGTTGGGGCGCCTAC
GACGTCGACAACACGAGCGATCTCCCGAACCACACCCCGTTCTGCGACTTCGGCGAAGTGACCGATCCGC
CGTCAGAGGACGTCACCGCCCACGTGCTCGAGTGTTTCGGCAGCTTCGGGTACGATGACGCCTGGAAGGT
CATCCGGCGCGCGGTGGAATATCTCAAGCGGGAGCAGAAGCCGGACGGCAGCTGGTTCGGTCGTTGGGGC
GTCAATTACCTCTACGGCACGGGCGCGGTGGTGTCGGCGCTGAAGGCGGTCGGGATCGACACGCGCGAGC -continued

SEQUENCE LISTING

CGTACATTCAAAAGGCGCTCGACTGGGTCGAGCAGCATCAGAACCCGGACGGCGGCTGGGGCGAGGACTG
CCGCTCGTACGAGGATCCGGCGTACGCGGGTAAGGGCGCGAGCACCCCGTCGCAGACGGCCTGGGCGCTG
ATGGCGCTCATCGCGGGCGGCAGGGCGGAGTCCGAGGCCGCGCGCCGCGGCGTGCAATACCTCGTGGAGA
CGCAGCGCCCGGACGGCGGCTGGGATGAGCCGTACTACACCGGCACGGGCTTCCCAGGGGATTTCTACCT
CGGCTACACCATGTACCGCCACGTGTTTCCGACGCTCGCGCTCGGCCGCTACAAGCAAGCCATCGAGCGC
AGGTGA

SEQ ID NO: 15 (amino acid sequence of wild-type ZmoSHC1)
MGIDRMNSLSRLLMKKIFGAEKTSYKPASDTIIGTDTLKRPNRRPEPTAKVDKTIFKTMGNSLNNTLVSA
CDWLIGQQKPDGHWVGAVESNASMEAEWCLALWFLGLEDHPLRPRLGNALLEMQREDGSWGVYFGAGNGD
INATVEAYAALRSLGYSADNPVLKKAAAWIAEKGGLKNIRVFTRYWLALIGEWPWEKTPNLPPEIIWFPD
NFVFSIYNFAQWARATMVPIAILSARRPSRPLRPQDRLDELFPEGRARFDYELPKKEGIDLWSQFFRTTD
RGLHWVQSNLLKRNSLREAAIRHVLEWIIRHQDADGGWGGIQPPWVYGLMALHGEGYQLYHPVMAKALSA
LDDPGWRHDRGESSWIQATNSPVWDTMLALMA1KDAKAEDRFTPEMDKAADWLLARQVKVKGDWSIKLPD
VEPGGWAFEYANDRYPDTDDTAVALIALSSYRDKEEWQKKGVEDAITRGVNWLIAMQSECGGWGAFDKDN
NRSILSKIPFCDFGESIDPPSVDVTAHVLEAFGTLGLSRDMPVIQKAIDYVRSEQEAEGAWFGRWGVNYI
YGTGAVLPALAAIGEDMTQPYITKACDWLVAHCQEDGGWGESCSSYME SEQ ID NO: 16 (amino acid sequence of wild-type ZmoSHC2)
MTVSTSSAFHHSPLSDDVEPIIQKATRALLEKQQQDGHWVFELEADATIPAEYILLKHYLGEPEDLEIEA
KIGRYLRRIQGEHGGWSLFYGGDLDLSATVKAYFALKMIGDSPDAPHMLRARNEILARGGAMRANVFTRI
QLALFGAMSWEHVPQMPVELMLMPEWFPVHINKMAYWARTVLVPLLVLQALKPVARNRRGILVDELFVPD
VLPTLQESGDPIWRRFFSALDKVLHKVEPYWPKNMRAKAIHSCVHFVTERLNGEDGLGAIYPAIANSVMM
YDALGYPENHPERAIARRAVEKLMVLDGTEDQGDKEVYCQPCLSPIWDTALVAHAMLEVGGDEAEKSAIS
ALSWLKPQQILDVKGDWAWRRPDLRPGGWAFQYRNDYYPDVDDTAVVTMAMDRAAKLSDLHDDFEESKAR
AMEWTIGMQSDNGGWGAFDANNSYTYLNNIPFADHGALLDPPTVDVSARCVSMMAQAGISITDPKMKAAV
DYLLKEQEEDGSWFGRWGVNYIYGTWSALCALNVAALPHDHLAVQKAVAWLKTIQNEDGGWGENCDSYAL
DYSGYEPMDSTASQTAWALLGLMAVGEANSEAVTKGINWLAQNQDEEGLWKEDYYSGGGFPRVFYLRYHG
YSKYFPLWALARYRNLKKANQPIVHYGM SEQ ID NO: 17 (amino acid sequence of wild-type BjaSHC)
MTVTSSASARATRDPGNYQTALQSTVRAAADWLIANQKPDGHWVGRAESNACMEAQWCLALWFMGLEDHP
LRKRLGQSLLDSQRPDGAWQVYFGAPNGDINATVEAYAALRSLGFRDDEPAVRRAREWIEAKGGLRNIRV
FTRYWLALIGEWPWEKTPNIPPEVIWFPLWFPFSIYNFAQWARATLMPIAVLSARRPSRPLPPENRLDAL
FPHGRKAFDYELPVKAGAGGWDRFFRGADKVLHKLQNLGNRLNLGLFRPAATSRVLEWMIRHQDFDGAWG
GIQPPWIYGLMALYAEGYPLNHPVLAKGLDALNDPGWRVDVGDATYIQATNSPVWDTILTLLAFDDAGVL
GDYPEAVDKAVDWVLQRQVRVPGDWSMKLPHVKPGGWAFEYANNYYPDTDDTAVALIALAPLRHDPKWKA
KGIDEAIQLGVDWLIGMQSQGGGWGAFDKDNNCKILTKIPFCDYGEALDPPSVDVTAHIIEAFGKLGISR
NHPSMVQALDYIRREQEPSGPWFGRWGVNYVYGTGAVLPALAAIGEDMTQPYIGRACDWLVAHQQADGGW
GESCASYMDVSAVGRGTTTASQTAWALMALLAANRPQDKDAIERGCMWLVERQSAGTWDEPEFTGTGFPG
YGVGQTIKLNDPALSQRLMQGPELSRAFMLRYGMYRHYFPLMALGRALRPQSHS SEQ ID NO: 18 (amino acid sequence of wild-type TelSHC)
MPTSLATAIDPKQLQQAIRASQDFLFSQQYAEGYWWAELESNVTMTAEVILLHKIWGTEQRLPLAKAEQY
LRNHQRDHGGWELFYGDGGDLSTSVEAYMGLRLLGVPETDPALVKARQFILARGGISKTRIFTKLHLALI
GCYDWRGIPSLPPWIMLLPEGSPFTIYEMSSWARSSTVPLLIVMDRKPVYGMDPPITLDELYSEGRANVV
WELPRQGDWRDVFIGLDRVFKLFETLNIHPLREQGLKAAEEWVLERQEASGDWGGIIPAMLNSLLALRAL
DYAVDDPIVQRGMAAVDRFAIETETEYRVQPCVSPVWDTALVMRAMVDSGVAPDHPALVKAGEWLLSKQI
LDYGDWHIKNKKGRPGGWAFEFENRFYPDVDDTAVVVMALHAVTLPNENLKRRAIERAVAWIASMQCRPG
GWAAFDVDNDQDWLNGIPYGDLKAMIDPNTADVTARVLEMVGRCQLAFDRVALDRALAYLRNEQEPEGCW
FGRWGVNYLYGTSGVLTALSLVAPRYDRWRIRRAAEWLMQCQNADGGWGETCWSYHDPSLKGKGDSTASQ
TAWAIIGLLAAGDATGDYATEAIERGIAYLLETQRPDGTWHEDYFTGTGFPCHFYLKYHYYQQHFPLTAL
GRYARWRNLLAT SEQ ID NO: 19 (amino acid sequence of wild-type ApaSHC1
MNMASRFSLKKILRSGSDTQGTNVNTLIQSGTSDIVRQKPAPQEPADLSALKAMGNSLTHTLSSACEWLM
KQQKPDGHWVGSVGSNASMEAEWCLALWFLGLEDHPLRPRLGKALLEMQRPDGSWGTYYGAGSGDINATV
ESYAALRSLGYAEDDPAVSKAAAWIISKGGLKNVRVFTRYWLALIGEWPWEKTPNLPPEIIWFPDNFVFS
IYNFAQWARATMMPLAILSARRPSRPLRPQDRLDALFPGGRANFDYELPTKEGRDVIADFFRLADKGLHW
LQSSFLKRAPSREAAIKYVLEWIIWHQDADGGWGGIQPPWVYGLMALHGEGYQFHHPVMAKALDALNDPG
WRHDKGDASWIQATNSPVWDTMLSLMALHDANAEERFTPEMDKALDWLLSRQVRVKGDWSVKLPNTEPGG
WAFEYANDRYPDTDDTAVALIAIASCRNRPEWQAKGVEEAIGRGVRWLVAMQSSCGGWGAFDKDNNKSIL
AKIPFCDFGEALDPPSVDVTAHVLEAFGLLGLPRDLPCIQRGLAYIRKEQDPTGPWFGRWGVNYLYGTGA
VLPALAALGEDMTQPYISKACDWLINCQQENGGWGESCASYMEVSSIGHGATTPSQTAWALMGLIAANRP
QDYEAIAKGCRYLIDLQEEDGSWNEEEFTGTGFPGYGVGQTIKLDDPAISKRLMQGAELSRAFMLRYDLY
RQLFPIIALSRASRLIKLGN SEQ ID NO: 20 (amino acid sequence of wild-type GmoSHC)
MSPADISTKSSSFQRLDNMLPEAVSSACDWLIDQQKPDGHWVGPVESNACMEAQWCLALWFLGQEDHPLR
PRLAQALLEMQREDGSWGIYVGADHGDINTTVEAYAALRSMGYAADMPIMAKSAAWIQQKGGLRNVRVFT
RYWLALIGEWPWDKTPNLPPEIIWLPDNFIFSIYNFAQWARATMMPLTILSARRPSRPLLPENRLDGLFP
EGRENFDYELPVKGEEDLWGRFFRAADKGLHSIQSFPVRRFVPREAAIRHVIEWIIRHQDADGGWGGIQP
PWIYGLMALSVEGYPLHHPVLAKAMDALNDPGWRRDKGDASWIQATNSPVWDTMLAVLALHDAGAEDRYS
PQMDKAIGWLLDRQVRVKGDWSIKLPDTEPGGWAFEYANDKYPDTDDTAVALIALAGCRHRPEWRERDIE
GAISRGVNWLLAMQSSSGGWGAFDKDNNRSILTKIPFCDFGEALDPPSVDVTAHVLEAFGLLGISRNHPS -continued

| SEQUENCE LISTING |
|---|
| VQKALAYIRSEQERNGAWFGRWGVNYVYGTGAVLPALAAIGEDMTQPYIVRACDWLMSVQQENGGWGESC<br>ASYMDINAVGHGVATASQTAWALIGLLAAKRPKDREAIARGCQFLIERQEDGSWTEEEYTGTGFPGYGVG<br>QAIKLDDPSLPDRLLQGAELSRAFMLRYDLYRCYFPVMALSRARRMMKEDASAAA |
| SEQ ID NO: 21 (amino acid sequence of wild-type BmeSHC)<br>MIILLKEVQLEIQRRIAYLRPTQKNDGSFRYCFETGVMPDAFLIMLLRTFDLDKEVLIKQLTER<br>IVSLQNEDGLWTLFDDEEHNLSATIQAYTALLYSGYYQKNDRILRKAERYIIDSGGISRAHFLT<br>RWMLSVNGLYEWPKLFYLPLSLLLVPTYVPLNFYELSTYARIHFVPMMVAGNKKFSLTSRHTPS<br>LSHLDVREQKQESEETTQESRASIFLVDHLKQLASLPSYIHKLGYQAAERYMLERIEKDGTLYS<br>YATSTFFMIYGLLALGYKKDSFVIQKAIDGICSLLSTCSGHVHVENSTSTVWDTALLSYALQEA<br>GVPQQDPMIKGTTRYLKKRQHTKLGDWQFHNPNTAPGGWGFSDINTNNPDLDDTSAAIRALSRR<br>AQTDTDYLESWQRGINWLLSMQNKDGGFAAFEKNTDSILFTYLPLENAKDAATDPATADLTGRV<br>LECLGNFAGMNKSHPSIKAAVKWLFDHQLDNGSWYGRWGVCYIYGTWAAITGLRAVGVSASDPR<br>IIKAINWLKSIQQEDGGFGESCYSASLKKYVPLSFSTPSQTAWALDALMTICPLKDQSVEKGIK<br>FLLNPNLTEQQTHYPTGIGLPGQFYIQYHSYNDIFPLLALAHYAKKHSS |
| SEQ ID NO: 22 (amino acid sequence of AacSHC enzyme variant #49)<br>MAEQLVEAPAYARTLDRAVEYLLSCQKDEGYWWGPLLSNVTMEAEYVLLCHILDRVDRDRMEKIRRYLLH<br>EQREDGTWALYPGGPPDLDTTIEAYVALKYIGMSRDEEPMQKALRFIQSQGGIESSRVFTRRWLALVGEY<br>PWEKVPMVPPEIMFLGKRMPLNIYEFGSWARATVVALSIVMSRQPVFPLPERARVPELYETDVPPRRRGA<br>KGGGGWIFDALDRVLHGYQKLSVHPFRRAAEIRALDWLLERQAGDGSWGGIQPPWFYALIALKILDMTQH<br>PAFIKGWEGLELYGVELDYGGWMFQASISPVWDTGLAVLALRAAGLPADHDRLVKAGEWLLDRQITVPGD<br>WAVKRPNLKPGGFAFQFDNVYYPDVDDTAVVVWALNTLRLPDERRRRDAMTKGFRWIVGMQSSNGGWGAY<br>DVDNTSDLPNLTPFCDFGEVTDPPSEDVTAHVIECFGSFGYDDAWKVIRRAVEYLKREQKPDGSWFGRWG<br>VNYLYGTGAVVSALKAVGIDTREPYIQKALDWVEQHQNPDGGWGEDCRSYEDPAYAGKGASTPSQTTWAL<br>MALIAGGRAESEAARRGVQYLVETQRPDGGWDEPYYTGTGFPGDFYLGYTMYRHVFPTLALGRYKQAIER<br>R |

The invention claimed is:

1. A method for making a compound of formula (I),

Formula (I)

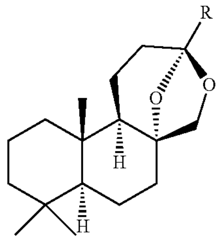

comprising contacting a compound of formula (II) with a squalene-hopene cyclase (SHC) enzyme, Formula (II)

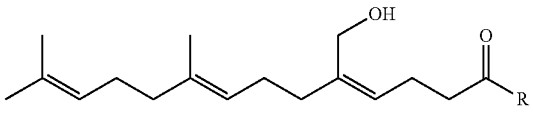

wherein R is H, methyl, or ethyl.

2. The method of claim 1 comprising contacting a compound of formula (II) wherein the double bond between C-8 and C-9 is in E-configuration and the double bond between C-4 and C-5 is in Z-configuration with the SHC enzyme.

3. The method of claim 1, wherein a compound of formula (III) is made as a by-product, Formula (III)

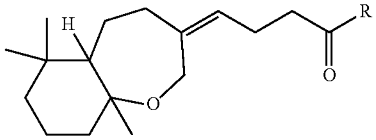

wherein R is H, methyl, or ethyl.

4. The method of claim 3, wherein a compound of formula (IIIa) is made as a by-product, Formula (IIIa)

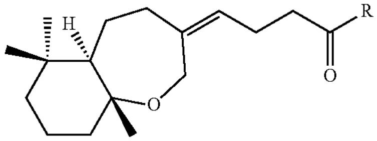

wherein R is H, methyl, or ethyl.

5. The method of claim 1, wherein R is methyl.

6. The method of claim 1, wherein the method further comprises purifying the compound of formula (I).

7. A composition comprising a compound of formula (I) and a compound of formula (III):

Formula (I)

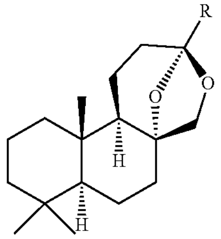

Formula (III)

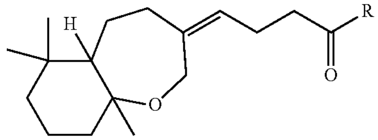

wherein R is H, methyl, or ethyl, wherein the compounds are produced by the method of claim 1.

8. The composition of claim 7, wherein R is methyl.

9. A composition obtained by the method of claim 1, wherein the composition comprises a compound of formula (I) and a compound of formula (III):

Formula (I)

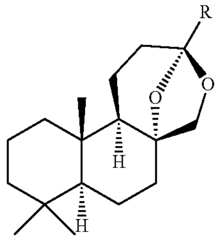

Formula (III)

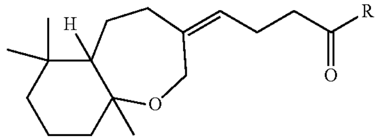

wherein R is H, methyl, or ethyl.

10. A method of using the composition of claim 7 as in a fragrance composition.

11. A consumer product comprising the composition of claim 7.

12. The method of claim 2, wherein a compound of formula (III) is made as a by-product, Formula (III)

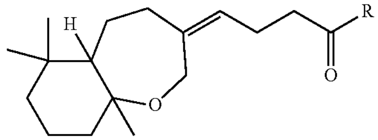

wherein R is H, methyl or ethyl.

13. The method of claim 12, wherein a compound of formula (IIIa) is made as a by-product,
Formula (IIIa)
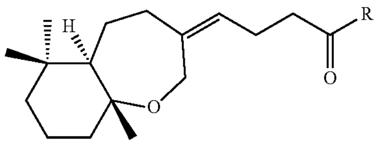
wherein R is H, methyl, or ethyl.
14. The composition according to claim 9, wherein R is methyl.
15. A method of using the composition of claim 8 as in a fragrance composition.
16. A consumer product comprising the composition of claim 8.
* * * * *

SEQUENCE LISTING

<160> NUMBER OF SEQ ID NOS: 22

<210> SEQ ID NO 1
<211> LENGTH: 631
<212> TYPE: PRT
<213> ORGANISM: Alicyclobacillus acidocaldarius

<400> SEQUENCE: 1

```
Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Met Trp Leu Ala Leu Val Gly Glu Tyr Pro Trp Glu Lys
    130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
```

-continued

```
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Ala
    210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365

Asn Val Tyr Tyr Pro Asp Val Asp Asp Thr Ala Val Val Val Trp Ala
    370                 375                 380

Leu Asn Thr Leu Arg Leu Pro Asp Glu Arg Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn His Ile
            420                 425                 430

Pro Phe Cys Asp Phe Gly Glu Val Thr Asp Pro Pro Ser Glu Asp Val
        435                 440                 445

Thr Ala His Val Leu Glu Cys Phe Gly Ser Phe Gly Tyr Asp Asp Ala
    450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
        515                 520                 525

Pro Asp Gly Gly Trp Gly Glu Asp Cys Arg Ser Tyr Glu Asp Pro Ala
    530                 535                 540

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
        595                 600                 605
```

-continued

```
Tyr Thr Met Tyr Arg His Val Phe Pro Thr Leu Ala Leu Gly Arg Tyr
    610                 615                 620

Lys Gln Ala Ile Glu Arg Arg
625                 630


<210> SEQ ID NO 2
<211> LENGTH: 1896
<212> TYPE: DNA
<213> ORGANISM: Alicyclobacillus acidocaldarius

<400> SEQUENCE: 2

atggctgagc agttggtgga agcgccggcc tacgcgcgga cgctggatcg cgcggtggag      60

tatctcctct cctgccaaaa ggacgaaggc tactggtggg ggccgcttct gagcaacgtc     120

acgatggaag cggagtacgt cctcttgtgc cacattctcg atcgcgtcga tcgggatcgc     180

atggagaaga tccggcggta cctgttgcac gagcagcgcg aggacggcac gtgggccctg     240

tacccgggtg ggccgccgga cctcgacacg accatcgagg cgtacgtcgc gctcaagtat     300

atcggcatgt cgcgcgacga ggagccgatg cagaaggcgc tccggttcat tcagagccag     360

ggcgggatcg agtcgtcgcg cgtgttcacg cggatgtggc tggcgctggt gggagaatat     420

ccgtgggaga aggtgcccat ggtcccgccg gagatcatgt tcctcggcaa gcgcatgccg     480

ctcaacatct acgagtttgg ctcgtgggct cgggcgaccg tcgtggcgct ctcgattgtg     540

atgagccgcc agccggtgtt cccgctgccc gagcgggcgc gcgtgcccga gctgtacgag     600

accgacgtgc ctccgcgccg gcgcggtgcc aagggagggg gtgggtggat cttcgacgcg     660

ctcgaccggg cgctgcacgg gtatcagaag ctgtcggtgc acccgttccg ccgcgcggcc     720

gagatccgcg ccttggactg gttgctcgag cgccaggccg gagacggcag ctggggcggg     780

attcagccgc cttggtttta cgcgctcatc gcgctcaaga ttctcgacat gacgcagcat     840

ccggcgttca tcaagggctg ggaaggtcta gagctgtacg gcgtggagct ggattacgga     900

ggatggatgt ttcaggcttc catctcgccg gtgtgggaca cgggcctcgc cgtgctcgcg     960

ctgcgcgctg cggggcttcc ggccgatcac gaccgcttgg tcaaggcggg cgagtggctg    1020

ttggaccggc agatcacggt tccgggcgac tgggcggtga agcgcccgaa cctcaagccg    1080

ggcgggttcg cgttccagtt cgacaacgtg tactacccgg acgtggacga cacggccgtc    1140

gtggtgtggg cgctcaacac cctgcgcttg ccggacgagc gccgcaggcg ggacgccatg    1200

acgaagggat tccgctggat tgtcggcatg cagagctcga acggcggttg gggcgcctac    1260

gacgtcgaca acacgagcga tctcccgaac cacatcccgt tctgcgactt cggcgaagtg    1320

accgatccgc cgtcagagga cgtcaccgcc cacgtgctcg agtgtttcgg cagcttcggg    1380

tacgatgacg cctggaaggt catccggcgc gcggtggaat atctcaagcg ggagcagaag    1440

ccggacggca gctggttcgg tcgttggggc gtcaattacc tctacggcac gggcgcggtg    1500

gtgtcggcgc tgaaggcggt cgggatcgac acgcgcgagc cgtacattca aaaggcgctc    1560

gactgggtcg agcagcatca gaacccggac ggcggctggg gcgaggactg ccgctcgtac    1620

gaggatccgg cgtacgcggg taagggcgcg agcaccccgt cgcagacggc ctgggcgctg    1680

atggcgctca tcgcgggcgg cagggcggag tccgaggccg cgcgccgcgg cgtgcaatac    1740

ctcgtggaga cgcagcgccc ggacggcggc tgggatgagc cgtactacac cggcacgggc    1800

ttcccagggg atttctacct cggctacacc atgtaccgcc acgtgtttcc gacgctcgcg    1860

ctcggccgct acaagcaagc catcgagcgc aggtga                              1896
```

<210> SEQ ID NO 3
<211> LENGTH: 630
<212> TYPE: PRT
<213> ORGANISM: Artificial sequence
<220> FEATURE:
<223> OTHER INFORMATION: SHC enzyme variant #65

<400> SEQUENCE: 3

```
Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Arg Trp Leu Ala Leu Val Gly Glu Tyr Pro Trp Glu Lys
    130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Val
    210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365
```

-continued

```
Asn Val Tyr Tyr Pro Asp Val Asp Asp Thr Ala Val Val Val Trp Ala
    370                 375                 380

Leu Asn Thr Leu Arg Leu Pro Asp Glu Arg Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn His Thr
            420                 425                 430

Pro Phe Cys Asp Phe Gly Glu Val Thr Asp Pro Pro Ser Glu Asp Val
        435                 440                 445

Thr Ala His Val Leu Glu Cys Phe Gly Ser Phe Gly Tyr Asp Asp Ala
    450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
        515                 520                 525

Pro Asp Gly Gly Trp Gly Glu Asp Cys Arg Ser Tyr Glu Asp Pro Ala
    530                 535                 540

Tyr Ala Gly Lys Gly Ala Ser Thr Pro Ser Gln Thr Thr Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
        595                 600                 605

Tyr Thr Met Tyr Ser His Val Phe Pro Thr Leu Ala Leu Gly Arg Tyr
    610                 615                 620

Lys Gln Ala Ile Glu Arg
625                 630


<210> SEQ ID NO 4
<211> LENGTH: 1896
<212> TYPE: DNA
<213> ORGANISM: Artificial sequence
<220> FEATURE:
<223> OTHER INFORMATION: SHC enzyme variant #65

<400> SEQUENCE: 4

atggctgagc agttggtgga agctccggcc tacgcgcgga cgctggatcg cgcggtggag      60

tatctcctct cctgccaaaa ggacgaaggc tactggtggg ggccgcttct gagcaacgtc     120

acgatggaag cggagtacgt cctcttgtgc cacattctcg atcgcgtcga tcgggatcgc     180

atggagaaga tccggcggta cctgttgcac gagcagcgcg aggacggcac gtgggccctg     240

tacccgggtg ggccgccgga cctcgacacg accatcgagg cgtacgtcgc gctcaagtat     300

atcggcatgt cgcgcgacga ggagccgatg cagaaggcgc tccggttcat tcagagccag     360

ggcgggatcg agtcgtcgcg cgtgttcacg cggaggtggc tggcgctggt gggagaatat     420

ccgtgggaga aggtgcccat ggtcccgccg gagatcatgt tcctcggcaa gcgcatgccg     480

ctcaacatct acgagtttgg ctcgtgggct cgggcgaccg tcgtggcgct ctcgattgtg     540
```

-continued

```
atgagccgcc agccggtgtt cccgctgccc gagcgggcgc gcgtgcccga gctgtacgag    600

accgacgtgc ctccgcgccg gcgcggtgcc aagggagggg gtgggtggat cttcgacgcg    660

ctcgaccggg tgctgcacgg gtatcagaag ctgtcggtgc acccgttccg ccgcgcggcc    720

gagatccgcg ccttggactg gttgctcgag cgccaggccg gagacggcag ctggggcggg    780

attcagccgc cttggtttta cgcgctcatc gcgctcaaga ttctcgacat gacgcagcat    840

ccggcgttca tcaagggctg ggaaggtcta gagctgtacg gcgtggagct ggattacgga    900

ggatggatgt ttcaggcttc catctcgccg gtgtgggaca cgggcctcgc cgtgctcgcg    960

ctgcgcgctg cggggcttcc ggccgatcac gaccgcttgg tcaaggcggg cgagtggctg   1020

ttggaccggc agatcacggt tccgggcgac tgggcggtga agcgcccgaa cctcaagccg   1080

ggcgggttcg cgttccagtt cgacaacgtg tactacccgg acgtggacga cacggccgtc   1140

gtggtgtggg cgctcaacac cctgcgcttg ccggacgagc gccgcaggcg ggacgccatg   1200

acgaagggat tccgctggat tgtcggcatg cagagctcga acggcggttg gggcgcctac   1260

gacgtcgaca acacgagcga tctcccgaac cacaccccgt tctgcgactt cggcgaagtg   1320

accgatccgc cgtcagagga cgtcaccgcc cacgtgctcg agtgtttcgg cagcttcggg   1380

tacgatgacg cctggaaggt catccggcgc gcggtggaat atctcaagcg ggagcagaag   1440

ccggacggca gctggttcgg tcgttggggc gtcaattacc tctacggcac gggcgcggtg   1500

gtgtcggcgc tgaaggcggt cgggatcgac acgcgcgagc cgtacattca aaaggcgctc   1560

gactgggtcg agcagcatca gaacccggac ggcggctggg gcgaggactg ccgctcgtac   1620

gaggatccgg cgtacgcggg taagggcgcg agcaccccgt cgcagacgac ctgggcgctg   1680

atggcgctca tcgcgggcgg cagggcggag tccgaggccg cgcgccgcgg cgtgcaatac   1740

ctcgtggaga cgcagcgccc ggacggcggc tgggatgagc cgtactacac cggcacgggc   1800

ttcccagggg atttctacct cggctacacc atgtacagcc acgtgtttcc gacgctcgcg   1860

ctcggccgct acaagcaagc catcgagcgc aggtga                             1896
```

<210> SEQ ID NO 5
<211> LENGTH: 631
<212> TYPE: PRT
<213> ORGANISM: Artificial sequence
<220> FEATURE:
<223> OTHER INFORMATION: SHC enzyme variant #66

<400> SEQUENCE: 5

```
Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

His Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125
```

-continued

```
Phe Thr Arg Arg Trp Leu Ala Leu Val Gly Glu Tyr Pro Trp Glu Lys
    130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Val
    210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365

Asn Val Tyr Tyr Pro Asp Val Asp Asp Thr Ala Val Val Val Trp Ala
    370                 375                 380

Leu Asn Thr Leu Arg Leu Pro Asp Glu Arg Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn His Thr
            420                 425                 430

Pro Phe Cys Asp Phe Gly Glu Val Thr Asp Pro Pro Ser Glu Asp Val
        435                 440                 445

Thr Ala His Val Leu Glu Cys Phe Gly Ser Phe Gly Tyr Asp Asp Ala
    450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
        515                 520                 525

Pro Asp Gly Gly Trp Gly Glu Asp Cys Arg Ser Tyr Glu Asp Pro Ala
    530                 535                 540
```

-continued

```
Tyr Ala Gly Lys Gly Ala Ser Thr Pro Ser Gln Thr Thr Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
        595                 600                 605

Tyr Thr Met Tyr Ser His Val Phe Pro Thr Leu Ala Leu Gly Arg Tyr
    610                 615                 620

Lys Gln Ala Ile Glu Arg Arg
625                 630


<210> SEQ ID NO 6
<211> LENGTH: 1896
<212> TYPE: DNA
<213> ORGANISM: Artificial sequence
<220> FEATURE:
<223> OTHER INFORMATION: SHC enzyme variant #66

<400> SEQUENCE: 6

atggctgagc agttggtgga agctccggcc tacgcgcgga cgctggatcg cgcggtggag      60

tatctcctct cctgccaaaa ggacgaaggc tactggtggg ggccgcttct gagcaacgtc     120

acgatggaag cggagtacgt cctcttgtgc cacattctcg atcgcgtcga tcgggatcgc     180

atggagaaga tccggcggta cctgttgcac gagcagcgcg aggacggcac gtgggccctg     240

cacccgggtg ggccgccgga cctcgacacg accatcgagg cgtacgtcgc gctcaagtat     300

atcggcatgt cgcgcgacga ggagccgatg cagaaggcgc tccggttcat tcagagccag     360

ggcgggatcg agtcgtcgcg cgtgttcacg cggaggtggc tggcgctggt gggagaatat     420

ccgtgggaga aggtgcccat ggtcccgccg gagatcatgt tcctcggcaa gcgcatgccg     480

ctcaacatct acgagtttgg ctcgtgggct cgggcgaccg tcgtggcgct ctcgattgtg     540

atgagccgcc agccggtgtt cccgctgccc gagcgggcgc gcgtgcccga gctgtacgag     600

accgacgtgc ctccgcgccg gcgcggtgcc aagggagggg gtgggtggat cttcgacgcg     660

ctcgaccggg tgctgcacgg gtatcagaag ctgtcggtgc acccgttccg ccgcgcggcc     720

gagatccgcg ccttggactg gttgctcgag cgccaggccg gagacggcag ctggggcggg     780

attcagccgc cttggtttta cgcgctcatc gcgctcaaga ttctcgacat gacgcagcat     840

ccggcgttca tcaagggctg ggaaggtcta gagctgtacg gcgtggagct ggattacgga     900

ggatggatgt ttcaggcttc catctcgccg gtgtgggaca cgggcctcgc cgtgctcgcg     960

ctgcgcgctg cggggcttcc ggccgatcac gaccgcttgg tcaaggcggg cgagtggctg    1020

ttggaccggc agatcacggt tccgggcgac tgggcggtga agcgcccgaa cctcaagccg    1080

ggcgggttcg cgttccagtt cgacaacgtg tactacccgg acgtggacga cacggccgtc    1140

gtggtgtggg cgctcaacac cctgcgcttg ccggacgagc gccgcaggcg ggacgccatg    1200

acgaagggat tccgctggat tgtcggcatg cagagctcga acggcggttg ggcgcctac    1260

gacgtcgaca acacgagcga tctcccgaac cacaccccgt tctgcgactt cggcgaagtg    1320

accgatccgc cgtcagagga cgtcaccgcc cacgtgctcg agtgtttcgg cagcttcggg    1380

tacgatgacg cctggaaggt catccggcgc gcggtggaat atctcaagcg ggagcagaag    1440

ccggacggca gctggttcgg tcgttggggc gtcaattacc tctacggcac gggcgcggtg    1500

gtgtcggcgc tgaaggcggt cgggatcgac acgcgcgagc cgtacattca aaaggcgctc    1560
```

```
gactgggtcg agcagcatca gaacccggac ggcggctggg gcgaggactg ccgctcgtac   1620

gaggatccgg cgtacgcggg taagggcgcg agcaccccgt cgcagacgac ctgggcgctg   1680

atggcgctca tcgcgggcgg cagggcggag tccgaggccg cgcgccgcgg cgtgcaatac   1740

ctcgtggaga cgcagcgccc ggacggcggc tgggatgagc cgtactacac cggcacgggc   1800

ttcccagggg atttctacct cggctacacc atgtacagcc acgtgtttcc gacgctcgcg   1860

ctcggccgct acaagcaagc catcgagcgc aggtga                             1896
```

<210> SEQ ID NO 7
<211> LENGTH: 631
<212> TYPE: PRT
<213> ORGANISM: Artificial sequence
<220> FEATURE:
<223> OTHER INFORMATION: SHC enzyme variant #90C7

<400> SEQUENCE: 7

```
Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Ala Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Arg Trp Leu Ala Leu Val Gly Glu Tyr Pro Trp Glu Lys
    130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Val
    210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300
```

-continued

```
Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365

Asn Val Tyr Tyr Pro Asp Val Asp Asp Thr Ala Val Val Val Trp Ala
    370                 375                 380

Leu Asn Thr Leu Arg Leu Pro Asp Glu Arg Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn His Thr
            420                 425                 430

Pro Phe Cys Asp Phe Gly Glu Val Thr Asp Pro Pro Ser Glu Asp Val
        435                 440                 445

Thr Ala His Val Leu Glu Cys Phe Gly Ser Phe Gly Tyr Asp Asp Ala
    450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
        515                 520                 525

Pro Asp Gly Gly Trp Gly Glu Asp Cys Arg Ser Tyr Glu Asp Pro Ala
    530                 535                 540

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
        595                 600                 605

Tyr Thr Met Tyr Ser His Val Phe Pro Thr Leu Ala Leu Gly Arg Tyr
    610                 615                 620

Lys Gln Ala Ile Glu Arg Arg
625                 630
```

<210> SEQ ID NO 8
<211> LENGTH: 1896
<212> TYPE: DNA
<213> ORGANISM: Artificial sequence
<220> FEATURE:
<223> OTHER INFORMATION: SHC enzyme variant #90C7

<400> SEQUENCE: 8

```
atggctgagc agttggtgga agctccggcc tacgcgcgga cgctggatcg cgcggtggag      60

tatctcctct cctgccaaaa ggacgaaggc tactggtggg ggccgcttct gagcaacgtc     120

acgatggaag cggagtacgt cctcttgtgc cacattctcg atcgcgtcga tcgggatcgc     180
```

-continued

```
atggagaaga tccggcggta cctgttgcac gagcagcgcg aggacggcac gtgggccctg    240

tacccgggtg ggccgccgga cctcgacgcg accatcgagg cgtacgtcgc gctcaagtat    300

atcggcatgt cgcgcgacga ggagccgatg cagaaggcgc tccggttcat tcagagccag    360

ggcgggatcg agtcgtcgcg cgtgttcacg cggaggtggc tggcgctggt gggagaatat    420

ccgtgggaga aggtgcccat ggtcccgccg gagatcatgt tcctcggcaa gcgcatgccg    480

ctcaacatct acgagtttgg ctcgtgggct cgggcgaccg tcgtggcgct ctcgattgtg    540

atgagccgcc agccggtgtt cccgctgccc gagcgggcgc gcgtgcccga gctgtacgag    600

accgacgtgc ctccgcgccg gcgcggtgcc aagggagggg gtgggtggat cttcgacgcg    660

ctcgaccggg tgctgcacgg gtatcagaag ctgtcggtgc acccgttccg ccgcgcggcc    720

gagatccgcg ccttggactg gttgctcgag cgccaggccg gagacggcag ctggggcggg    780

attcagccgc cttggtttta cgcgctcatc gcgctcaaga ttctcgacat gacgcagcat    840

ccggcgttca tcaagggctg ggaaggtcta gagctgtacg gcgtggagct ggattacgga    900

ggatggatgt ttcaggcttc catctcgccg gtgtgggaca cgggcctcgc cgtgctcgcg    960

ctgcgcgctg cggggcttcc ggccgatcac gaccgcttgg tcaaggcggg cgagtggctg   1020

ttggaccggc agatcacggt tccgggcgac tgggcggtga agcgcccgaa cctcaagccg   1080

ggcgggttcg cgttccagtt cgacaacgtg tactacccgg acgtggacga cacggccgtc   1140

gtggtgtggg cgctcaacac cctgcgcttg ccggacgagc gccgcaggcg ggacgccatg   1200

acgaagggat tccgctggat tgtcggcatg cagagctcga acggcggttg ggcgcctac   1260

gacgtcgaca acacgagcga tctcccgaac cacaccccgt tctgcgactt cggcgaagtg   1320

accgatccgc cgtcagagga cgtcaccgcc cacgtgctcg agtgtttcgg cagcttcggg   1380

tacgatgacg cctggaaggt catccggcgc gcggtggaat atctcaagcg ggagcagaag   1440

ccggacggca gctggttcgg tcgttggggc gtcaattacc tctacggcac gggcgcggtg   1500

gtgtcggcgc tgaaggcggt cgggatcgac acgcgcgagc cgtacattca aaaggcgctc   1560

gactgggtcg agcagcatca gaacccggac ggcggctggg gcgaggactg ccgctcgtac   1620

gaggatccgg cgtacgcggg taagggcgcg agcaccccgt cgcagacggc ctgggcgctg   1680

atggcgctca tcgcgggcgg cagggcggag tccgaggccg cgcgccgcgg cgtgcaatac   1740

ctcgtggaga cgcagcgccc ggacggcggc tgggatgagc cgtactacac cggcacgggc   1800

ttcccagggg atttctacct cggctacacc atgtacagcc acgtgtttcc gacgctcgcg   1860

ctcggccgct acaagcaagc catcgagcgc aggtga                             1896
```

<210> SEQ ID NO 9
<211> LENGTH: 631
<212> TYPE: PRT
<213> ORGANISM: Artificial sequence
<220> FEATURE:
<223> OTHER INFORMATION: SHC enzyme variant #110B8

<400> SEQUENCE: 9

```
Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
```

-continued

```
    50                  55                  60

Arg Arg Tyr Leu Leu His Glu Gln Arg Glu Asp Gly Thr Trp Ala Leu
65                  70                  75                  80

His Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Arg Trp Leu Ala Leu Val Gly Glu Tyr Pro Trp Glu Lys
    130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Val
    210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365

Asn Val Tyr Tyr Pro Asp Val Asp Asp Thr Ala Val Val Val Trp Ala
    370                 375                 380

Leu Asn Thr Leu Arg Leu Pro Asp Glu Arg Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn Leu Thr
            420                 425                 430

Pro Phe Cys Asp Phe Gly Glu Val Thr Asp Pro Pro Ser Glu Asp Val
        435                 440                 445

Thr Ala His Val Leu Glu Cys Phe Gly Ser Phe Gly Tyr Asp Asp Ala
    450                 455                 460

Trp Lys Val Ile Arg Arg Ala Val Glu Tyr Leu Lys Arg Glu Gln Lys
465                 470                 475                 480
```

-continued

```
Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
        515                 520                 525

Pro Asp Gly Gly Trp Gly Glu Asp Cys Arg Ser Tyr Glu Asp Pro Ala
    530                 535                 540

Tyr Ala Gly Lys Gly Ala Ser Thr Pro Ser Gln Thr Thr Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
        595                 600                 605

Tyr Thr Met Tyr Arg His Val Phe Pro Thr Leu Ala Leu Gly Arg Tyr
    610                 615                 620

Lys Gln Ala Ile Glu Arg Arg
625                 630
```

<210> SEQ ID NO 10
<211> LENGTH: 1896
<212> TYPE: DNA
<213> ORGANISM: Artificial sequence
<220> FEATURE:
<223> OTHER INFORMATION: SHC enzyme variant #110B8

<400> SEQUENCE: 10

```
atggctgagc agttggtgga agctccggcc tacgcgcgga cgctggatcg cgcggtggag     60

tatctcctct cctgccaaaa ggacgaaggc tactggtggg ggccgcttct gagcaacgtc    120

acgatggaag cggagtacgt cctcttgtgc cacattctcg atcgcgtcga tcgggatcgc    180

atggagaaga tccggcggta cctgttgcac gagcagcgcg aggacggcac gtgggccctg    240

cacccgggtg ggccgccgga cctcgacacg accatcgagg cgtacgtcgc gctcaagtat    300

atcggcatgt cgcgcgacga ggagccgatg cagaaggcgc tccggttcat tcagagccag    360

ggcgggatcg agtcgtcgcg cgtgttcacg cggaggtggc tggcgctggt gggagaatat    420

ccgtgggaga aggtgcccat ggtcccgccg gagatcatgt tcctcggcaa gcgcatgccg    480

ctcaacatct acgagtttgg ctcgtgggct cgggcgaccg tcgtggcgct ctcgattgtg    540

atgagccgcc agccggtgtt cccgctgccc gagcgggcgc gcgtgcccga gctgtacgag    600

accgacgtgc ctccgcgccg gcgcggtgcc aagggagggg gtgggtggat cttcgacgcg    660

ctcgaccggg tgctgcacgg gtatcagaag ctgtcggtgc acccgttccg ccgcgcggcc    720

gagatccgcg ccttggactg gttgctcgag cgccaggccg gagacggcag ctggggcggg    780

attcagccgc cttggtttta cgcgctcatc gcgctcaaga ttctcgacat gacgcagcat    840

ccggcgttca tcaagggctg ggaaggtcta gagctgtacg gcgtggagct ggattacgga    900

ggatggatgt ttcaggcttc catctcgccg gtgtgggaca cgggcctcgc cgtgctcgcg    960

ctgcgcgctg cggggcttcc ggccgatcac gaccgcttgg tcaaggcggg cgagtggctg   1020

ttggaccggc agatcacggt tccgggcgac tgggcggtga agcgcccgaa cctcaagccg   1080

ggcgggttcg cgttccagtt cgacaacgtg tactacccgg acgtggacga cacggccgtc   1140
```

-continued

```
gtggtgtggg cgctcaacac cctgcgcttg ccggacgagc gccgcaggcg ggacgccatg   1200

acgaagggat tccgctggat tgtcggcatg cagagctcga acggcggttg gggcgcctac   1260

gacgtcgaca acacgagcga tctcccgaac ctcaccccgt tctgcgactt cggcgaagtg   1320

accgatccgc cgtcagagga cgtcaccgcc cacgtgctcg agtgtttcgg cagcttcggg   1380

tacgatgacg cctggaaggt catccggcgc gcggtggaat atctcaagcg ggagcagaag   1440

ccggacggca gctggttcgg tcgttggggc gtcaattacc tctacggcac gggcgcggtg   1500

gtgtcggcgc tgaaggcggt cgggatcgac acgcgcgagc cgtacattca aaaggcgctc   1560

gactgggtcg agcagcatca gaacccggac ggcggctggg gcgaggactg ccgctcgtac   1620

gaggatccgg cgtacgcggg taagggcgcg agcaccccgt cgcagacgac ctgggcgctg   1680

atggcgctca tcgcgggcgg cagggcggag tccgaggccg cgcgccgcgg cgtgcaatac   1740

ctcgtggaga cgcagcgccc ggacggcggc tgggatgagc cgtactacac cggcacgggc   1800

ttcccagggg atttctacct cggctacacc atgtaccgcc acgtgtttcc gacgctcgcg   1860

ctcggccgct acaagcaagc catcgagcgc aggtga                             1896
```

<210> SEQ ID NO 11
<211> LENGTH: 631
<212> TYPE: PRT
<213> ORGANISM: Artificial sequence
<220> FEATURE:
<223> OTHER INFORMATION: SHC enzyme variant #115A7

<400> SEQUENCE: 11

```
Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Arg Trp Leu Ala Leu Val Gly Glu Tyr Pro Trp Glu Lys
    130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Thr Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Val
    210                 215                 220

Leu His Gly Tyr Gln Lys Leu Ser Val His Pro Phe Arg Arg Ala Ala
```

-continued

```
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Lys Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365

Asn Val Tyr Tyr Pro Asp Val Asp Asp Thr Ala Val Val Val Trp Ala
    370                 375                 380

Leu Asn Thr Leu Arg Leu Pro Asp Glu Arg Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn His Thr
            420                 425                 430

Pro Phe Cys Asp Phe Gly Glu Val Thr Asp Pro Pro Ser Glu Asp Val
        435                 440                 445

Thr Ala His Val Leu Glu Cys Phe Gly Ser Phe Gly Tyr Asp Asp Ala
    450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
        515                 520                 525

Pro Asp Gly Gly Trp Gly Glu Asp Cys Arg Ser Tyr Glu Asp Pro Ala
    530                 535                 540

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
        595                 600                 605

Tyr Thr Met Tyr Arg His Val Phe Pro Thr Leu Ala Leu Gly Arg Tyr
    610                 615                 620

Lys Gln Ala Ile Glu Arg Arg
625                 630

<210> SEQ ID NO 12
```

-continued

<211> LENGTH: 1896
<212> TYPE: DNA
<213> ORGANISM: Artificial sequence
<220> FEATURE:
<223> OTHER INFORMATION: SHC enzyme variant #115A7

<400> SEQUENCE: 12

```
atggctgagc agttggtgga agctccggcc tacgcgcgga cgctggatcg cgcggtggag     60
tatctcctct cctgccaaaa ggacgaaggc tactggtggg ggccgcttct gagcaacgtc    120
acgatggaag cggagtacgt cctcttgtgc cacattctcg atcgcgtcga tcgggatcgc    180
atggagaaga tccggcggta cctgttgcac gagcagcgcg aggacggcac gtgggccctg    240
tacccgggtg ggccgccgga cctcgacacg accatcgagg cgtacgtcgc gctcaagtat    300
atcggcatgt cgcgcgacga ggagccgatg cagaaggcgc tccggttcat tcagagccag    360
ggcgggatcg agtcgtcgcg cgtgttcacg cggaggtggc tggcgctggt gggagaatat    420
ccgtgggaga aggtgcccat ggtcccgccg gagatcatgt tcctcggcaa gcgcatgccg    480
ctcaacatct acgagtttgg ctcgtgggct cggacgaccg tcgtggcgct ctcgattgtg    540
atgagccgcc agccggtgtt cccgctgccc gagcgggcgc gcgtgcccga gctgtacgag    600
accgacgtgc ctccgcgccg gcgcggtgcc aagggagggg gtgggtggat cttcgacgcg    660
ctcgaccggg tgctgcacgg gtatcagaag ctgtcggtgc acccgttccg ccgcgcggcc    720
gagatccgcg ccttggactg gttgctcgag cgccaggccg gagacggcag ctggggcggg    780
attcagccgc cttggtttta cgcgctcatc gcgctcaaga ttctcgacaa gacgcagcat    840
ccggcgttca tcaagggctg ggaaggtcta gagctgtacg gcgtggagct ggattacgga    900
ggatggatgt ttcaggcttc catctcgccg gtgtgggaca cgggcctcgc cgtgctcgcg    960
ctgcgcgctg cggggcttcc ggccgatcac gaccgcttgg tcaaggcggg cgagtggctg   1020
ttggaccggc agatcacggt tccgggcgac tgggcggtga agcgcccgaa cctcaagccg   1080
ggcgggttcg cgttccagtt cgacaacgtg tactacccgg acgtggacga cacggccgtc   1140
gtggtgtggg cgctcaacac cctgcgcttg ccggacgagc gccgcaggcg ggacgccatg   1200
acgaagggat tccgctggat tgtcggcatg cagagctcga acggcggttg gggcgcctac   1260
gacgtcgaca acacgagcga tctcccgaac cacaccccgt tctgcgactt cggcgaagtg   1320
accgatccgc cgtcagagga cgtcaccgcc cacgtgctcg agtgtttcgg cagcttcggg   1380
tacgatgacg cctggaaggt catccggcgc gcggtggaat atctcaagcg ggagcagaag   1440
ccggacggca gctggttcgg tcgttggggc gtcaattacc tctacggcac gggcgcggtg   1500
gtgtcggcgc tgaaggcggt cgggatcgac acgcgcgagc cgtacattca aaaggcgctc   1560
gactgggtcg agcagcatca gaacccggac ggcggctggg gcgaggactg ccgctcgtac   1620
gaggatccgg cgtacgcggg taagggcgcg agcaccccgt cgcagacggc ctgggcgctg   1680
atggcgctca tcgcgggcgg cagggcggag tccgaggccg cgcgccgcgg cgtgcaatac   1740
ctcgtggaga cgcagcgccc ggacggcggc tgggatgagc cgtactacac cggcacgggc   1800
ttcccagggg atttctacct cggctacacc atgtaccgcc acgtgtttcc gacgctcgcg   1860
ctcggccgct acaagcaagc catcgagcgc aggtga                             1896
```

<210> SEQ ID NO 13
<211> LENGTH: 631
<212> TYPE: PRT
<213> ORGANISM: Artificial sequence
<220> FEATURE:
<223> OTHER INFORMATION: SHC enzyme variant #215G2

<400> SEQUENCE: 13

```
Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Arg Trp Leu Ala Leu Val Gly Glu Tyr Pro Trp Glu Lys
    130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Val
    210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365

Asn Val Tyr Tyr Pro Asp Val Asp Asp Thr Ala Val Val Val Trp Ala
    370                 375                 380

Leu Asn Thr Leu Arg Leu Pro Asp Glu Arg Arg Arg Arg Asp Ala Met
385                 390                 395                 400

Thr Lys Gly Phe Arg Trp Ile Val Gly Met Gln Ser Ser Asn Gly Gly
```

-continued

```
                405                 410                 415

Trp Gly Ala Tyr Asp Val Asp Asn Thr Ser Asp Leu Pro Asn His Thr
            420                 425                 430

Pro Phe Cys Asp Phe Gly Glu Val Thr Asp Pro Pro Ser Glu Asp Val
        435                 440                 445

Thr Ala His Val Leu Glu Cys Phe Gly Ser Phe Gly Tyr Asp Asp Ala
    450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
        515                 520                 525

Pro Asp Gly Gly Trp Gly Glu Asp Cys Arg Ser Tyr Glu Asp Pro Ala
    530                 535                 540

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
        595                 600                 605

Tyr Thr Met Tyr Arg His Val Phe Pro Thr Leu Ala Leu Gly Arg Tyr
    610                 615                 620

Lys Gln Ala Ile Glu Arg Arg
625                 630
```

<210> SEQ ID NO 14
<211> LENGTH: 1896
<212> TYPE: DNA
<213> ORGANISM: Artificial sequence
<220> FEATURE:
<223> OTHER INFORMATION: SHC enzyme variant #215G2

<400> SEQUENCE: 14

```
atggctgagc agttggtgga agctccggcc tacgcgcgga cgctggatcg cgcggtggag     60

tatctcctct cctgccaaaa ggacgaaggc tactggtggg ggccgcttct gagcaacgtc    120

acgatggaag cggagtacgt cctcttgtgc cacattctcg atcgcgtcga tcgggatcgc    180

atggagaaga tccggcggta cctgttgcac gagcagcgcg aggacggcac gtgggccctg    240

tacccgggtg ggccgccgga cctcgacacg accatcgagg cgtacgtcgc gctcaagtat    300

atcggcatgt cgcgcgacga ggagccgatg cagaaggcgc tccggttcat tcagagccag    360

ggcgggatcg agtcgtcgcg cgtgttcacg cggaggtggc tggcgctggt gggagaatat    420

ccgtgggaga aggtgcccat ggtcccgccg gagatcatgt tcctcggcaa gcgcatgccg    480

ctcaacatct acgagtttgg ctcgtgggct cgggcgaccg tcgtggcgct ctcgattgtg    540

atgagccgcc agccggtgtt cccgctgccc gagcgggcgc gcgtgcccga gctgtacgag    600

accgacgtgc ctccgcgccg gcgcggtgcc aagggagggg gtgggtggat cttcgacgcg    660

ctcgaccggg tgctgcacgg gtatcagaag ctgtcggtgc acccgttccg ccgcgcggcc    720

gagatccgcg ccttggactg gttgctcgag cgccaggccg gagacggcag ctggggcggg    780
```

-continued

```
attcagccgc cttggtttta cgcgctcatc gcgctcaaga ttctcgacat gacgcagcat    840

ccggcgttca tcaagggctg ggaaggtcta gagctgtacg gcgtggagct ggattacgga    900

ggatggatgt ttcaggcttc catctcgccg gtgtgggaca cgggcctcgc cgtgctcgcg    960

ctgcgcgctg cggggcttcc ggccgatcac gaccgcttgg tcaaggcggg cgagtggctg   1020

ttggaccggc agatcacggt tccgggcgac tgggcggtga agcgcccgaa cctcaagccg   1080

ggcgggttcg cgttccagtt cgacaacgtg tactacccgg acgtggacga cacggccgtc   1140

gtggtgtggg cgctcaacac cctgcgcttg ccggacgagc gccgcaggcg ggacgccatg   1200

acgaagggat tccgctggat tgtcggcatg cagagctcga acggcggttg ggcgcgctac   1260

gacgtcgaca acacgagcga tctcccgaac cacaccccgt tctgcgactt cggcgaagtg   1320

accgatccgc cgtcagagga cgtcaccgcc cacgtgctcg agtgtttcgg cagcttcggg   1380

tacgatgacg cctggaaggt catccggcgc gcggtggaat atctcaagcg ggagcagaag   1440

ccggacggca gctggttcgg tcgttggggc gtcaattacc tctacggcac gggcgcggtg   1500

gtgtcggcgc tgaaggcggt cgggatcgac acgcgcgagc cgtacattca aaaggcgctc   1560

gactgggtcg agcagcatca gaacccggac ggcggctggg gcgaggactg ccgctcgtac   1620

gaggatccgg cgtacgcggg taagggcgcg agcaccccgt cgcagacggc ctgggcgctg   1680

atggcgctca tcgcgggcgg cagggcggag tccgaggccg cgcgccgcgg cgtgcaatac   1740

ctcgtggaga cgcagcgccc ggacggcggc tgggatgagc cgtactacac cggcacgggc   1800

ttcccagggg atttctacct cggctacacc atgtaccgcc acgtgtttcc gacgctcgcg   1860

ctcggccgct acaagcaagc catcgagcgc aggtga                             1896
```

<210> SEQ ID NO 15
<211> LENGTH: 608
<212> TYPE: PRT
<213> ORGANISM: Zymomonas mobilis

<400> SEQUENCE: 15

```
Met Gly Ile Asp Arg Met Asn Ser Leu Ser Arg Leu Leu Met Lys Lys
1               5                   10                  15

Ile Phe Gly Ala Glu Lys Thr Ser Tyr Lys Pro Ala Ser Asp Thr Ile
            20                  25                  30

Ile Gly Thr Asp Thr Leu Lys Arg Pro Asn Arg Arg Pro Glu Pro Thr
        35                  40                  45

Ala Lys Val Asp Lys Thr Ile Phe Lys Thr Met Gly Asn Ser Leu Asn
    50                  55                  60

Asn Thr Leu Val Ser Ala Cys Asp Trp Leu Ile Gly Gln Gln Lys Pro
65                  70                  75                  80

Asp Gly His Trp Val Gly Ala Val Glu Ser Asn Ala Ser Met Glu Ala
                85                  90                  95

Glu Trp Cys Leu Ala Leu Trp Phe Leu Gly Leu Glu Asp His Pro Leu
            100                 105                 110

Arg Pro Arg Leu Gly Asn Ala Leu Leu Glu Met Gln Arg Glu Asp Gly
        115                 120                 125

Ser Trp Gly Val Tyr Phe Gly Ala Gly Asn Gly Asp Ile Asn Ala Thr
    130                 135                 140

Val Glu Ala Tyr Ala Ala Leu Arg Ser Leu Gly Tyr Ser Ala Asp Asn
145                 150                 155                 160

Pro Val Leu Lys Lys Ala Ala Ala Trp Ile Ala Glu Lys Gly Gly Leu
                165                 170                 175
```

-continued

Lys Asn Ile Arg Val Phe Thr Arg Tyr Trp Leu Ala Leu Ile Gly Glu
180 185 190

Trp Pro Trp Glu Lys Thr Pro Asn Leu Pro Pro Glu Ile Ile Trp Phe
195 200 205

Pro Asp Asn Phe Val Phe Ser Ile Tyr Asn Phe Ala Gln Trp Ala Arg
210 215 220

Ala Thr Met Val Pro Ile Ala Ile Leu Ser Ala Arg Arg Pro Ser Arg
225 230 235 240

Pro Leu Arg Pro Gln Asp Arg Leu Asp Glu Leu Phe Pro Glu Gly Arg
245 250 255

Ala Arg Phe Asp Tyr Glu Leu Pro Lys Lys Glu Gly Ile Asp Leu Trp
260 265 270

Ser Gln Phe Phe Arg Thr Thr Asp Arg Gly Leu His Trp Val Gln Ser
275 280 285

Asn Leu Leu Lys Arg Asn Ser Leu Arg Glu Ala Ala Ile Arg His Val
290 295 300

Leu Glu Trp Ile Ile Arg His Gln Asp Ala Asp Gly Gly Trp Gly Gly
305 310 315 320

Ile Gln Pro Pro Trp Val Tyr Gly Leu Met Ala Leu His Gly Glu Gly
325 330 335

Tyr Gln Leu Tyr His Pro Val Met Ala Lys Ala Leu Ser Ala Leu Asp
340 345 350

Asp Pro Gly Trp Arg His Asp Arg Gly Glu Ser Ser Trp Ile Gln Ala
355 360 365

Thr Asn Ser Pro Val Trp Asp Thr Met Leu Ala Leu Met Ala Leu Lys
370 375 380

Asp Ala Lys Ala Glu Asp Arg Phe Thr Pro Glu Met Asp Lys Ala Ala
385 390 395 400

Asp Trp Leu Leu Ala Arg Gln Val Lys Val Lys Gly Asp Trp Ser Ile
405 410 415

Lys Leu Pro Asp Val Glu Pro Gly Gly Trp Ala Phe Glu Tyr Ala Asn
420 425 430

Asp Arg Tyr Pro Asp Thr Asp Asp Thr Ala Val Ala Leu Ile Ala Leu
435 440 445

Ser Ser Tyr Arg Asp Lys Glu Glu Trp Gln Lys Lys Gly Val Glu Asp
450 455 460

Ala Ile Thr Arg Gly Val Asn Trp Leu Ile Ala Met Gln Ser Glu Cys
465 470 475 480

Gly Gly Trp Gly Ala Phe Asp Lys Asp Asn Asn Arg Ser Ile Leu Ser
485 490 495

Lys Ile Pro Phe Cys Asp Phe Gly Glu Ser Ile Asp Pro Pro Ser Val
500 505 510

Asp Val Thr Ala His Val Leu Glu Ala Phe Gly Thr Leu Gly Leu Ser
515 520 525

Arg Asp Met Pro Val Ile Gln Lys Ala Ile Asp Tyr Val Arg Ser Glu
530 535 540

Gln Glu Ala Glu Gly Ala Trp Phe Gly Arg Trp Gly Val Asn Tyr Ile
545 550 555 560

Tyr Gly Thr Gly Ala Val Leu Pro Ala Leu Ala Ala Ile Gly Glu Asp
565 570 575

Met Thr Gln Pro Tyr Ile Thr Lys Ala Cys Asp Trp Leu Val Ala His
580 585 590

-continued

```
Gln Gln Glu Asp Gly Gly Trp Gly Glu Ser Cys Ser Ser Tyr Met Glu
        595                 600                 605


<210> SEQ ID NO 16
<211> LENGTH: 658
<212> TYPE: PRT
<213> ORGANISM: Zymomonas mobilis

<400> SEQUENCE: 16

Met Thr Val Ser Thr Ser Ser Ala Phe His His Ser Pro Leu Ser Asp
1               5                   10                  15

Asp Val Glu Pro Ile Ile Gln Lys Ala Thr Arg Ala Leu Leu Glu Lys
            20                  25                  30

Gln Gln Gln Asp Gly His Trp Val Phe Glu Leu Glu Ala Asp Ala Thr
        35                  40                  45

Ile Pro Ala Glu Tyr Ile Leu Leu Lys His Tyr Leu Gly Glu Pro Glu
    50                  55                  60

Asp Leu Glu Ile Glu Ala Lys Ile Gly Arg Tyr Leu Arg Arg Ile Gln
65                  70                  75                  80

Gly Glu His Gly Gly Trp Ser Leu Phe Tyr Gly Gly Asp Leu Asp Leu
                85                  90                  95

Ser Ala Thr Val Lys Ala Tyr Phe Ala Leu Lys Met Ile Gly Asp Ser
            100                 105                 110

Pro Asp Ala Pro His Met Leu Arg Ala Arg Asn Glu Ile Leu Ala Arg
        115                 120                 125

Gly Gly Ala Met Arg Ala Asn Val Phe Thr Arg Ile Gln Leu Ala Leu
    130                 135                 140

Phe Gly Ala Met Ser Trp Glu His Val Pro Gln Met Pro Val Glu Leu
145                 150                 155                 160

Met Leu Met Pro Glu Trp Phe Pro Val His Ile Asn Lys Met Ala Tyr
                165                 170                 175

Trp Ala Arg Thr Val Leu Val Pro Leu Leu Val Leu Gln Ala Leu Lys
            180                 185                 190

Pro Val Ala Arg Asn Arg Arg Gly Ile Leu Val Asp Glu Leu Phe Val
        195                 200                 205

Pro Asp Val Leu Pro Thr Leu Gln Glu Ser Gly Asp Pro Ile Trp Arg
    210                 215                 220

Arg Phe Phe Ser Ala Leu Asp Lys Val Leu His Lys Val Glu Pro Tyr
225                 230                 235                 240

Trp Pro Lys Asn Met Arg Ala Lys Ala Ile His Ser Cys Val His Phe
                245                 250                 255

Val Thr Glu Arg Leu Asn Gly Glu Asp Gly Leu Gly Ala Ile Tyr Pro
            260                 265                 270

Ala Ile Ala Asn Ser Val Met Met Tyr Asp Ala Leu Gly Tyr Pro Glu
        275                 280                 285

Asn His Pro Glu Arg Ala Ile Ala Arg Arg Ala Val Glu Lys Leu Met
    290                 295                 300

Val Leu Asp Gly Thr Glu Asp Gln Gly Asp Lys Glu Val Tyr Cys Gln
305                 310                 315                 320

Pro Cys Leu Ser Pro Ile Trp Asp Thr Ala Leu Val Ala His Ala Met
                325                 330                 335

Leu Glu Val Gly Gly Asp Glu Ala Glu Lys Ser Ala Ile Ser Ala Leu
            340                 345                 350

Ser Trp Leu Lys Pro Gln Gln Ile Leu Asp Val Lys Gly Asp Trp Ala
        355                 360                 365
```

-continued

```
Trp Arg Arg Pro Asp Leu Arg Pro Gly Gly Trp Ala Phe Gln Tyr Arg
    370                 375                 380

Asn Asp Tyr Tyr Pro Asp Val Asp Asp Thr Ala Val Val Thr Met Ala
385                 390                 395                 400

Met Asp Arg Ala Ala Lys Leu Ser Asp Leu His Asp Asp Phe Glu Glu
                405                 410                 415

Ser Lys Ala Arg Ala Met Glu Trp Thr Ile Gly Met Gln Ser Asp Asn
            420                 425                 430

Gly Gly Trp Gly Ala Phe Asp Ala Asn Asn Ser Tyr Thr Tyr Leu Asn
        435                 440                 445

Asn Ile Pro Phe Ala Asp His Gly Ala Leu Leu Asp Pro Pro Thr Val
    450                 455                 460

Asp Val Ser Ala Arg Cys Val Ser Met Met Ala Gln Ala Gly Ile Ser
465                 470                 475                 480

Ile Thr Asp Pro Lys Met Lys Ala Ala Val Asp Tyr Leu Leu Lys Glu
                485                 490                 495

Gln Glu Glu Asp Gly Ser Trp Phe Gly Arg Trp Gly Val Asn Tyr Ile
            500                 505                 510

Tyr Gly Thr Trp Ser Ala Leu Cys Ala Leu Asn Val Ala Ala Leu Pro
        515                 520                 525

His Asp His Leu Ala Val Gln Lys Ala Val Ala Trp Leu Lys Thr Ile
    530                 535                 540

Gln Asn Glu Asp Gly Gly Trp Gly Glu Asn Cys Asp Ser Tyr Ala Leu
545                 550                 555                 560

Asp Tyr Ser Gly Tyr Glu Pro Met Asp Ser Thr Ala Ser Gln Thr Ala
                565                 570                 575

Trp Ala Leu Leu Gly Leu Met Ala Val Gly Glu Ala Asn Ser Glu Ala
            580                 585                 590

Val Thr Lys Gly Ile Asn Trp Leu Ala Gln Asn Gln Asp Glu Glu Gly
        595                 600                 605

Leu Trp Lys Glu Asp Tyr Tyr Ser Gly Gly Gly Phe Pro Arg Val Phe
    610                 615                 620

Tyr Leu Arg Tyr His Gly Tyr Ser Lys Tyr Phe Pro Leu Trp Ala Leu
625                 630                 635                 640

Ala Arg Tyr Arg Asn Leu Lys Lys Ala Asn Gln Pro Ile Val His Tyr
                645                 650                 655

Gly Met


<210> SEQ ID NO 17
<211> LENGTH: 684
<212> TYPE: PRT
<213> ORGANISM: Bradyrhizobium japonicum

<400> SEQUENCE: 17

Met Thr Val Thr Ser Ser Ala Ser Ala Arg Ala Thr Arg Asp Pro Gly
1               5                   10                  15

Asn Tyr Gln Thr Ala Leu Gln Ser Thr Val Arg Ala Ala Ala Asp Trp
            20                  25                  30

Leu Ile Ala Asn Gln Lys Pro Asp Gly His Trp Val Gly Arg Ala Glu
        35                  40                  45

Ser Asn Ala Cys Met Glu Ala Gln Trp Cys Leu Ala Leu Trp Phe Met
    50                  55                  60

Gly Leu Glu Asp His Pro Leu Arg Lys Arg Leu Gly Gln Ser Leu Leu
65                  70                  75                  80
```

-continued

```
Asp Ser Gln Arg Pro Asp Gly Ala Trp Gln Val Tyr Phe Gly Ala Pro
                85                  90                  95

Asn Gly Asp Ile Asn Ala Thr Val Glu Ala Tyr Ala Ala Leu Arg Ser
            100                 105                 110

Leu Gly Phe Arg Asp Asp Glu Pro Ala Val Arg Arg Ala Arg Glu Trp
        115                 120                 125

Ile Glu Ala Lys Gly Gly Leu Arg Asn Ile Arg Val Phe Thr Arg Tyr
    130                 135                 140

Trp Leu Ala Leu Ile Gly Glu Trp Pro Trp Glu Lys Thr Pro Asn Ile
145                 150                 155                 160

Pro Pro Glu Val Ile Trp Phe Pro Leu Trp Phe Pro Phe Ser Ile Tyr
                165                 170                 175

Asn Phe Ala Gln Trp Ala Arg Ala Thr Leu Met Pro Ile Ala Val Leu
            180                 185                 190

Ser Ala Arg Arg Pro Ser Arg Pro Leu Pro Pro Glu Asn Arg Leu Asp
        195                 200                 205

Ala Leu Phe Pro His Gly Arg Lys Ala Phe Asp Tyr Glu Leu Pro Val
    210                 215                 220

Lys Ala Gly Ala Gly Gly Trp Asp Arg Phe Phe Arg Gly Ala Asp Lys
225                 230                 235                 240

Val Leu His Lys Leu Gln Asn Leu Gly Asn Arg Leu Asn Leu Gly Leu
                245                 250                 255

Phe Arg Pro Ala Ala Thr Ser Arg Val Leu Glu Trp Met Ile Arg His
            260                 265                 270

Gln Asp Phe Asp Gly Ala Trp Gly Gly Ile Gln Pro Pro Trp Ile Tyr
        275                 280                 285

Gly Leu Met Ala Leu Tyr Ala Glu Gly Tyr Pro Leu Asn His Pro Val
    290                 295                 300

Leu Ala Lys Gly Leu Asp Ala Leu Asn Asp Pro Gly Trp Arg Val Asp
305                 310                 315                 320

Val Gly Asp Ala Thr Tyr Ile Gln Ala Thr Asn Ser Pro Val Trp Asp
                325                 330                 335

Thr Ile Leu Thr Leu Leu Ala Phe Asp Asp Ala Gly Val Leu Gly Asp
            340                 345                 350

Tyr Pro Glu Ala Val Asp Lys Ala Val Asp Trp Val Leu Gln Arg Gln
        355                 360                 365

Val Arg Val Pro Gly Asp Trp Ser Met Lys Leu Pro His Val Lys Pro
    370                 375                 380

Gly Gly Trp Ala Phe Glu Tyr Ala Asn Asn Tyr Tyr Pro Asp Thr Asp
385                 390                 395                 400

Asp Thr Ala Val Ala Leu Ile Ala Leu Ala Pro Leu Arg His Asp Pro
                405                 410                 415

Lys Trp Lys Ala Lys Gly Ile Asp Glu Ala Ile Gln Leu Gly Val Asp
            420                 425                 430

Trp Leu Ile Gly Met Gln Ser Gln Gly Gly Gly Trp Gly Ala Phe Asp
        435                 440                 445

Lys Asp Asn Asn Gln Lys Ile Leu Thr Lys Ile Pro Phe Cys Asp Tyr
    450                 455                 460

Gly Glu Ala Leu Asp Pro Pro Ser Val Asp Val Thr Ala His Ile Ile
465                 470                 475                 480

Glu Ala Phe Gly Lys Leu Gly Ile Ser Arg Asn His Pro Ser Met Val
                485                 490                 495
```

-continued

Gln Ala Leu Asp Tyr Ile Arg Arg Glu Gln Glu Pro Ser Gly Pro Trp
500 505 510

Phe Gly Arg Trp Gly Val Asn Tyr Val Tyr Gly Thr Gly Ala Val Leu
515 520 525

Pro Ala Leu Ala Ala Ile Gly Glu Asp Met Thr Gln Pro Tyr Ile Gly
530 535 540

Arg Ala Cys Asp Trp Leu Val Ala His Gln Gln Ala Asp Gly Gly Trp
545 550 555 560

Gly Glu Ser Cys Ala Ser Tyr Met Asp Val Ser Ala Val Gly Arg Gly
565 570 575

Thr Thr Thr Ala Ser Gln Thr Ala Trp Ala Leu Met Ala Leu Leu Ala
580 585 590

Ala Asn Arg Pro Gln Asp Lys Asp Ala Ile Glu Arg Gly Cys Met Trp
595 600 605

Leu Val Glu Arg Gln Ser Ala Gly Thr Trp Asp Glu Pro Glu Phe Thr
610 615 620

Gly Thr Gly Phe Pro Gly Tyr Gly Val Gly Gln Thr Ile Lys Leu Asn
625 630 635 640

Asp Pro Ala Leu Ser Gln Arg Leu Met Gln Gly Pro Glu Leu Ser Arg
645 650 655

Ala Phe Met Leu Arg Tyr Gly Met Tyr Arg His Tyr Phe Pro Leu Met
660 665 670

Ala Leu Gly Arg Ala Leu Arg Pro Gln Ser His Ser
675 680

<210> SEQ ID NO 18
<211> LENGTH: 642
<212> TYPE: PRT
<213> ORGANISM: Thermosynechococcus elongatus

<400> SEQUENCE: 18

Met Pro Thr Ser Leu Ala Thr Ala Ile Asp Pro Lys Gln Leu Gln Gln
1 5 10 15

Ala Ile Arg Ala Ser Gln Asp Phe Leu Phe Ser Gln Gln Tyr Ala Glu
20 25 30

Gly Tyr Trp Trp Ala Glu Leu Glu Ser Asn Val Thr Met Thr Ala Glu
35 40 45

Val Ile Leu Leu His Lys Ile Trp Gly Thr Glu Gln Arg Leu Pro Leu
50 55 60

Ala Lys Ala Glu Gln Tyr Leu Arg Asn His Gln Arg Asp His Gly Gly
65 70 75 80

Trp Glu Leu Phe Tyr Gly Asp Gly Gly Asp Leu Ser Thr Ser Val Glu
85 90 95

Ala Tyr Met Gly Leu Arg Leu Leu Gly Val Pro Glu Thr Asp Pro Ala
100 105 110

Leu Val Lys Ala Arg Gln Phe Ile Leu Ala Arg Gly Gly Ile Ser Lys
115 120 125

Thr Arg Ile Phe Thr Lys Leu His Leu Ala Leu Ile Gly Cys Tyr Asp
130 135 140

Trp Arg Gly Ile Pro Ser Leu Pro Pro Trp Ile Met Leu Leu Pro Glu
145 150 155 160

Gly Ser Pro Phe Thr Ile Tyr Glu Met Ser Ser Trp Ala Arg Ser Ser
165 170 175

Thr Val Pro Leu Leu Ile Val Met Asp Arg Lys Pro Val Tyr Gly Met
180 185 190

-continued

```
Asp Pro Pro Ile Thr Leu Asp Glu Leu Tyr Ser Glu Gly Arg Ala Asn
        195                 200                 205

Val Val Trp Glu Leu Pro Arg Gln Gly Asp Trp Arg Asp Val Phe Ile
    210                 215                 220

Gly Leu Asp Arg Val Phe Lys Leu Phe Glu Thr Leu Asn Ile His Pro
225                 230                 235                 240

Leu Arg Glu Gln Gly Leu Lys Ala Ala Glu Glu Trp Val Leu Glu Arg
                245                 250                 255

Gln Glu Ala Ser Gly Asp Trp Gly Gly Ile Ile Pro Ala Met Leu Asn
            260                 265                 270

Ser Leu Leu Ala Leu Arg Ala Leu Asp Tyr Ala Val Asp Asp Pro Ile
        275                 280                 285

Val Gln Arg Gly Met Ala Ala Val Asp Arg Phe Ala Ile Glu Thr Glu
    290                 295                 300

Thr Glu Tyr Arg Val Gln Pro Cys Val Ser Pro Val Trp Asp Thr Ala
305                 310                 315                 320

Leu Val Met Arg Ala Met Val Asp Ser Gly Val Ala Pro Asp His Pro
                325                 330                 335

Ala Leu Val Lys Ala Gly Glu Trp Leu Leu Ser Lys Gln Ile Leu Asp
            340                 345                 350

Tyr Gly Asp Trp His Ile Lys Asn Lys Lys Gly Arg Pro Gly Gly Trp
        355                 360                 365

Ala Phe Glu Phe Glu Asn Arg Phe Tyr Pro Asp Val Asp Asp Thr Ala
    370                 375                 380

Val Val Val Met Ala Leu His Ala Val Thr Leu Pro Asn Glu Asn Leu
385                 390                 395                 400

Lys Arg Arg Ala Ile Glu Arg Ala Val Ala Trp Ile Ala Ser Met Gln
                405                 410                 415

Cys Arg Pro Gly Gly Trp Ala Ala Phe Asp Val Asp Asn Asp Gln Asp
            420                 425                 430

Trp Leu Asn Gly Ile Pro Tyr Gly Asp Leu Lys Ala Met Ile Asp Pro
        435                 440                 445

Asn Thr Ala Asp Val Thr Ala Arg Val Leu Glu Met Val Gly Arg Cys
    450                 455                 460

Gln Leu Ala Phe Asp Arg Val Ala Leu Asp Arg Ala Leu Ala Tyr Leu
465                 470                 475                 480

Arg Asn Glu Gln Glu Pro Glu Gly Cys Trp Phe Gly Arg Trp Gly Val
                485                 490                 495

Asn Tyr Leu Tyr Gly Thr Ser Gly Val Leu Thr Ala Leu Ser Leu Val
            500                 505                 510

Ala Pro Arg Tyr Asp Arg Trp Arg Ile Arg Arg Ala Ala Glu Trp Leu
        515                 520                 525

Met Gln Cys Gln Asn Ala Asp Gly Gly Trp Gly Glu Thr Cys Trp Ser
    530                 535                 540

Tyr His Asp Pro Ser Leu Lys Gly Lys Gly Asp Ser Thr Ala Ser Gln
545                 550                 555                 560

Thr Ala Trp Ala Ile Ile Gly Leu Leu Ala Ala Gly Asp Ala Thr Gly
                565                 570                 575

Asp Tyr Ala Thr Glu Ala Ile Glu Arg Gly Ile Ala Tyr Leu Leu Glu
            580                 585                 590

Thr Gln Arg Pro Asp Gly Thr Trp His Glu Asp Tyr Phe Thr Gly Thr
        595                 600                 605
```

```
Gly Phe Pro Cys His Phe Tyr Leu Lys Tyr His Tyr Tyr Gln Gln His
    610                 615                 620

Phe Pro Leu Thr Ala Leu Gly Arg Tyr Ala Arg Trp Arg Asn Leu Leu
625                 630                 635                 640

Ala Thr


<210> SEQ ID NO 19
<211> LENGTH: 720
<212> TYPE: PRT
<213> ORGANISM: Acetobacter pasteurianus

<400> SEQUENCE: 19

Met Asn Met Ala Ser Arg Phe Ser Leu Lys Lys Ile Leu Arg Ser Gly
1               5                   10                  15

Ser Asp Thr Gln Gly Thr Asn Val Asn Thr Leu Ile Gln Ser Gly Thr
            20                  25                  30

Ser Asp Ile Val Arg Gln Lys Pro Ala Pro Gln Glu Pro Ala Asp Leu
        35                  40                  45

Ser Ala Leu Lys Ala Met Gly Asn Ser Leu Thr His Thr Leu Ser Ser
    50                  55                  60

Ala Cys Glu Trp Leu Met Lys Gln Gln Lys Pro Asp Gly His Trp Val
65                  70                  75                  80

Gly Ser Val Gly Ser Asn Ala Ser Met Glu Ala Glu Trp Cys Leu Ala
                85                  90                  95

Leu Trp Phe Leu Gly Leu Glu Asp His Pro Leu Arg Pro Arg Leu Gly
            100                 105                 110

Lys Ala Leu Leu Glu Met Gln Arg Pro Asp Gly Ser Trp Gly Thr Tyr
        115                 120                 125

Tyr Gly Ala Gly Ser Gly Asp Ile Asn Ala Thr Val Glu Ser Tyr Ala
    130                 135                 140

Ala Leu Arg Ser Leu Gly Tyr Ala Glu Asp Asp Pro Ala Val Ser Lys
145                 150                 155                 160

Ala Ala Ala Trp Ile Ile Ser Lys Gly Gly Leu Lys Asn Val Arg Val
                165                 170                 175

Phe Thr Arg Tyr Trp Leu Ala Leu Ile Gly Glu Trp Pro Trp Glu Lys
            180                 185                 190

Thr Pro Asn Leu Pro Pro Glu Ile Ile Trp Phe Pro Asp Asn Phe Val
        195                 200                 205

Phe Ser Ile Tyr Asn Phe Ala Gln Trp Ala Arg Ala Thr Met Met Pro
    210                 215                 220

Leu Ala Ile Leu Ser Ala Arg Arg Pro Ser Arg Pro Leu Arg Pro Gln
225                 230                 235                 240

Asp Arg Leu Asp Ala Leu Phe Pro Gly Gly Arg Ala Asn Phe Asp Tyr
                245                 250                 255

Glu Leu Pro Thr Lys Glu Gly Arg Asp Val Ile Ala Asp Phe Phe Arg
            260                 265                 270

Leu Ala Asp Lys Gly Leu His Trp Leu Gln Ser Ser Phe Leu Lys Arg
        275                 280                 285

Ala Pro Ser Arg Glu Ala Ala Ile Lys Tyr Val Leu Glu Trp Ile Ile
    290                 295                 300

Trp His Gln Asp Ala Asp Gly Gly Trp Gly Gly Ile Gln Pro Pro Trp
305                 310                 315                 320

Val Tyr Gly Leu Met Ala Leu His Gly Glu Gly Tyr Gln Phe His His
                325                 330                 335
```

-continued

```
Pro Val Met Ala Lys Ala Leu Asp Ala Leu Asn Asp Pro Gly Trp Arg
            340                 345                 350

His Asp Lys Gly Asp Ala Ser Trp Ile Gln Ala Thr Asn Ser Pro Val
        355                 360                 365

Trp Asp Thr Met Leu Ser Leu Met Ala Leu His Asp Ala Asn Ala Glu
    370                 375                 380

Glu Arg Phe Thr Pro Glu Met Asp Lys Ala Leu Asp Trp Leu Leu Ser
385                 390                 395                 400

Arg Gln Val Arg Val Lys Gly Asp Trp Ser Val Lys Leu Pro Asn Thr
                405                 410                 415

Glu Pro Gly Gly Trp Ala Phe Glu Tyr Ala Asn Asp Arg Tyr Pro Asp
            420                 425                 430

Thr Asp Asp Thr Ala Val Ala Leu Ile Ala Ile Ala Ser Cys Arg Asn
        435                 440                 445

Arg Pro Glu Trp Gln Ala Lys Gly Val Glu Glu Ala Ile Gly Arg Gly
    450                 455                 460

Val Arg Trp Leu Val Ala Met Gln Ser Ser Cys Gly Gly Trp Gly Ala
465                 470                 475                 480

Phe Asp Lys Asp Asn Asn Lys Ser Ile Leu Ala Lys Ile Pro Phe Cys
                485                 490                 495

Asp Phe Gly Glu Ala Leu Asp Pro Pro Ser Val Asp Val Thr Ala His
            500                 505                 510

Val Leu Glu Ala Phe Gly Leu Leu Gly Leu Pro Arg Asp Leu Pro Cys
        515                 520                 525

Ile Gln Arg Gly Leu Ala Tyr Ile Arg Lys Glu Gln Asp Pro Thr Gly
    530                 535                 540

Pro Trp Phe Gly Arg Trp Gly Val Asn Tyr Leu Tyr Gly Thr Gly Ala
545                 550                 555                 560

Val Leu Pro Ala Leu Ala Ala Leu Gly Glu Asp Met Thr Gln Pro Tyr
                565                 570                 575

Ile Ser Lys Ala Cys Asp Trp Leu Ile Asn Cys Gln Gln Glu Asn Gly
            580                 585                 590

Gly Trp Gly Glu Ser Cys Ala Ser Tyr Met Glu Val Ser Ser Ile Gly
        595                 600                 605

His Gly Ala Thr Thr Pro Ser Gln Thr Ala Trp Ala Leu Met Gly Leu
    610                 615                 620

Ile Ala Ala Asn Arg Pro Gln Asp Tyr Glu Ala Ile Ala Lys Gly Cys
625                 630                 635                 640

Arg Tyr Leu Ile Asp Leu Gln Glu Glu Asp Gly Ser Trp Asn Glu Glu
                645                 650                 655

Glu Phe Thr Gly Thr Gly Phe Pro Gly Tyr Gly Val Gly Gln Thr Ile
            660                 665                 670

Lys Leu Asp Asp Pro Ala Ile Ser Lys Arg Leu Met Gln Gly Ala Glu
        675                 680                 685

Leu Ser Arg Ala Phe Met Leu Arg Tyr Asp Leu Tyr Arg Gln Leu Phe
    690                 695                 700

Pro Ile Ile Ala Leu Ser Arg Ala Ser Arg Leu Ile Lys Leu Gly Asn
705                 710                 715                 720
```

<210> SEQ ID NO 20
<211> LENGTH: 685
<212> TYPE: PRT
<213> ORGANISM: Gluconobacter morbifer

<400> SEQUENCE: 20

-continued

```
Met Ser Pro Ala Asp Ile Ser Thr Lys Ser Ser Ser Phe Gln Arg Leu
1               5                   10                  15

Asp Asn Met Leu Pro Glu Ala Val Ser Ser Ala Cys Asp Trp Leu Ile
            20                  25                  30

Asp Gln Gln Lys Pro Asp Gly His Trp Val Gly Pro Val Glu Ser Asn
        35                  40                  45

Ala Cys Met Glu Ala Gln Trp Cys Leu Ala Leu Trp Phe Leu Gly Gln
    50                  55                  60

Glu Asp His Pro Leu Arg Pro Arg Leu Ala Gln Ala Leu Leu Glu Met
65                  70                  75                  80

Gln Arg Glu Asp Gly Ser Trp Gly Ile Tyr Val Gly Ala Asp His Gly
                85                  90                  95

Asp Ile Asn Thr Thr Val Glu Ala Tyr Ala Ala Leu Arg Ser Met Gly
            100                 105                 110

Tyr Ala Ala Asp Met Pro Ile Met Ala Lys Ser Ala Ala Trp Ile Gln
        115                 120                 125

Gln Lys Gly Gly Leu Arg Asn Val Arg Val Phe Thr Arg Tyr Trp Leu
    130                 135                 140

Ala Leu Ile Gly Glu Trp Pro Trp Asp Lys Thr Pro Asn Leu Pro Pro
145                 150                 155                 160

Glu Ile Ile Trp Leu Pro Asp Asn Phe Ile Phe Ser Ile Tyr Asn Phe
                165                 170                 175

Ala Gln Trp Ala Arg Ala Thr Met Met Pro Leu Thr Ile Leu Ser Ala
            180                 185                 190

Arg Arg Pro Ser Arg Pro Leu Leu Pro Glu Asn Arg Leu Asp Gly Leu
        195                 200                 205

Phe Pro Glu Gly Arg Glu Asn Phe Asp Tyr Glu Leu Pro Val Lys Gly
    210                 215                 220

Glu Glu Asp Leu Trp Gly Arg Phe Phe Arg Ala Ala Asp Lys Gly Leu
225                 230                 235                 240

His Ser Leu Gln Ser Phe Pro Val Arg Arg Phe Val Pro Arg Glu Ala
                245                 250                 255

Ala Ile Arg His Val Ile Glu Trp Ile Ile Arg His Gln Asp Ala Asp
            260                 265                 270

Gly Gly Trp Gly Gly Ile Gln Pro Pro Trp Ile Tyr Gly Leu Met Ala
        275                 280                 285

Leu Ser Val Glu Gly Tyr Pro Leu His His Pro Val Leu Ala Lys Ala
    290                 295                 300

Met Asp Ala Leu Asn Asp Pro Gly Trp Arg Arg Asp Lys Gly Asp Ala
305                 310                 315                 320

Ser Trp Ile Gln Ala Thr Asn Ser Pro Val Trp Asp Thr Met Leu Ala
                325                 330                 335

Val Leu Ala Leu His Asp Ala Gly Ala Glu Asp Arg Tyr Ser Pro Gln
            340                 345                 350

Met Asp Lys Ala Ile Gly Trp Leu Leu Asp Arg Gln Val Arg Val Lys
        355                 360                 365

Gly Asp Trp Ser Ile Lys Leu Pro Asp Thr Glu Pro Gly Gly Trp Ala
    370                 375                 380

Phe Glu Tyr Ala Asn Asp Lys Tyr Pro Asp Thr Asp Asp Thr Ala Val
385                 390                 395                 400

Ala Leu Ile Ala Leu Ala Gly Cys Arg His Arg Pro Glu Trp Arg Glu
                405                 410                 415
```

-continued

```
Arg Asp Ile Glu Gly Ala Ile Ser Arg Gly Val Asn Trp Leu Leu Ala
            420                 425                 430

Met Gln Ser Ser Ser Gly Gly Trp Gly Ala Phe Asp Lys Asp Asn Asn
        435                 440                 445

Arg Ser Ile Leu Thr Lys Ile Pro Phe Cys Asp Phe Gly Glu Ala Leu
    450                 455                 460

Asp Pro Pro Ser Val Asp Val Thr Ala His Val Leu Glu Ala Phe Gly
465                 470                 475                 480

Leu Leu Gly Ile Ser Arg Asn His Pro Ser Val Gln Lys Ala Leu Ala
                485                 490                 495

Tyr Ile Arg Ser Glu Gln Glu Arg Asn Gly Ala Trp Phe Gly Arg Trp
            500                 505                 510

Gly Val Asn Tyr Val Tyr Gly Thr Gly Ala Val Leu Pro Ala Leu Ala
        515                 520                 525

Ala Ile Gly Glu Asp Met Thr Gln Pro Tyr Ile Val Arg Ala Cys Asp
    530                 535                 540

Trp Leu Met Ser Val Gln Gln Glu Asn Gly Gly Trp Gly Glu Ser Cys
545                 550                 555                 560

Ala Ser Tyr Met Asp Ile Asn Ala Val Gly His Gly Val Ala Thr Ala
                565                 570                 575

Ser Gln Thr Ala Trp Ala Leu Ile Gly Leu Leu Ala Ala Lys Arg Pro
            580                 585                 590

Lys Asp Arg Glu Ala Ile Ala Arg Gly Cys Gln Phe Leu Ile Glu Arg
        595                 600                 605

Gln Glu Asp Gly Ser Trp Thr Glu Glu Glu Tyr Thr Gly Thr Gly Phe
    610                 615                 620

Pro Gly Tyr Gly Val Gly Gln Ala Ile Lys Leu Asp Asp Pro Ser Leu
625                 630                 635                 640

Pro Asp Arg Leu Leu Gln Gly Ala Glu Leu Ser Arg Ala Phe Met Leu
                645                 650                 655

Arg Tyr Asp Leu Tyr Arg Gln Tyr Phe Pro Val Met Ala Leu Ser Arg
            660                 665                 670

Ala Arg Arg Met Met Lys Glu Asp Ala Ser Ala Ala Ala
        675                 680                 685


<210> SEQ ID NO 21
<211> LENGTH: 625
<212> TYPE: PRT
<213> ORGANISM: Bacillus megaterium

<400> SEQUENCE: 21

Met Ile Ile Leu Leu Lys Glu Val Gln Leu Glu Ile Gln Arg Arg Ile
1               5                   10                  15

Ala Tyr Leu Arg Pro Thr Gln Lys Asn Asp Gly Ser Phe Arg Tyr Cys
            20                  25                  30

Phe Glu Thr Gly Val Met Pro Asp Ala Phe Leu Ile Met Leu Leu Arg
        35                  40                  45

Thr Phe Asp Leu Asp Lys Glu Val Leu Ile Lys Gln Leu Thr Glu Arg
    50                  55                  60

Ile Val Ser Leu Gln Asn Glu Asp Gly Leu Trp Thr Leu Phe Asp Asp
65                  70                  75                  80

Glu Glu His Asn Leu Ser Ala Thr Ile Gln Ala Tyr Thr Ala Leu Leu
                85                  90                  95

Tyr Ser Gly Tyr Tyr Gln Lys Asn Asp Arg Ile Leu Arg Lys Ala Glu
            100                 105                 110
```

-continued

```
Arg Tyr Ile Ile Asp Ser Gly Gly Ile Ser Arg Ala His Phe Leu Thr
        115                 120                 125

Arg Trp Met Leu Ser Val Asn Gly Leu Tyr Glu Trp Pro Lys Leu Phe
    130                 135                 140

Tyr Leu Pro Leu Ser Leu Leu Leu Val Pro Thr Tyr Val Pro Leu Asn
145                 150                 155                 160

Phe Tyr Glu Leu Ser Thr Tyr Ala Arg Ile His Phe Val Pro Met Met
                165                 170                 175

Val Ala Gly Asn Lys Lys Phe Ser Leu Thr Ser Arg His Thr Pro Ser
            180                 185                 190

Leu Ser His Leu Asp Val Arg Glu Gln Lys Gln Glu Ser Glu Glu Thr
        195                 200                 205

Thr Gln Glu Ser Arg Ala Ser Ile Phe Leu Val Asp His Leu Lys Gln
    210                 215                 220

Leu Ala Ser Leu Pro Ser Tyr Ile His Lys Leu Gly Tyr Gln Ala Ala
225                 230                 235                 240

Glu Arg Tyr Met Leu Glu Arg Ile Glu Lys Asp Gly Thr Leu Tyr Ser
                245                 250                 255

Tyr Ala Thr Ser Thr Phe Phe Met Ile Tyr Gly Leu Leu Ala Leu Gly
            260                 265                 270

Tyr Lys Lys Asp Ser Phe Val Ile Gln Lys Ala Ile Asp Gly Ile Cys
        275                 280                 285

Ser Leu Leu Ser Thr Cys Ser Gly His Val His Val Glu Asn Ser Thr
    290                 295                 300

Ser Thr Val Trp Asp Thr Ala Leu Leu Ser Tyr Ala Leu Gln Glu Ala
305                 310                 315                 320

Gly Val Pro Gln Gln Asp Pro Met Ile Lys Gly Thr Thr Arg Tyr Leu
                325                 330                 335

Lys Lys Arg Gln His Thr Lys Leu Gly Asp Trp Gln Phe His Asn Pro
            340                 345                 350

Asn Thr Ala Pro Gly Gly Trp Gly Phe Ser Asp Ile Asn Thr Asn Asn
        355                 360                 365

Pro Asp Leu Asp Asp Thr Ser Ala Ala Ile Arg Ala Leu Ser Arg Arg
    370                 375                 380

Ala Gln Thr Asp Thr Asp Tyr Leu Glu Ser Trp Gln Arg Gly Ile Asn
385                 390                 395                 400

Trp Leu Leu Ser Met Gln Asn Lys Asp Gly Gly Phe Ala Ala Phe Glu
                405                 410                 415

Lys Asn Thr Asp Ser Ile Leu Phe Thr Tyr Leu Pro Leu Glu Asn Ala
            420                 425                 430

Lys Asp Ala Ala Thr Asp Pro Ala Thr Ala Asp Leu Thr Gly Arg Val
        435                 440                 445

Leu Glu Cys Leu Gly Asn Phe Ala Gly Met Asn Lys Ser His Pro Ser
    450                 455                 460

Ile Lys Ala Ala Val Lys Trp Leu Phe Asp His Gln Leu Asp Asn Gly
465                 470                 475                 480

Ser Trp Tyr Gly Arg Trp Gly Val Cys Tyr Ile Tyr Gly Thr Trp Ala
                485                 490                 495

Ala Ile Thr Gly Leu Arg Ala Val Gly Val Ser Ala Ser Asp Pro Arg
            500                 505                 510

Ile Ile Lys Ala Ile Asn Trp Leu Lys Ser Ile Gln Gln Glu Asp Gly
        515                 520                 525
```

-continued

Gly Phe Gly Glu Ser Cys Tyr Ser Ala Ser Leu Lys Lys Tyr Val Pro
    530                 535                 540

Leu Ser Phe Ser Thr Pro Ser Gln Thr Ala Trp Ala Leu Asp Ala Leu
545                 550                 555                 560

Met Thr Ile Cys Pro Leu Lys Asp Gln Ser Val Glu Lys Gly Ile Lys
                565                 570                 575

Phe Leu Leu Asn Pro Asn Leu Thr Glu Gln Gln Thr His Tyr Pro Thr
            580                 585                 590

Gly Ile Gly Leu Pro Gly Gln Phe Tyr Ile Gln Tyr His Ser Tyr Asn
        595                 600                 605

Asp Ile Phe Pro Leu Leu Ala Leu Ala His Tyr Ala Lys Lys His Ser
    610                 615                 620

Ser
625

<210> SEQ ID NO 22
<211> LENGTH: 631
<212> TYPE: PRT
<213> ORGANISM: Artificial sequence
<220> FEATURE:
<223> OTHER INFORMATION: SHC enzyme variant #49

<400> SEQUENCE: 22

Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Arg Trp Leu Ala Leu Val Gly Glu Tyr Pro Trp Glu Lys
    130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Val
    210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

-continued

```
Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365

Asn Val Tyr Tyr Pro Asp Val Asp Asp Thr Ala Val Val Val Trp Ala
    370                 375                 380

Leu Asn Thr Leu Arg Leu Pro Asp Glu Arg Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn Leu Thr
            420                 425                 430

Pro Phe Cys Asp Phe Gly Glu Val Thr Asp Pro Pro Ser Glu Asp Val
        435                 440                 445

Thr Ala His Val Leu Glu Cys Phe Gly Ser Phe Gly Tyr Asp Asp Ala
    450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
        515                 520                 525

Pro Asp Gly Gly Trp Gly Glu Asp Cys Arg Ser Tyr Glu Asp Pro Ala
    530                 535                 540

Tyr Ala Gly Lys Gly Ala Ser Thr Pro Ser Gln Thr Thr Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
        595                 600                 605

Tyr Thr Met Tyr Arg His Val Phe Pro Thr Leu Ala Leu Gly Arg Tyr
    610                 615                 620

Lys Gln Ala Ile Glu Arg Arg
625                 630
```